United States Patent
Wooddell et al.

(10) Patent No.: US 10,006,025 B2
(45) Date of Patent: Jun. 26, 2018

(54) COMPOSITIONS AND METHODS FOR INHIBITING GENE EXPRESSION OF ALPHA-1 ANTITRYPSIN

(71) Applicant: Arrowhead Madison Inc., Madison, WI (US)

(72) Inventors: Christine I Wooddell, Madison, WI (US); David L Lewis, Madison, WI (US); Darren H Wakefield, Fitchburg, WI (US); Lauren Almeida, Madison, WI (US); Steven B Kanner, Madison, WI (US)

(73) Assignee: Arrowhead Pharmaceuticals, Inc., Pasadena, CA (US)

( * ) Notice: Subject to any disclaimer, the term of this patent is extended or adjusted under 35 U.S.C. 154(b) by 72 days.

(21) Appl. No.: 14/740,307

(22) Filed: Jun. 16, 2015

(65) Prior Publication Data
US 2015/0361427 A1    Dec. 17, 2015

Related U.S. Application Data

(60) Provisional application No. 62/013,288, filed on Jun. 17, 2014.

(51) Int. Cl.
*C12N 15/113* (2010.01)

(52) U.S. Cl.
CPC ........ *C12N 15/113* (2013.01); *C12N 2310/14* (2013.01); *C12N 2310/315* (2013.01); *C12N 2310/321* (2013.01); *C12N 2310/322* (2013.01); *C12N 2310/323* (2013.01); *C12N 2310/3515* (2013.01)

(58) Field of Classification Search
CPC ...... A61K 48/00; C12N 15/111; C12N 15/113
See application file for complete search history.

(56) References Cited

U.S. PATENT DOCUMENTS

| | | | |
|---|---|---|---|
| 3,687,808 A | 8/1972 | Merigan, Jr. et al. | |
| 5,034,506 A | 7/1991 | Summerton et al. | |
| 5,134,066 A | 7/1992 | Rogers et al. | |
| 5,212,295 A | 5/1993 | Cook | |
| 5,359,044 A | 10/1994 | Cook et al. | |
| 5,459,255 A | 10/1995 | Cook et al. | |
| 5,466,786 A | 11/1995 | Buhr et al. | |
| 5,489,677 A | 2/1996 | Sanghvi et al. | |
| 5,519,134 A | 5/1996 | Acevedo et al. | |
| 5,521,302 A | 5/1996 | Cook | |
| 5,539,082 A | 7/1996 | Nielson et al. | |
| 5,552,540 A | 9/1996 | Haralambidis | |
| 5,587,361 A | 12/1996 | Cook et al. | |
| 5,591,722 A | 1/1997 | Montgomery et al. | |
| 5,594,121 A | 1/1997 | Froehler et al. | |
| 5,596,091 A | 1/1997 | Switzer | |
| 5,597,909 A | 1/1997 | Urdea et al. | |
| 5,602,240 A | 2/1997 | De Mesmaeker et al. | |
| 5,646,265 A | 7/1997 | McGee | |
| 5,700,920 A | 12/1997 | Altmann et al. | |
| 5,885,968 A | 3/1999 | Biessen et al. | |
| 6,172,209 B1 | 1/2001 | Manoharan et al. | |
| 6,268,490 B1 | 7/2001 | Imanishi | |
| 6,271,358 B1 | 8/2001 | Manoharan et al. | |
| 7,335,765 B2 | 2/2008 | Kaneko et al. | |
| 7,691,997 B2 | 4/2010 | Khvorova et al. | |
| 8,084,599 B2 | 12/2011 | Rossi et al. | |
| 8,349,809 B2 | 1/2013 | Brown | |
| 8,513,207 B2 | 8/2013 | Brown | |
| 9,340,784 B2 | 5/2016 | Monia et al. | |
| 9,458,457 B2 | 10/2016 | Brown et al. | |
| 2005/0137153 A1 | 6/2005 | McSwiggen et al. | |
| 2010/0056768 A1 | 3/2010 | Wengel | |
| 2011/0028531 A1 | 2/2011 | Feinstein et al. | |
| 2013/0190484 A1 | 7/2013 | Rozema et al. | |
| 2014/0235693 A1 | 8/2014 | Sehgal et al. | |
| 2014/0350071 A1 | 11/2014 | Sehgal et al. | |
| 2015/0011607 A1* | 1/2015 | Brown ................. | C12N 15/113 514/44 A |
| 2016/0244752 A1 | 8/2016 | Sehgal et al. | |

FOREIGN PATENT DOCUMENTS

| | | | |
|---|---|---|---|
| JP | 2013539967 A | * | 10/2013 |
| WO | 1993/007883 | | 4/1993 |
| WO | 1999/014226 A2 | | 3/1999 |
| WO | 1999038987 A1 | | 8/1999 |
| WO | 200053722 A2 | | 9/2000 |

(Continued)

OTHER PUBLICATIONS

Guzaev AP et al., "A Conformationally Preorganized Universal Solid Support for Efficient Oligonucleotide Synthesis," J. Am. Chem. Soc. (2003) 125: 2380-2381.
Wagner RW, "The state of the art in antisense research." Nature Medicine (1995) 1(11): 1116-1118.
Braasch, D.A. and Corey, D.R. "Locked Nucleic Acid (LNA): Finetuning the Recognition of DNA and RNA," Chem. Biol. (2001) 8, 1-7.
Elman, J. et al, "Locked Nucleic Acid (LNA) Mediated Improvements in siRNA Stability and Functionality," Nucleic Acids Res. (2005); 33(1): 439-447.
Kurreck, J. et al, "Design of Antisense Oligonucleotides Stabilized by Locked Nucleic Acids," Nucleic Acids Res. (2002) 30, 1911-1918.
Crinelli, R. et al. "Design and Characterization of Decoy Oligonucleotides Containing Locked Nucleic Acids," Nucleic Acids Res. (2002) 30, 2435-2443.
Wahlestedt, C et al., "Potent and Nontoxic Antisense Oligonucleotides Containing Locked Nucleic Acids," Proc. Natl. Acad. Sci. USA (2000) 97, 5633-5638.
Bondensgaard, K. et al., "Structural Studies of LNA:RNA Duplexes by NMR: Conformations and RNase H Activity," Chem. Eur. J., 6 (2000), pp. 2687-2695.

(Continued)

*Primary Examiner* — J. E. Angell
(74) *Attorney, Agent, or Firm* — Robert Michael Teigen

(57) ABSTRACT

The invention relates to a RNA interference triggers for inhibiting the expression of an AAT gene through the mechanism of RNA interference. The invention also relates to a pharmaceutical composition comprising the AAT RNAi trigger together with an excipient capable of improving delivery of the RNAi trigger to a liver cell in vivo. Delivery of the AAT RNAi trigger to liver cells in vivo provides for inhibition of AAT gene expression and treatment of alpha 1-antitrypsin deficiency and associated diseases.

25 Claims, 15 Drawing Sheets

(56) References Cited

FOREIGN PATENT DOCUMENTS

| WO | 2004/083430 | 9/2004 |
| WO | 2008022309 A2 | 2/2008 |
| WO | 2011104169 A1 | 9/2011 |
| WO | 2012033848 A1 | 3/2012 |
| WO | 2012083185 A2 | 6/2012 |
| WO | 2013142514 A1 | 9/2013 |
| WO | 2014190137 A1 | 11/2014 |
| WO | 2014197524 A2 | 12/2014 |
| WO | 2015003113 A2 | 1/2015 |

OTHER PUBLICATIONS

Shuling, G. et al. "Antisense oligonucleotide treatment ameliorates alpha-1 antitrypsin related liver disease in mince." The Journal of Clinical Investigation. (2014), vol. 124, pp. 251-261.

Written Opinion of the International Searching Authority for corresponding Application PCT/US15/35976.

Crooke et al., "Pharmacokinetic Properties of Several Novel Oligonucleotide Analogs in Mice." J. Pharmacal. Exp. Ther. (1996), 277: 923-927.

Kabanov et al., "A new class of antivirals; antisense oligonucleotides combined with a hydrophobic substituent effectively inhibit influenza virus reproduction and synthesis of virus-specific proteins in MDCK cells," FEBS Lett. (1990) 259: 327-330.

Letsinger RL et al., "Cholesteryl-conjugated oligonucleotides: Synthesis, properties, and activity as inhibitors of replication of human immunodeficiency virus in cell culture," Proc. Natl. Acad. Sci. USA (1989) 86: 6553-6556.

Manoharan M et al., "Lipidic Nucleic Acids," Tetrahedron Letters (1995) 36: 3651-3654.

Mishra RK et al., "Improved leishmanicidal effect of phosphorothioate antisense oligonucleotides by LDL-mediated delivery," Biochim. et Biophysica Acta (1995) 1264: 229-237.

Saison-Behmoaras et al., "Short Modified Antisense Oligonucleotides Directed Against Ha-ras Point Mutation Induce Selective Cleavage of the mRNA and Inhibit T24 Cells Proliferation," The EMBO Journal (1991) 10: 1111-1118.

Shea et al., "Synthesis, Hybridization Properties and Antiviral Activity of Lipid-oligodeoxynucleotide Conjugates," Nucl. Acids Research (1990) 18: 3777-3783.

Svinarchuk et al, "Inhibition of HIV proliferation in MT-4 cells by antisense oligonucleotide conjugated to lipophilic groups," Biochimie (1993) 75: 49-54.

American Thoracic Society/European Respiratory Society Statement. Standards for the diagnosis and management of individuals with alpha-1 antitrypsin deficiency. Am J Respir Crit Care Med. 2003;168(7):818-900.

Bats R "Alpha-1-antitrypsin deficiency, Best Practice & Research Clinical Gastroenterology" 2010 vol. 24:629-633.

Mueller C et al. "Sustained miRNA mediated Knockdown of Mutant AAT With Simultaneous augmentation of Wild-type AAT Has Minimal Effect on Global Liver miRNA Profiles." Mol Ther., Mar. 2012;20(3):590-600.

Carrell R et al., Alpha 1 Antitrypsin Deficiency—A model for Conformational Diseases. N Engl J Med, vol. 346, No. 1 Jan. 3, 2002, pp. 45-53.

Carlson J et al., Accumulation of PiZ α1-Antitrypsin Causes Liver Damage in Transgenic Mice. J Clin Invest 1989 83:1183-1190.

Cichy et al. JBC 1997; 272(13): 8250-5.

Cohen A "Interrelationships between the Human Alveolar Macrophage and Alpha-1-Antitrypsin" J Clin Invest., 1973: 52(11) 2793-99.

de Serres "Prevalence of α1-antitrypsin deficiency alleles PI*S and PI*Z worldwide and effective screening for each of the five phenotypic classes PI*MS, PI*MZ, PI*SS, PI*SZ, and PI*ZZ: a comprehensive review." Ther Adv Respir Dis, 2012 6(5) 277-295.

Elzouki AN et al. "Risk of hepatobiliary disease in adults with severe alpha 1-antitrypsin deficiency (PiZZ): is chronic viral hepatitis B or C an additional risk factor for cirrhosis and hepatocellular carcinoma?" Eur J Gastroenterol Hepatol. 1996; vol. 8:989-994.

Eriksson S. "Alpha-1-antitrypsin deficiency: natural course and therapeutic strategies." In: Boyer JL, Blum HE, Maier K-P, Sauerbruch T, Stalder GA, editors. Falk Symposium 115: Liver cirrhosis and its development. Dordrecht: Kluwer Academic Publishers; 2001. p. 307-15.

Feldmann G et al. "The ultrastructure of hepatocytes in alpha-1 antitrypsin deficiency with the genotype Pi_ _." Gut 1975, vol. 16 p. 796-799.

Flotte T, et al. "Gene Therapy for alpha-1 antitrypsin deficiency." Human Molecular Genetics, 2011, vol. 20 Issue 1. R87-92.

Greene CM et al. "Z a-1 antitrypsin deficiency and the endoplasmic reticulum stress response." World J Gastroint Pharmacol Ther 2010 vol. 1:94-101.

Hunt JM et al. "Alpha-1-Antitrypsin: One Protein, Many Functions." Current Molecular Medicine. 2012, 12, 827-835.

Kemmer N et al. "Alpha-1-antitrpysin deficiency: outcomes after liver transplantation." Transplant Proc. 2008; 40(5):1492-1494.

Lindblad D et al. "Alpha-1-antitrypsin mutant Z protein content in individual hepatocytes correlates with cell death in a mouse model." Hepatology 2007 vol. 46: 1228-1235.

Lomas DA et al. "The mechanism of Z alpha 1-antitrypsin accumulation in the liver." Nature 1992 357: 605-607.

Long et al. "Complete sequence of the cDNA for human alpha-1-antitrypsin and the gene for the S variant." Biochemistry 1984; 23: 4828-4837.

Nelson D et al. "Diagnosis and Management of Patients with a1-Antitrypsin (A1AT) Deficiency." Clin Gastroenterol Hepatol. Jun. 2012; 10(6): 575-580.

Paako, et al. Am J Respir Crit Care Med. 1996;154(6 pt 1):1829-33.

Perlmutter DH et al. "Hepatic fibrosis and carcinogenesis in alpha1-antitrypsin deficiency: a prototype for chronic tissue damage in gain of function disorders." Cold Spring Harb Perspect Biol. 2011; pp. 1-14.

Perlmutter, DH "Alpha-1-antitrypsin deficiency: importance of proteasomal and autophagic degradative pathways in disposal of liver disease-associated protein aggregates." Annu Rev Med 2011 vol. 62: 333-345.

Propst T, et al. Prevalence of hepatocellular carcinoma in alpha-1-antitrypsin deficiency. J Hepatol 1994 vol. 21:1006-1011.

Sehgal K et al. "Developing an RNAi Therapeutic for Liver Disease Associated With Alpha-1-Antitrypsin Deficiency" Presented as a poster at AASLD, Nov. 2013.

Song HK et al. "Crystal structure of an uncleaved alpha 1-antitrypsin reveals the conformation of its inhibitory reactive loop." FEBS Lett. (1995) vol. 377, 150-154.

Stoller JK, Aboussouan LS. A Review of α1-Antitrypsin Deficiency. Am J Respir Crit Care Med 2012;185:246-259.

Sveger, T. "Liver disease in alpha1-antitrypsin deficiency detected by screening of 200,000 infants." N. Engl. J. Med., 1976 vol. 294, 1316-1321.

Teckman J "Liver Disease in Alpha-1 Antitrypsin Deficiency: Current Understanding and Future Therapy." Journal of Chronic Obstructive Pulmonary Disease 10)S1):35-43, 2013.

Teckman J "Mitochondrial Autophagy and injury in the liver in alpha-1-antitrypsin deficiency." Am J Physiol Gastrointest Liver Physiol., 2003, 286:G851-862.

Teckman J et al. "Advances in Alpha-1-Antitrypsin Deficiency Liver Disease." Curr Gastroenterol Rep (2014) 16:367.

Venembre et al., "Secretion of alpha 1-antitrypsin by alveolar epithelial cells", FEBS Lett. 1994; 346(2-3):171-4.

Cruz, P et al. "In vivo post-transcriptional gene silencing of alpha-1 antitrypsin by adeno-associated virus vectors expressing siRNA." Lab Invest. (2007) 87, 893-902.

Baenziger JU et al. "Galactose and N-acetylgalactosamine-specific endocytosis of glycopeptides by isolated rat hepatocytes" Cell 1980, 22(2): 611-620.

Connolly et al. "Binding and endocytosis of cluster glycosides by rabbit hepatocytes. Evidence for a short-circuit pathway that does not lead to degradation" Journal of Biological Chemistry (1982) 257(2): 939-945.

(56) References Cited

OTHER PUBLICATIONS

Biessen et al. "Synthesis of Cluster Galactosides with High Affinity for the Hepatic Asialoglycoprotein Receptor" Journal of Medicinal Chemistry (1995) 38(9): 1538-1546.

Iobst ST et al. "Selective Sugar Binding to the Carbohydrate Recognition Domains of the Rat Hepatic and Macrophage Asialoglycoprotein Receptors." Journal of Biological Chemistry (1996) 271(12), p. 6686-6693.

Hamm ML et al., "Incorporation of 2'-Deoxy-2'-mercaptocytidine into Oligonucleotides via Phosphoramidite Chemistry," J. Org. Chem. (1997) 62: 3415-3420.

Thomson JB et al., "Synthesis and Properties of Diuridine Phosphate Analogues Containing Thio and Amino Modifications," J. Org. Chem. (1996) 61: 6273-6281.

Cook PD, "Medicinal Chemistry of Antisense Oligonucleotides—Future Opportunities." Anti-Cancer Drug Design (1991) 6: 585-607.

Delgado C et al., "The Uses and Properties of PEG-Linked Proteins," Critical Reviews in Therapeutic Drug Carrier Systems (1992) 9(3,4): 249-304.

Nielsen, P et al, "Incorporation of (R)- and (S)-3',4'-seco-thymidine into oligodeoxynucleotides: hybridization properties and enzymatic stability." Nucleic Acids Research, 1994, vol. 22, No. 5, pp. 703-710.

Nielsen, P et al.,"Synthesis and evaluation of oligodeoxynucleotides containing acyclic nucleosides: Introduction of three novel analogues and a summary." Bioorganic & Medicinal Chemistry, 1995, vol. 3, Issue 1, pp. 19-28.

\* cited by examiner

Table 1. AAT RNAi trigger molecule core sequences.

| SEQ ID No. | antisense strand sequence 5'→3' guide sequence | SEQ ID No. | sense strand sequence 5'→3' 18mer AAT mRNA target site sequence | AAT mRNA position | SEQ ID pair |
|---|---|---|---|---|---|
| 1 | GGAACUUGGUGAUGAUAU | 8 | AUAUCAUCACCAAGUUCC | 1142-1160 | 1/8 |
| 2 | GAUCAUAGGUUCCAGUAA | 9 | UUACUGGAACCUAUGAUC | 1211-1229 | 2/9 |
| 3 | ACAGCCUUAUGCACGGCC | 10 | GGCCGUGCAUAAGGCUGU | 1326-1344 | 3/10 |
| 4 | UCGAUGGUCAGCACAGCC | 11 | GGCUGUGCUGACCAUCGA | 1338-1356 | 4/11 |
| 5 | CAAAGGGUUUGUUGAACU | 12 | AGUUCAACAAACCCUUUG | 1427-1445 | 5/12 |

FIG. 1

Table 2. AAT RNAi trigger molecule core sequences with 5' and 3' overhang nucleotides.

| SEQ ID No. | core SEQ ID | antisense strand sequence 5' → 3' | SEQ ID No. | core SEQ ID | sense strand sequence 5' → 3' | SEQ ID pair or SEQ ID mero |
|---|---|---|---|---|---|---|
| 15 | 1 | TGGAACUUGGUGAUGAUAUTT | 23 | 8 | AUAUCAUCACCAAGUUCCAT | 15/23 |
| 15 | 1 | TGGAACUUGGUGAUGAUAUTT | 24 | 8 | UAUAUAUCACCAAGUUCCAT | 15/24 |
| 15 | 1 | TGGAACUUGGUGAUGAUAUTT | 25 | 8 | UAUAUAUCAUCA CCAAGUUCCAT | 15/25/41 |
| 15 | 1 | TGGAACUUGGUGAUGAUAUTT | 26 | 8 | UAUAUAUCAUCAC CAAGUUCCAT | 15/26/42 |
| 15 | 1 | TGGAACUUGGUGAUGAUAUTT | 27 | 8 | UAUAUAUCAUCACC AAGUUCCAT | 15/27/43 |
| 16 | 2 | TGAUCAUAGGUUCCAGUAATT | 28 | 9 | UUACUGGAACCUAUGAUCAT | 16/28 |
| 16 | 2 | TGAUCAUAGGUUCCAGUAATT | 29 | 9 | UAUUUACUGGAAC CUAUGAUCAT | 16/29/44 |
| 17 | 3 | TACAGCCUUAUGCACGGCCTT | 30 | 10 | GGCCGUGCAUAAGGCUGUAT | 17/30 |
| 18 | 4 | TUCGAUGGUCAGCACAGCCTT | 31 | 11 | GGCUGUGCUGACCAUCGAAT | 18/31 |
| 18 | 4 | TUCGAUGGUCAGCACAGCCTT | 32 | 11 | UAUGGCUGUGCU GACCAUCGAAT | 18/32/45 |
| 18 | 4 | TUCGAUGGUCAGCACAGCCTT | 33 | 11 | UAUGGCUGUGCUG ACCAUCGAAT | 18/33/46 |
| 18 | 4 | TUCGAUGGUCAGCACAGCCTT | 34 | 11 | UAUGGCUGUGCUGA CCAUCGAAT | 18/34/47 |
| 18 | 4 | TUCGAUGGUCAGCACAGCCTT | 35 | 11 | UAUGGCUGUGC UGACCAUCGAAT | 18/35/48 |
| 19 | 5 | TCAAAGGGUUUGUUGAACUTT | 36 | 12 | AGUUCAACAAACCCUUUGAT | 16/36 |
| 19 | 5 | TCAAAGGGUUUGUUGAACUTT | 37 | 12 | UAUAGUUCAACAAA CCCUUUGAT | 19/37/49 |
| 19 | 5 | TCAAAGGGUUUGUUGAACUTT | 38 | 12 | UAUAGUUCAACAAACCCUUUGAT | 19/38 |

FIG. 2

Table 3A. AAT canonical siRNA RNAi trigger molecules.

| SEQ ID No. | core SEQ ID | antisense strand sequence 5' → 3' | SEQ ID No. | sense strand sequence 5' → 3' | SEQ ID pair |
|---|---|---|---|---|---|
| 50 | 1 | dTGfgAfaCfuUfgGfuGfaUfgAfuAfudTsdT | 62 | AfuAfuCfaUfcAfcCfaAfgUfuCfcAf(invdT) | 50/62 |
| 50 | 1 | dTGfgAfaCfuUfgGfuGfaUfgAfuAfudTsdT | 63 | (Chol-TEG)uAuAfuAfuCfaUfcAfcCfaAfgUfuCfcAf(invdT) | 50/63 |
| 53 | 2 | dTGfaUfcAfuAfgGfuUfcCfaGfuAfadTsdT | 67 | UfuAfcUfgGfaAfcCfuAfuGfaUfcAf(invdT) | 53/67 |
| 54 | 3 | dTAfcAfgCfcUfuAfuGfcAfcGfgCfcdTsdT | 69 | GfgCfcGfuGfcAfuAfaGfgCfuGfuAf(invdT) | 54/69 |
| 55 | 4 | dTUfcGfaUfgGfcCfaGfcAfcAfgCfcdTsdT | 70 | GfgCfuGfuGfcUfgGfcCfaUfcGfaAf(invdT) | 55/70 |
| 56 | 5 | dTCfaAfaGfgGfuUfgGfuGfuGfaCfudTsdT | 75 | AfgUfuCfaAfcAfaAfcCfcUfuUfgAf(invdT) | 56/75 |
| 56 | 5 | dTCfaAfaGfgGfuUfgGfuGfuGfaCfudTsdT | 77 | (Chol-TEG)uAuAfgUfuCfaAfcAfaAfcCfcUfuUfgAf(invdT) | 56/77 |

Table 3B. Canonical AAT siRNA RNAi trigger melting temperatures.

| SEQ ID pair | $T_m$ |
|---|---|
| 50/62 | 77.1 |
| 50/63 | 74 |
| 53/67 | 76.8 |
| 54/69 | 88.7 |
| 55/70 | 88.1 |
| 56/75 | 71.1 |
| 56/77 | 72.8 |

FIG. 3.

Table 4. AAT meroduplex RNAi trigger molecules.

| SEQ ID No. | core SEQ ID | antisense strand sequence 5' → 3' | SEQ ID No. | sense strand sequences 5' → 3' | $T_m$ | SEQ ID mero |
|---|---|---|---|---|---|---|
| 50 | 1 | dTGfgAfaCfuUfgGfuGfaUfgAfuAfudTsdT | 64 | (Chol-TEG)uAuAfuAfuCfaUfcAf cCfaAfgUfuCfcAf(invdT) | 46 | 50/64/81 |
| 50 | 1 | dTGfgAfaCfuUfgGfuGfaUfgAfuAfudTsdT | 65 | (Chol-TEG)uAuAfuAfuCfaUfcAfc CfaAfgUfcCfcAf(invdT) | 46.3 | 50/65/82 |
| 50 | 1 | dTGfgAfaCfuUfgGfuGfaUfgAfuAfudTsdT | 66 | (Chol-TEG)uAuAfuAfuCfaUfcAfcCf aAfgUfcCfaAf(invdT) | 46.3 | 50/66/83 |
| 53 | 2 | dTGfaUfcAfuAfgGfuUfcCfaGfuAfadTsdT | 68 | (Chol-TEG)uAuUfuAfcUfgGfaAfc CfuAfuGfaUfcAf(invdT) | 48.8 | 53/68/84 |
| 55 | 4 | dTUfcGfaUfgGfuCfaGfcAfcAfgCfcdTsdT | 71 | (Chol-TEG)uAuGfgCfuGfuGfcUf gAfcCfaUfcGfaAf(invdT) | 60.1 | 55/71/85 |
| 55 | 4 | dTUfcGfaUfgGfuCfaGfcAfcAfgCfcdTsdT | 72 | (Chol-TEG)uAuGfgCfuGfuGfcUfg AfcCfaUfcGfaAf(invdT) | 57.2 | 55/72/86 |
| 55 | 4 | dTUfcGfaUfgGfuCfaGfcAfcAfgCfcdTsdT | 73 | (Chol-TEG)uAuGfgCfuGfuGfcUfgAf cCfaUfcGfaAf(invdT) | 57.2 | 55/73/87 |
| 55 | 4 | dTUfcGfaUfgGfuCfaGfcAfcAfgCfcdTsdT | 74 | (Chol-TEG)uAuGfgCfuGfuGfcUfgAfc UfgAfcCfaUfcGfaaAf(invdT) | 61.8 | 55/74/88 |
| 56 | 5 | dTCfaAfaGfgGfuUfuGfuUfgAfaCfudTsdT | 76 | (Chol-TEG)uAuAfgUfuCfaAfcAfaAf cCfcUfuUfgAf(invdT) | 46.8 | 56/76/89 |

FIG. 4

Table 5A. AAT UNA RNAi trigger molecules.

| SEQ ID No. | core SEQ ID | antisense strand sequence 5' → 3' | SEQ ID No. | sense strand sequence 5' → 3' | SEQ ID pair |
|---|---|---|---|---|---|
| 51 | 1 | dTGfgAfaCfU$_{UNA}$uUfgGfuGfaUfgGfaUfgAfuAfudTsdT | 63 | (Chol-TEG)uAuAfuAfuCfaUfcAfcCfaAfgUfuCfcAf(invdT) | 51/63 |
| 52 | 1 | dTGfgAfaCfU$_{una}$UfgGfuGfaUfgGfaUfgAfuAfudTsdT | 63 | (Chol-TEG)uAuAfuAfuCfaUfcAfcCfaAfgUfuCfcAf(invdT) | 52/63 |
| 57 | 5 | dTCfaAfaG$_{UNA}$gGfuUfuGfuUfgAfaCfudTsdT | 77 | (Chol-TEG)uAuAfgUfuCfaAfcAfaAfcCfcUfuUfgAf(invdT) | 57/77 |
| 58 | 5 | dTCfaAfaGfG$_{UNA}$GfuUfuGfuUfgAfaCfudTsdT | 77 | (Chol-TEG)uAuAfgUfuCfaAfcAfaAfcCfcUfuUfgAf(invdT) | 58/77 |

Table 5B. AAT UNA RNAi effector duplex melting temperature.

| SEQ ID pair | $T_m$ |
|---|---|
| 51/63 | 59.5 |
| 52/63 | 63.6 |
| 57/77 | 62.5 |
| 58/77 | 61.9 |

FIG. 5

Table 6A. MLP peptide sequences.

| Seq ID | Melittin Sequence | Name |
|---|---|---|
| 90 | GIGAILKVLATGLPTLISWIKNKRKQ | Apis florea |
| 91 | AIGAILKVLATGLPTLISWIKNKRKQ | G1A |
| 92 | CIGAILKVLATGLPTLISWIKNKRKQ | G1C |
| 93 | FIGAILKVLATGLPTLISWIKNKRKQ | G1F |
| 94 | HIGAILKVLATGLPTLISWIKNKRKQ | G1H |
| 95 | IIGAILKVLATGLPTLISWIKNKRKQ | G1I |
| 96 | LIGAILKVLATGLPTLISWIKNKRKQ | G1L |
| 97 | NleIGAILKVLATGLPTLISWIKNKRKQ | G1Nle |
| 98 | VIGAILKVLATGLPTLISWIKNKRKQ | G1V |
| 99 | WIGAILKVLATGLPTLISWIKNKRKQ | G1W |
| 100 | YIGAILKVLATGLPTLISWIKNKRKQ | G1Y |
| 101 | GIGAILKVLACGLPTLISWIKNKRKQ | T11C dMel |
| 102 | GIGAILKVLATLLPTLISWIKNKRKQ | G12L |
| 103 | GIGAILKVLATWLPTLISWIKNKRKQ | G12W |
| 104 | GIGAILKVLATGLPTLISWIKTKRKQ | N22T |
| 105 | YIGAILNVLATGLPTLISWIKNKRKQ | G1Y, K7N |
| 106 | YIGAILAVLATGLPTLISWIKNKRKQ | G1Y, K7A |
| 107 | LIGAILSVLATGLPTLISWIKNKRKQ | G1L, K7S |
| 108 | LIGAILRVLATGLPTLISWIKNKRKQ | G1L, K7R |
| 109 | LIGAILHVLATGLPTLISWIKNKRKQ | G1L, K7H |
| 110 | LIGAILKVLACGLPTLISWIKNKRKQ | G1L, T11C |

FIG. 6A

Table 6B. MLP peptide sequences, continued.

| | | |
|---|---|---|
| 111 | LIGAILKVLATLLPTLISWIKNKRKQ | G1L, G12L |
| 112 | YIGAILKVLATGLLTLISWIKNKRKQ | G1Y, P14L |
| 113 | LIGAILKVLATGLPCLISWIKNKRKQ | G1L, T15C |
| 114 | LIGAILKVLATGLPTLICWIKNKRKQ | G1L, S18C |
| 115 | YIGAILKVLATGLPTLISAIKNKRKQ | G1Y, W19A |
| 116 | GIGAILKVLACGLPTLISWLKNKRKQ | T11C, I20L |
| 117 | YIGAILKVLATGLPTLISWIANKRKQ | G1Y, K21A |
| 118 | YIGAILKVLATGLPTLISWIKNARKQ | G1Y, K23A |
| 119 | LIGAILKVLATGLPTLISWIKNKAKQ | G1L, R24A |
| 120 | YIGAILKVLATGLPTLISWIKNKRAQ | G1Y, K25A |
| 121 | YIGAILKVLATGLPTLISWIKNKRKC | G1Y, Q26C |
| 122 | LLGAILKVLACGLPTLISWIKNKRKQ | G1L, I2L, T11C |
| 123 | LIGAILKVLACGLPTLISWIKNKRKQ | G1L, I5L, T11C |
| 124 | YIGAILAVLATGLPTLISWIANKRKQ | G1Y, K7A, K21A |
| 125 | YIGAILAVLATGLPTLISWIKNARKQ | G1Y, K7A, K23A |
| 126 | LIGAILKVLACGLPTLLSWIKNKRKQ | G1L, T11C, I17L |
| 127 | LIGAILKVLACGLPTLICWIKNKRKQ | G1L, T11C, S18C |
| 128 | GIGAILKVLACGLPGLIGWIKNKRKQ | T11G, T15G, S18G |
| 129 | GIGAILKVLACGLPALIAWIKNKRKQ | T11A, T15A, S18A |
| 130 | YIGAILAVLATGLPTLISWIANARKQ | G1Y, K7A, K21A, K23A |
| 131 | YIAAILKVLAAALATLISWIKNKRKQ | G1Y, G3A, T11A, G12A, P14A |
| 132 | LLGAILKVLATGLPTLLSWLKNKRKQ | G1L, I2L, I5L, I17L, I20L |

FIG. 6B

Table 6C. MLP peptide sequences, continued.

| | | |
|---|---|---|
| 133 | LNleGANleLKVLATGLPTLNleSWNleKNKRRKQ | G1L, I2Nle, I5Nle, I17Nle, I20Nle |
| 134 | LVGAVLKVLATGLPTLVSWVKNKRRKQ | G1L, I2V, I5V, I17V, I20V |
| 135 | GLGAILKVLACGLPTLLSWLKNKRRKQ | I2L, I5L, T11C, I17L, I20L |
| 136 | GNleGANleLKVLACGLPTLNleSWNleKNKRRKQ | I2Nle, I5Nle, T11C, I17Nle, I20Nle |
| 137 | CEDDLLLGAILKVLATGLPTLISWIKNKRRKQ | CEDDL-Mel G1L, I2L |
| 138 | CLVVLIVVAILKVLATGLPTLISWIKNKRRKQ | CLVVL-Mel G1L, I2V, G3V |
| 139 | GIGAVLKVLTTGLPALISWIKRKRRQQ | Apis mellifera |
| 140 | CLIGAILKVLATGLPTLISWIKNKRRKQ | C-Mel G1L |
| 141 | CNleIGAILKVLATGLPTLISWIKNKRRKQ | C-Mel G1Nle |
| 142 | GLIGAILKVLATGLPTLISWIKNKRRKQ | G-Mel G1L |
| 143 | LLIGAILKVLATGLPTLISWIKNKRRKQ | L-Mel G1L |
| 144 | KLKLIGAILKVLATGLPTLISWIKNKRRKQ | KLK-Mel G1L |
| 145 | KLKYIGAILKVLATGLPTLISWIKNKRRKQ | KLK-Mel G1Y |
| 146 | CKLKLIGAILKVLATGLPTLISWIKNKRRKQ | CKLK-Mel G1L |
| 147 | CKLKNleIGAILKVLATGLPTLISWIKNKRRKQ | CKLK-Mel G1Nle |
| 148 | GKLKLIGAILKVLATGLPTLISWIKNKRRKQ | GKLK-Mel G1L |
| 149 | CPANLIGAILKVLATGLPTLISWIKNKRRKQ | CPAN-dMel G1L |
| 150 | DEPLRAIGAILKVLATGLPTLISWIKNKRRKQ | DEPLR-Mel G1A |
| 151 | GIGAILKVLATGLPTLISWIKNKRRKQC | Mel-Cys |
| 152 | LIGAILKVLATGLPTLISWIKNKRRKQC | G1L Mel-Cys |
| 153 | NleIGAILKVLATGLPTLISWIKNKRRKQC | G1Nle Mel-C |
| 154 | LIGAILKVLATGLPTLISWIKNKRRKQKLKC | G1L Mel-KLKC |

FIG. 6C

Table 6D. MLP peptide sequences, continued.

| # | Sequence | Description |
|---|---|---|
| 155 | YIGAILKVLATGLPTLISWIKNKRKQPLGIAGQC | G1Y Mel-PLGIAGQC |
| 156 | LIGAILKVLATGLPTLISWIKNKRKQKKKKK | G1L Mel-KKKKK |
| 157 | YIGAILKVLATGLPTLISWIKNKRKQGFKGC | G1Y Mel-GFKGC |
| 158 | CFKLIGAILKVLATGLPTLISWIKNKRKQC | CFK-G1L Mel-C |
| 159 | FGAILKVLATGLPTLISWIKNKRKQ | G1F, I2Δ |
| 160 | LIGAILKVLATGLPTLISWIKNK | G1L Mel (1-23) |
| 161 | LIGAVLKVLTTGLPALISWIK | G1L, L5V, A10T, T15A Mel (1-23) |
| 162 | LIGAVLKVLTTGLPALISWIKGE | G1L, L5V, A10T, T15A, N22G, K23E Mel (1-23) |
| 163 | QKRKNKIWSILTPLGTALVKLIAGIL | G1L retroMel |
| 164 | KLKQKRKNKIWSILTPLGTALVKLIAGIL | G1L retroMel-KLK |
| 165 | GIGAVLKVLTTGLPALISWISRKKRQQ | I5V, A10T, T15A, N22R, R24K, K25R Mel-Q |
| 166 | GIGARLKVLTTGLPR ISWKRKRKRQQ | I5R, A10T, T15R, L16Δ, N22R, K25Q |
| 167 | GIGAILKVLSTGLPALISWKRKRQE | A10S, T15A, N22R, K25Q, Q26E |
| 168 | GIGAVLKVLTTGLPALIGWIKRKRQQ | I5V, A10T, T15A, S18G, N22R, K25Q |
| 169 | GIGAVLKVLATGLPALISWIKRKRQQ | I5V, T15A, N22R, K25Q |
| 170 | GIGAVLKVLSTGLPALISWIKRKRQQ | I5V, A10S, T15A, N22R, K25Q |
| 171 | GIGAILRVLATGLPTLISWIKRKRKQ | K7R |
| 172 | GIGAILKVLATGLPTLISWIKKKKQQ | N22R |
| 173 | GIGAILKVLATGLPTLISWIKKKQQ | N22K, R24K, K25Q |
| 174 | GIGAILKVLATGLPTLISWIKNKRKQGSKKKK | Mel-GSKKKK |
| 175 | KKGIGAILKVLATGLPTLISWIKNKRKQ | KK-Mel |
| 176 | GIGAILEVLATGLPTLISWIKNKRKQ | K7E Mel |

Fig. 6D

Table 6E. MLP peptide sequences, continued.

| | | |
|---|---|---|
| 177 | GIGAVLKVLTTGLPALISWIKRKR | I5V, T15A, N22R, 25-26Δ |
| 178 | GIGAVLKVLTTGLPALISWIKR | I5V, T15A, N22R, 23-26Δ |
| 179 | CIGAVLKVLTTGLPALISWIKRKRQQ | G1C, I5L, T15A, N22R |
| 180 | QQRKRKIWSILAPLGTTLVKLVAGIG | I5V, A10T, T15A, N22R retroMel |
| 181 | QQRKRKIWSILAPLGTTLVKLVAGIC | G1C, I5V, A10T, T15A, N22R retroMel |
| 182 | QQKKKKIWSILAPLGTTLVKLVAGIC | G1C, I5V, A10T, T15A, N22R, R24K retroMel |
| 183 | QKRKNKIWSILTPLGTALVKLIAGIG | Q25K reverse Mel |
| 184 | QQRKRKIWSILAALGTTLVKLVAGIC | G1C, I5V, A10T, P14A, T15A, N22R retroMel | dMel = Melittin peptide having D-form amino acids

FIG. 6E

COMPOSITIONS AND METHODS FOR INHIBITING GENE EXPRESSION OF ALPHA-1 ANTITRYPSIN

BACKGROUND OF THE INVENTION

Alpha-1 antitrypsin deficiency is an inherited autosomal codominant genetic disorder that causes defective production of alpha 1-antitrypsin (A1AT) leading to lung and liver diseases and occurs with frequency about 1 case in 1,500 to 3,500 individuals. Alpha-1 antitrypsin deficiency most often affects persons with European ancestry worldwide.

Alpha-1 Antitrypsin (α1-antitrypsin, alpha-1 proteinase inhibitor. A1AT, or AAT) is a protease inhibitor belonging to the serpin superfamily. Normal AAT protein is primarily synthesized in the liver by hepatocytes and secreted into blood. Its physiologic function is to inhibit neutrophil proteases in order to protect host tissues from non-specific injury during periods of inflammation. The most clinically significant form of A1AT deficiency (AATD) is caused by the Z mutation. The Z mutant allele (PiZ), through a single point mutation, renders the mutant PiZ protein prone to abnormal folding in the endoplasmic reticulum of hepatocytes causing intracellular retention. The absence of circulating anti-protease activity leaves the lung vulnerable to injury by neutrophil elastase, resulting in the development of emphysema. Weekly use of AAT augmentation therapy for AATD, using purified human AAT, results in normal plasma levels of AAT and prevents lung damage in affected individuals.

While administration of purified AAT ameliorates lung damage caused by the absence of endogenously secreted AAT, AATD patients remain vulnerable to endoplasmic reticulum liver storage disease caused by the deposition of excessive abnormally folded AAT protein. Twelve to fifteen percent of patients with AATD also develop liver disease, which can be severe or fatal, even in infancy. The intracellular accumulation in hepatocytes of AAT protein in AATD patients induces liver cell damage and death, and chronic liver injury. Clinical presentations include chronic hepatitis, cirrhosis, hepatocellular carcinoma, transaminitis, cholestasis, fibrosis, and even fulminant hepatic failure.

There is currently no specific treatment to prevent the onset or slow the progression of liver disease due to AATD. Because liver damage resulting from AATD occurs through a gain-of-function mechanism, inhibition or AAT gene expression would be useful in preventing accumulation of the AAT protein in the liver, thereby providing a therapeutic treatment for AATD. Double-stranded RNA molecules (dsRNA) and other RNAi triggers have been shown to block gene expression in a highly conserved regulatory mechanism known as RNA interference (RNAi). The invention provides AAT RNA interference (RNAi) triggers and compositions thereof for inhibiting the expression of the AAT gene in vivo. The invention also provides methods of using the AAT RNAi triggers for treating AATD and conditions and diseases caused by AATD, such as chronic hepatitis, cirrhosis, hepatocellular carcinoma, and fulminant hepatic failure.

SUMMARY OF THE INVENTION

The invention provides alpha-1 antitrypsin (AAT) gene specific RNA interference (RNAi) trigger molecules able to selectively and efficiently decrease expression of AAT. The use of AAT RNAi trigger provides a method for the therapeutic treatment of diseases associated with alpha-1 antitrypsin deficiency. Such methods comprise administration of RNAi trigger targeting AAT to a human being or animal.

In one embodiment, the invention provides RNAi trigger molecules for inhibiting expression of the human AAT gene. The RNAi trigger comprises at least two sequences that are partially, substantially, or fully complementary to each other. In one embodiment, the two RNAi trigger sequences comprise a sense strand comprising a first sequence and an antisense strand comprising a second sequence. In another embodiment, the two RNAi trigger sequences comprise two sense strands which together comprise a first sequence and an antisense strand comprising a second sequence, wherein the sense strands and the antisense strand together form a meroduplex (Tables 2 and 4). The AAT RNAi trigger sense strands comprise sequences which have an identity of at least 90% to at least a portion of an AAT mRNA. Exemplary AAT RNAi trigger sense strands, antisense strands, sequence pairs and meroduplexes are shown in Tables 1-5.

In one embodiment, the antisense strand comprises a nucleotide sequence which is complementary to a part of an mRNA encoded by said AAT gene, and the region of complementarity is most preferably less than 30 nucleotides in length. Furthermore, it is preferred that the length of the herein described inventive RNAi triggers (duplex length) is in the range of about 16 to 30 nucleotides, in particular in the range of about 18 to 28 nucleotides. Particularly useful in context of this invention are duplex lengths of about 17, 18, 19, 20, 21, 22, 23 or 24 nucleotides. The sense and antisense strands can be the same length or they can be different lengths. For example, both the sense and antisense strands can be 19, 20, 21, 22, 23, or 24 nucleotides in length. As an example, the sense strand can be 21 nucleotides in length while the antisense strand is 23 nucleotides in length. Most preferred are duplex stretches of 19, 21, 22, or 23 nucleotides. The RNAi trigger, upon delivery to a cell expressing the AAT gene, inhibits the expression of said AAT gene in vitro or in vivo.

The RNAi trigger molecules or pharmaceutical compositions described herein can be administered in a number of ways depending upon whether local or systemic treatment is desired and upon the area to be treated. Administration can be topical (e.g., by a transdermal patch), pulmonary, e.g., by inhalation or insufflation of powders or aerosols, including by nebulizer: intratracheal, intranasal, epidermal and transdermal, oral or parenteral. Parenteral administration includes intravenous, intraarterial, subcutaneous, intraperitoneal or intramuscular injection or infusion; subdermal, e.g., via an implanted device; or intracranial, e.g., by intraparenchymal, intrathecal or intraventricular, administration.

The RNAi trigger molecules described herein can be delivered to target cells or tissues using any known oligonucleotide delivery technology known in the art. Nucleic acid delivery methods include, but not limited to, encapsulation in liposomes, by iontophoresis, or by incorporation into other vehicles, such as hydrogels, cyclodextrins, biodegradable nanocapsules, and bioadhesive microspheres, proteinaceous vectors or DPCs (WO 2000/053722, WO 2008/0022309, WO 2011/104169, and WO 2012/083185, each of which is incorporated herein by reference). In one embodiment, the AAT RNAi trigger is provided with an in vivo delivery compound. A preferred in vivo delivery compound comprises an MLP delivery polymer.

In another preferred embodiment, the invention features a composition for delivering an AAT RNAi trigger to a liver cell in vivo comprising: an AAT RNAi trigger described herein conjugated to a hydrophobic group containing at least 20 carbon atoms (RNA trigger-conjugate), such as a cholesterol.

BRIEF DESCRIPTION OF THE DRAWINGS

FIG. 1. Table 1. Core sequences of RNAi triggers targeting AAT mRNA.

FIG. 2 Table 2. RNAi trigger sequences containing 5' and 3' extensions. Letters in capitals represent ribonucleotides, lower case letters "c", "g", "a" and "u" represent 2' O-methyl-modified nucleotides, upper case letters A, C, G, U followed by "f" indicates a 2'-fluoro nucleotide, "s" represents phosphorothioate, "dT" represents deoxythymidine, (invdT) represents an inverted deoxythimidine (3'-3'-linked).

FIG. 3. Table 3. Canonical AAT siRNA. RNAi triggers. Letters in capitals represent RNA nucleotides, lower case letters "c", "g", "a" and "u" represent 2' O-methyl-modified nucleotides, upper case letters A, C, G, U followed by "f" indicates a 2'-fluoro nucleotide, "s" represents phosphorothioate, "dT" represents deoxythymidine, and (invdT) represents an inverted deoxythimidine (3'-3'-linked). $T_m$ is the melting temperature of the RNAi trigger.

FIG. 4. Table 4. AAT meroduplex RNAi triggers. Letters in capitals represent RNA nucleotides, lower case letters "c", "g", "a" and "u" represent 2' O-methyl-modified nucleotides, upper case letters A, C, G, U followed by "f" indicates a 2'-fluoro nucleotide, "s" represents phosphorothioate, "dT" represents deoxythymidine, and (invdT) represents an inverted deoxythimidine (3'-3'-linked). $T_m$ is the melting temperature of the RNAi trigger.

FIG. 5. Table 5. AAT UNA RNAi triggers. Letters in capitals represent RNA nucleotides, lower case letters "c", "g", "a" and "u" represent 2' O-methyl-modified nucleotides, upper case letters A, C, G, U followed by "f" indicates a 2'-fluoro nucleotide, upper case letters A, C, G, U followed by "$_{UNA}$" indicates an 2',3'-seco (unlocked) RNA nucleotide mimic, "s" represents phosphorothioate, "dT" represents deoxythymidine, and (invdT) represents an inverted deoxythimidine (3'-3'-linked). $T_m$ is the melting temperature of the RNAi trigger.

FIG. 6A-E. Table listing MLP polymers suitable for use in delivery of AAT RNAi triggers described herein in vivo.

DETAILED DESCRIPTION OF THE INVENTION

Figure 7:
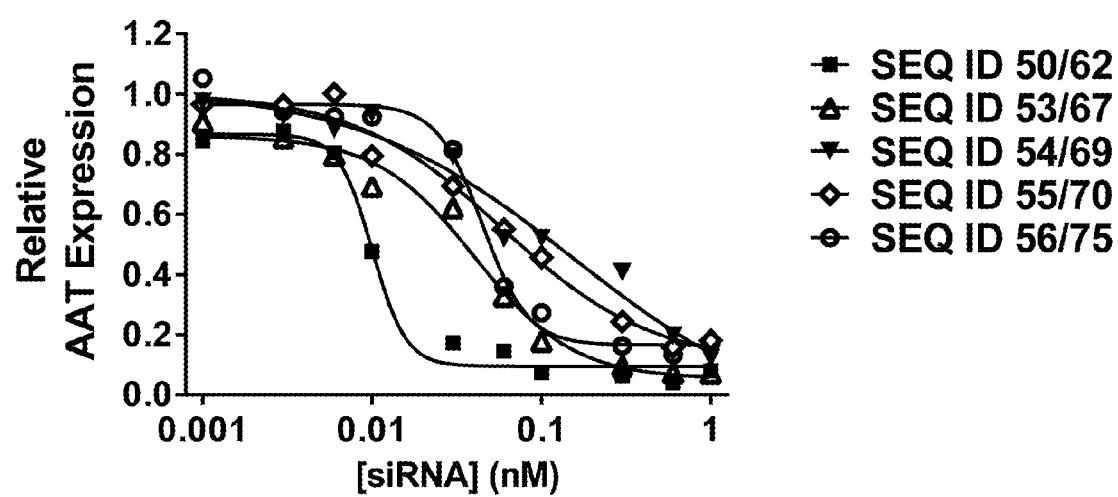
FIG. 7. Graph depicting relative AAT expression in Hep3B cells in vitro using varying concentrations of the indicated RNAi triggers.

Appended Tables 1-5 relate to preferred molecules and sequences to be used in forming AAT RNAi trigger molecules in accordance with the invention. An AAT RNAi trigger molecule described herein comprises one or two sense strands and an antisense strand each containing a core sequence of about 18 nucleobases. The antisense strand core sequence is complementary to a nucleotide sequence (target sequence) present in the AAT mRNA. The sense strand core sequence can be the same length as the antisense core sequence or it can be a different length. The sense and antisense core sequences of the RNAi triggers anneal to form a complementary duplex region or double helical structure. Within the complementary duplex region, the sense strand core sequence is at least 90% complementary or 100% complementary to the antisense core sequence. For meroduplex RNAi triggers, the sense strand core sequence is internally nicked, and two sense strand sequences are provided that together hybridize with the antisense strand core sequence. In addition, the sense strands and antisense strands may independently contain extensions of 1-6 nucleobases at the 5' ends of their core sequences, 3' ends of their core sequences, or both the 5' and 3' ends of their core sequences. The antisense strand extensions, if present, may or may not be complementary to the corresponding nucleotides for the AAT mRNA or to any corresponding nucleotides of the sense strand. Similarly, sense strand extensions, if present, may or may not be identical to the corresponding nucleotides for the AAT mRNA or to any corresponding nucleotides of the antisense strand. When delivered to a cell, the AAT RNAi triggers described herein "knockdown" or inhibit expression of the normal or Z mutant allele AAT gene.

The described AAT RNAi triggers and methods can be used to treat a subject having a disease or disorder that would benefit from reduction or inhibition in AAT expression. The subject is administered a therapeutically effective amount of any one or more of the described AAT RNAi triggers. Treatment of a subject that would benefit from a reduction and/or inhibition of AAT gene expression includes therapeutic and/or prophylactic treatment. The subject can be a human, patient, or human patient. The described AAT RNAi trigger molecules can be used to provide a method for the therapeutic treatment of diseases associated with mutant AAT expression. Such methods comprise administration of RNAi trigger targeting AAT to a human being or animal.

AAT RNAi trigger sense and antisense strand core sequences are shown in Table 1. Table 2 provides for illustrative examples of RNAi trigger sense and antisense strands described herein having 5' or 3' extensions. RNAi trigger sense and antisense strands having modified nucleotides are provided herein and are in particular disclosed in appended Tables 3-5, providing illustrative examples of modified RNAi trigger sense and antisense strands of the present invention. The relation of the modified RNAi trigger strands shown in Tables 2-5 to the unmodified core sequences shown in Table 1 are indicated by the core SEQ ID numbers. The modifications of these constituents of the inventive RNAi triggers are provided herein as examples of modifications and/or modification patterns.

RNAi triggers (also called dsRNAi triggers) inhibit gene expression through the biological process of RNA interference (RNAi). RNAi triggers comprise double stranded RNA or RNA-like structures typically containing 15-50 base pairs and preferably 18-26 base pairs and having a nucleobase sequence at least 90% complementary to a coding sequence in an expressed target gene within the cell. RNAi triggers include, but are not limited to: short interfering RNAs (siRNAs), double-strand RNAs (dsRNA), micro RNAs (miRNAs), short hairpin RNAs (shRNA), and dicer substrates (U.S. Pat. No. 8,084,599 8,349,809 and 8,513,207).

An RNAi trigger described here is formed by annealing an antisense strand with a sense strand, for canonical siRNA RNAi triggers and UNA RNAi triggers, or two sense strands, for meroduplex RNAi triggers. In a preferred embodiment, the AAT RNAi trigger antisense strands comprise nucleic acid sequences depicted in SEQ ID Nos: 1, 2, 3, 4, and 5. The corresponding AAT RNAi trigger sense strands comprise nucleic acid sequences depicted in SEQ ID Nos: 8, 9, 10, 11, and 12. Accordingly, the inventive AAT RNAi trigger molecules may, inter alia, comprise the sequence pairs selected from the group consisting of SEQ ID pairs: 1/8, 2/9, 3/10, 4/11, and 5/12. Complementary pairs or meroplexes (RNAi triggers) are provided in Tables 1-5 as indicated by SEQ ID pair or SEQ ID mero.

As detailed below, the herein described RNAi trigger molecule sense strands and antisense strands each comprises a core sequence and optionally a 5' extension, a 3' extension, or a 5' extension and a 3' extension. As used herein, an extension comprises 1-5 nucleotides at the 5' or 3' end of the sense strand core sequence or antisense strand core sequence. The extension nucleotides on a sense strand may or may not be complementary to (base pair with) nucleotides, either core sequence nucleotides of extension nucleotides, in the corresponding antisense strand. Conversely, the extension nucleotides on an antisense strand may or may not be complementary to (base pair with) nucleotides, either core sequence nucleotides of extension nucleotides, in the corresponding sense strand.

In one embodiment an AAT RNAi trigger molecule described herein comprises an antisense strand with a 3' extension of 1-5 nucleotides in length, preferably 1-2 nucleotides in length. In one embodiment, one or more of the antisense strand extension nucleotides comprise uracil or thymidine nucleotides or nucleotides which are complementary to the corresponding AAT mRNA sequence. In another embodiment, the antisense strand extension consists of dTdT or dTsdT, wherein dT represents a deoxythimidine nucleotide and sdT represents a deoxythimidine nucleotide having a 5' phosphorothioate.

In another preferred embodiment, an AAT RNAi trigger molecule described herein comprises a sense strand with a 3' extension of 1-5 nucleotides in length, preferably 1-2 nucleotides in length. In one embodiment, one or more of the antisense strand extension nucleotides comprises adenosine, uracil, or thymidine nucleotides, AT dinucleotide, or nucleotides which correspond to nucleotides in the AAT mRNA sequence. In a preferred embodiment, the 3' sense strand extension consists of Af(invdT), wherein Af represents a 2'-fluoro Adenosine nucleotide and invdT represents an inverted (3'-3'-linked) deoxythimidine nucleotide.

In one embodiment, an AAT RNAi trigger molecule described herein comprises an antisense strand with a 5' extension of 1-5 nucleotides in length, preferably 1-2 nucleotides in length. In one embodiment, one or more of the antisense strand extension nucleotides comprises uracil or thymidine nucleotides or nucleotides which are complementary to the corresponding AAT mRNA sequence. In a preferred embodiment, the antisense strand extension consists of dT.

In another preferred embodiment, an AAT RNAi trigger molecule described herein comprises a sense strand with a 5' extension of 1-5 nucleotides in length, preferably 1-3 nucleotides in length. In one embodiment, one or more of the sense strand extension nucleotides comprise uracil or adenosine nucleotides or nucleotides which correspond to nucleotides in the AAT mRNA sequence, In a preferred embodiment, the sense strand extension consists of 5' UAU or 5' uAu, wherein u represents a 2' O-methyl-modified uridine nucleotide.

RNAi trigger molecules described herein may contain 3' and/or 5' extensions independently on each of the sense strands and antisense strands. In one embodiment, both the sense strands and the antisense strands contain 3' and 5' extensions, each as described above. In one embodiment, one or more of the 3' extension nucleotides of one strand base pairs with one or more 5' extension nucleotides of the other strand. In another embodiment, the one or more of the 3' extension nucleotides of one strand do not base pair with the one or more 5' extension nucleotides of the other strand. The sense and antisense strands of an RNAi trigger may or may not contain the same number of nucleotide bases. The antisense and sense strands may form a duplex wherein the 5' end only has a blunt end, the 3' end only has a blunt end, both the 5' and 3' ends are blunt ended, or neither the 5' end nor the 3' end are blunt ended. In another embodiment, one or more of the nucleotides in the extension contains a thiophosphate, phosphorothioate, deoxynucleotide inverted (3' to 3' linked) nucleotide or is a modified ribonucleotide or deoxynucleotide.

In some embodiments the sense and antisense strands of the herein described RNAi triggers contain different numbers of nucleotide bases. In some embodiments, the sense strand 5' end and the antisense strand 3' end of a herein described RNAi trigger form a blunt end. In some embodiments, the sense strand 3' end and the antisense strand 5' end of a herein described RNAi trigger form a blunt end. In some embodiments, the both ends of a herein described RNAi trigger form a blunt end. In some embodiments, neither end of a herein described RNAi trigger is blunt ended. As used herein a blunt end refers to an end of a double stranded trigger molecule in which the terminal nucleotides of the two annealed strands are complementary (form a complementary base-pair). In some embodiments, the sense strand 5' end and the antisense strand 3' end of a herein described RNAi trigger form a frayed end. In some embodiments, the sense strand 3' end and the antisense strand 5' end of a herein described RNAi trigger form a frayed end. In some embodiments, the both ends of a herein described RNAi trigger form a frayed end. In some embodiments, neither end of a herein described RNAi trigger is a frayed end. As used herein a frayed end refers to an end of a double stranded trigger molecule in which the terminal nucleotides of the two annealed strands are not complementary (i.e. form a non-complementary base-pair). As used herein, an overhang is a stretch of one or more unpaired nucleotides at the end of one strand of a double strand RNAi trigger molecule. The unpaired nucleotides may be on the sense strand or the antisense strand, creating either 3° or 5° overhangs. In some embodiments the RNAi trigger molecule contains: a blunt end and a frayed end, a blunt end and 5' overhang end, a blunt end and a 3' overhang end, a frayed end and a 5' overhand end, a frayed end and a 3' overhang end, two 5' overhang ends, two 3' overhang ends, or a 5' overhang end and a 3' overhand end.

In one preferred embodiment the inventive AAT RNAi trigger molecules comprise sequence pairs selected from the group consisting of SEQ ID NOs: 15/23, 15/24, 16/28, 17/30, 18/31, 19/36, and 19/38. In another preferred embodiment the inventive AAT mero RNAi trigger molecules comprise meroduplexes selected from the group consisting of SEQ ID NOs: 15/25/41, 15/26/42, 15/27/43, 16/29/44, 18/32/45, 18/33/46, 18/34/47, 18/35/48, and 19/37/49.

RNAi triggers (also called dsRNAi triggers) inhibit gene expression through the biological process of RNA interference (RNAi). RNAi triggers comprise double stranded RNA or RNA-like structures typically containing 15-50 base pairs and preferably 18-25 base pairs and having a nucleobase sequence identical (perfectly complementary) or nearly identical (substantially complementary) to a coding sequence in an expressed target gene within the cell. RNAi triggers include, but are not limited to: short interfering RNAs (siRNAs), double-strand RNAs (dsRNA), micro RNAs (miRNAs), short hairpin RNAs (shRNA), meroduplexes, unlocked nucleic acid-containing dsRNAs, and dicer substrates (U.S. Pat. No. 8,084,599 8,349,809 and 8,513,207).

The AAT RNAi trigger molecules described herein may be comprised of naturally occurring nucleotides or may be comprised of at least one modified nucleotide or nucleotide mimic. The RNAi trigger sense and antisense strands described herein may be synthesized and/or modified by methods well established in the art.

A nucleotide base (or nucleobase) is a heterocyclic pyrimidine or purine compound which is a constituent of all nucleic acids and includes adenine (A), guanine (G), cytosine (C), thymine (T), and uracil (U). A nucleoside is a ribosyl or deoxyribosyl derivative of certain pyrimidine or purine bases. They are thus glycosylamines or N-glycosides related to nucleotides by the lack of phosphorylation. It has also become customary to include among nucleosides analogous substances in which the glycosyl group is attached to carbon rather than nitrogen ('C-nucleosides'). A nucleotide is a compound formally obtained by esterification of the 3' or 5' hydroxy group of nucleosides with phosphoric acid. They are the monomers of nucleic acids.

As used herein, "G," "C," "A", "U" and "T" or "dT" respectively, each generally stand for a nucleobase, nucleoside, nucleotide or nucleotide mimic that contains guanine, cytosine, adenine, uracil and deoxythymidine as a base, respectively. Also, as used herein, the term "ribonucleotide" or "nucleotide" can also refer to a modified nucleotide or nucleotide mimic, as further detailed below, or a surrogate replacement moiety. Sequences comprising such replacement moieties are embodiments described herein.

For RNAi trigger molecules described herein, the nucleosides, or nucleotide bases, may be linked by phosphate-containing (natural) or non-phosphate-containing (non-natural) covalent internucleoside linkages, i.e. the RNAi trigger molecules may have natural or non-natural oligonucleotide backbones. In another embodiment, the RNAi trigger contains a non-standard (non-phosphate) linkage between two nucleotide bases.

In a preferred embodiment, one of more nucleotides of the RNAi trigger molecules are modified nucleotides. In another embodiment, at least 50%, at least 60%, at least 70%, at least 80%, at least 90%, at least 95%, or 100% of the nucleotides are modified. Modified nucleotides include, but are not limited to: 2' modifications, 2'-O-methyl nucleotide (represented herein as a lower case letter 'n' in a nucleotide sequence), 2'-deoxy-2'-fluoro nucleotide (represented herein as Nf, also represented herein as 2' fluoro nucleotide), 2'-deoxy nucleotide (represented herein as dN), 2'-amino nucleotide, 2'-alkyl nucleotide, terminal 3' to 3' linkages, inverted deoxythymidine (represented herein as invdT), a nucleotide comprising a 5'-phosphorothioate group (represented herein as a lower case 's' before a nucleotide, as in sN), thiophosphate linkages, phosphorodithioate group, non-natural base comprising nucleotide, locked nucleotides, bridged nucleotides, peptide nucleic acids, 2',3'-seco nucleotide mimic (unlocked nucleotide, represented herein as $N_{UNA}$), morpholino nucleotides, and abasic nucleotide. It is not necessary for all positions in a given compound to be uniformly modified. Conversely, more than one modification may be incorporated in a single RNAi trigger compound or even in a single nucleotide thereof. Ribose 2' modification may be combined with modified nucleoside linkages.

Preferred modified internucleoside linkages or backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkyl-phosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or to 5'-2'. Various salts, mixed salts and free-acid forms are also included.

Preferred modified internucleoside linkages or backbones that do not include a phosphorus atom therein (i.e., oligonucleosides) have backbones that are formed by short chain alkyl or cycloalkyl inter-sugar linkages, mixed heteroatom and alkyl or cycloalkyl inter-sugar linkages, or one or more short chain heteroatomic or heterocyclic inter-sugar linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

In another embodiment, the AAT RNAi trigger molecules described herein are canonical siRNAs having modified nucleotides. Exemplary sequences suitable for forming AAT canonical siRNA RNAi triggers having modified nucleotides are shown in Table 3. Exemplary AAT canonical siRNA RNAi triggers are SEQ ID pairs: 50/62, 50/63, 53/67, 54/69, 55/70, 56/75, and 56/77.

In another embodiment, the AAT RNAi trigger molecules described herein are meroduplexes having modified nucleotides. Exemplary sequences suitable for forming AAT meroduplex RNAi triggers having modified nucleotides are shown in Table 4. Exemplary AAT meroduplex RNAi triggers are SEQ ID meroplexes: 50/64/81, 50/65/82, 50/66/83, 53/68/84, 55/71/85, 55/72/86, 55/73/87, 55/74/88, and 56/76/89.

The AAT RNAi trigger antisense strand preferably contains at least one "unlocked nucleotide" (UNA), AAT UNA RNAi trigger. UNA is an acyclic-RNA mimic also known as 2',3'-seco-RNA, wherein the C2'-C3' ribose bond is absent. Because the ribose 2',3' bond is absent, UNAs are flexible, enabling modulation of affinity and specificity. UNA exhibit decreased binding affinity towards a complementary strand resulting in a decrease in the thermostability of the duplex. A UNA may be located anywhere along a base strand of an RNAi trigger. RNAi triggers described herein preferably contain a UNA located at position 6 or 7 (numbering included the 5' dT nucleotide extension). Exemplary sequences suitable for forming AAT UNA RNAi triggers are shown in Table 5. Exemplary AAT UNA RNAi triggers are SEQ ID pairs: 51/63, 52/63, 57/77, and 58/77.

Modified nucleobases include other synthetic and natural nucleobases, such as 5-substituted pyrimidines, 6-azapyrimidines and N-2, N-6 and O-6 substituted purines, including 2-aminopropyladenine, 5-propynyluracil and 5-propynylcytosine, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine.

In one embodiment, AAT RNAi triggers described herein comprise a targeting moiety conjugated to the RNAi trigger. We have found that conjugation of an RNAi trigger to a targeting moiety, wherein the targeting moiety comprises a hydrophobic group or to a galactose cluster, facilitates in vivo targeting of the RNAi trigger to the liver. A RNAi trigger-targeting moiety conjugate is formed by covalently linking the RNAi trigger to the targeting moiety. The targeting moiety may be linked to the 3' or the 5' end of the RNAi trigger sense strand or antisense strand. The targeting moiety is preferably linked to the RNAi trigger sense strand 5' end.

In one embodiment, the targeting moiety consists of a hydrophobic group. More specifically, the RNAi trigger targeting moiety consists of a hydrophobic group having at least 20 carbon atoms. Hydrophobic groups used as targeting moieties are herein referred to as hydrophobic targeting moieties. Hydrophobic targeting moieties are preferably hydrocarbons, containing only carbon and hydrogen atoms. However, substitutions or heteroatoms which maintain hydrophobicity, for example fluorine, may be permitted. Hydrophobic groups useful as targeting moieties may be selected from the group consisting of: alkyl group, alkenyl group, alkynyl group, aryl group, aralkyl group, aralkenyl group, and aralkynyl group, each of which may be linear, branched, or cyclic, cholesterol, cholesterol derivative, sterol, steroid, and steroid derivative. Exemplary suitable hydrophobic groups may be selected from the group comprising: cholesterol, cholesterol derivatives, dicholesterol, tocopherol, ditocopherol, didecyl, didodecyl, dioctadecyl, didodecyl, dioctadecyl, isoprenoid, and choleamide.

In another embodiment, the targeting moiety comprises a galactose targeting moiety or galactose cluster targeting moiety. As used herein, a galactose cluster comprises a molecule having two to four, often three, terminal galactose derivatives. As used herein, the term galactose derivative includes both galactose and derivatives of galactose having affinity for the asialoglycoprotein receptor equal to or greater than that of galactose. Galactose or galactose clusters useful for targeting oligonucleotides and other molecules to the liver in vivo are well known in the art.

Other terms common in the art include tri-antennary galactose, tri-valent galactose and galactose trimer. A preferred galactose derivative is an N-acetyl-galactosamine (GalNAc). Other saccharides having affinity for the asialoglycoprotein receptor may be selected from the list comprising: galactose, galactosamine, N-formylgalactosamine, N-acetylgalactosamine, N-propionyl-galactosamine, N-n-butanoylgalactosamine, and N-iso-butanoylgalactos-amine.

In one embodiment a targeting moiety is conjugated to the 5' end of an AAT RNAi trigger sense strand. In another preferred embodiment, the targeting moiety is conjugated to the 5' end of an AAT RNAi trigger sense strand having a UAU extension. A preferred targeting moiety is a cholesteryl derivative. A preferred UAU extension is a uAu extension. In yet another embodiment, the cholesteryl derivative is linked to the 5' end of the AAT RNAi trigger sense strand via a linker. Exemplary linkers include alkyl groups and PEG groups. A preferred PEG linker is a triethylene glycol linkage.

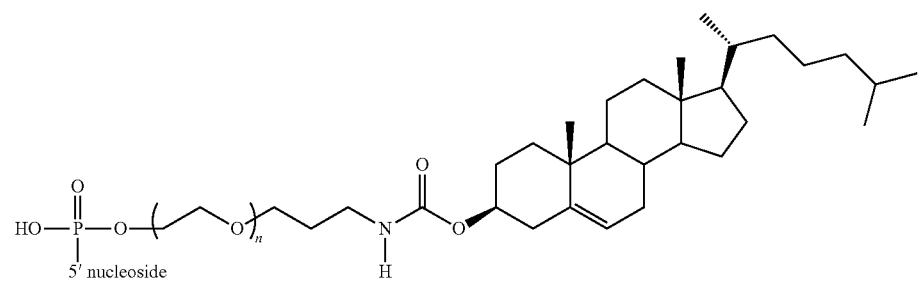

Chol-PEG targeting moiety (n = 1-10)

Exemplary AAT RNAi triggers having cholesteryl targeting moieties include: SEQ ID pairs or meroduplexes: 50/63, 56/77, 50/64/81, 50/65/82, 50/66/83, 53/68/84, 55/71/85, 55/72/86, 55/73/87, 55/74/88, 56/76/89, 51/63, 52/63, 57/77, and 58/77.

The RNAi trigger molecules described herein may be synthesized having a reactive group, such as an amine group, at the 5'-terminus. The reactive group may be used to subsequently attach a targeting moiety using methods typical in the art.

As used herein, the term "sequence" refers to a chain of nucleotides that is described by the sequence referred to using the standard nucleotide nomenclature. However, as detailed herein, such a "strand comprising a sequence" may also comprise modifications, like modified nucleotides and nucleotide mimics.

As used herein, and unless otherwise indicated, the term "complementary," when used to describe a first nucleotide sequence (e.g. RNAi trigger sense strand or AAT mRNA) in relation to a second nucleotide sequence (e.g. RNAi trigger antisense strand), refers to the ability of an oligonucleotide or polynucleotide comprising the first nucleotide sequence to hybridize and form a duplex or double helical structure under certain conditions with an oligonucleotide or polynucleotide comprising the second nucleotide sequence. Complementary sequences include Watson-Crick base pairs or non-Watson-Crick base pairs and include natural or modified nucleotides or nucleotide mimics in as far as the above requirements with respect to their ability to hybridize are fulfilled. Perfectly or fully complementary means that all the bases in a contiguous sequence of a first polynucleotide will hybridize with the same number of bases in a contiguous sequence of a second polynucleotide. The contiguous sequence may comprise all or a part of the first or second nucleotide sequence. Partial complementary means that in a hybridized pair of nucleobase sequences there are one or more mismatched base pairs. Substantial complementary, as used here when referring to the RNAi triggers described herein means that in a hybridized pair of nucleobase sequences 1-3 mismatched base pair. The terms "complementary", "fully complementary" and "substantially complementary" herein may be used with respect to the base matching between the sense strand and the antisense strand of an RNAi trigger, or between the antisense strand of a RNAi trigger and a sequence of the AAT mRNA.

We describe compositions and methods for inhibiting expression of AAT in a cell, group of cells, tissue, or subject, comprising: administering to the subject a therapeutically effective amount of a herein described AAT RNAs trigger thereby inhibiting the expression of AAT in the subject. Silence, reduce, inhibit, down-regulate, or knockdown gene expression, in as far as they refer to an AAT gene, means that the expression of the gene, as measured by the level of RNA transcribed from the gene or the level of polypeptide, protein or protein subunit translated from the mRNA in a cell, group of cells, tissue, or subject in which the AAT gene is transcribed, is reduced when the cell, group of cells, tissue, or subject is treated with AAT RNAi triggers described herein as compared to a second cell, group of cells, tissue, or subject but which has or have not been so treated.

Furthermore, the invention relates to a method for inhibiting expression of the AAT gene in a cell, tissue or organism comprising the steps of: introducing into the cell, tissue or organism an RNAi trigger as defined herein; and maintaining said cell, tissue or organism for a time sufficient to obtain degradation of the mRNA transcript of AAT, thereby inhibiting expression of AAT in a given cell.

In some embodiments, we describe pharmaceutical compositions comprising at least one of the described AAT RNAi triggers. These pharmaceutical compositions are particularly useful in the inhibition of the expression of the AAT gene in a cell, a tissue, or an organism. The described pharmaceutical compositions can be used to treat a subject having a disease or disorder that would benefit from reduction or inhibition in AAT expression. The described pharmaceutical compositions can be used to treat a subject at risk of developing a disease or disorder that would benefit from reduction or inhibition in AAT expression. Diseases and/or disorder that would benefit from reduction or inhibition in AAT expression may be selected from the list comprising: AATD, chronic hepatitis, cirrhosis, hepatocellular carcinoma, and fulminant hepatic failure. Preferably, the subject is a mammal, most preferably a human patient. In one embodiment, the method comprises administering a composition comprising an AAT RNAi trigger molecule described herein to a mammal to be treated. The pharmaceutical compositions described above may also comprise a one or more pharmaceutically acceptable excipient (including vehicles, carriers, diluents, and/or delivery polymers).

In another embodiment, the invention provides methods for treating, preventing or managing clinical presentations associated with AATD including, AATD. Said methods comprise administering to a subject in need of such treatment, prevention or management a therapeutically or prophylactically effective amount of one or more of the AAT RNAi triggers described herein. Preferably, said subject is a mammal, most preferably a human patient. In one embodiment, the method comprises administering a composition comprising an AAT RNAi trigger molecule described herein to a mammal to be treated.

The terms "treat", "treatment", and the like, mean in context of this invention the relief from or alleviation of a disorder related to AATD.

The described AAT RNAi triggers and methods can be used to treat or prevent at least one symptom in a subject having a disease or disorder that would benefit from reduction or inhibition in AAT expression. The subject is administered a therapeutically effective amount of any one or more of the described RNAi triggers thereby treating the symptom. The subject is administered a prophylactically effective amount of any one or more of the described RNAi triggers thereby preventing the at least one symptom.

In some embodiments, the gene expression level and/or mRNA level of AAT in a subject to whom a described AAT RNAi trigger is administered is reduced by at least about 5%, 10%, 15%, 20%, 25%, 30%, 35%, 40%, 45%, 50%, 55%, 60%, 65%, 70%, 75%, 80%, 85%, 90%, 95%, or 98% relative to the subject not receiving the AAT RNAi trigger. The gene expression level and/or mRNA level in the subject may be reduced in a cell, group of cells, and/or tissue of the subject. In some embodiments, the protein level of AAT in a subject to whom a described AAT RNAi trigger is administered is reduced by at least about 5%, 10%, 15%, 20%, 25%, 30%, 35%, 40%, 45%, 50%, 55%, 60%, 65%, 70%, 75%, 80%, 85%, 90%, 95%, or 98% relative to the subject not receiving the RNAi trigger. The protein level in the subject may be reduced in a cell, group of cells, tissue, blood, and/or other fluid of the subject. Reduction gene expression, mRNA, or protein levels can be assessed by any methods known in the art. Reduction or decrease in AAT mRNA level and/or protein level are collectively referred to herein as a reduction or decrease in AAT or inhibiting or reducing the expression of AAT.

"Introducing into a cell", when referring to a RNAi trigger, means functionally delivering the RNAi trigger into a cell. By functional delivery, it is meant that the RNAi trigger is delivered to the cell and has the expected biological activity, sequence-specific inhibition of gene expression. Many molecules, including RNAi trigger molecules, administered to the vasculature of a mammal are normally cleared from the body by the liver. Clearance of a an RNAi trigger by the liver wherein the RNAi trigger is degraded or otherwise processed for removal from the body and wherein the RNAi trigger does not cause sequence-specific inhibition of gene expression is not considered functional delivery.

The route of administration is the path by which a RNAi trigger is brought into contact with the body. In general, methods of administering drugs and nucleic acids for treatment of a mammal are well known in the art and can be applied to administration of the compositions described herein. The compounds of the present invention can be administered via any suitable route in a preparation appropriately tailored to the particular route. Thus, the compounds of the present invention can be administered by injection, for example, intravenously, intramuscularly, intracutaneously, subcutaneously, or intraperitoneally. Accordingly, the present invention also provides pharmaceutical compositions comprising a pharmaceutically acceptable carrier or excipient.

The AAT RNAi trigger molecules or compositions described herein can be delivered to a cell, group of cells, tissue, or subject using oligonucleotide delivery technologies known in the art. In general, any suitable method recognized in the art for delivering a nucleic acid molecule (in vitro or in vivo) can be adapted for use with an RNAi trigger of the invention. For example, delivery can be by local administration, (e.g., direct injection, implantation, or topical administering), systemic administration, or subcutaneous, intravenous, oral, intraperitoneal, or parenteral routes, including intracranial (e.g., intraventricular, intraparenchymal and intrathecal), intramuscular, transdermal, airway (aerosol), nasal, rectal, or topical (including buccal and sublingual) administration, In certain embodiments, the compositions are administered by subcutaneous or intravenous infusion or injection.

The RNAi triggers can be combined with lipids, nanoparticles, polymers, liposomes, micelles, DPCs or other delivery systems available in the art. The RNAi triggers can also be chemically conjugated to targeting moieties, lipids (including, but not limited to cholesterol and cholesteryl derivative), nanoparticles, polymers, liposomes, micelles, DPCs (WO 2000/053722, WO 2008/0022309, WO 2011/104169, and WO 2012/083185, each of which is incorporated herein by reference), or other delivery systems available in the art.

As used herein, a "pharmaceutical composition" comprises a pharmacologically effective amount of at least one kind of RNAi trigger and a pharmaceutically acceptable carrier and optionally an excipient.one or more a pharmaceutically acceptable excipients. Pharmaceutically acceptable excipients (excipients) are substances other than the Active Pharmaceutical ingredient (API, therapeutic product, e.g., AAT RNAi trigger) that have been appropriately evaluated for safety and are intentionally included in the drug delivery system. Excipients do not exert or are not intended to exert a therapeutic effect at the intended dosage. Excipients may act to a) aid in processing of the drug delivery system during manufacture, b) protect, support or enhance stability, bioavailability or patient acceptability of the API, c) assist in product identification, and/or d) enhance any other attirbure of the overall safety, effectiveness, of delivery of the API during storage or use.

Excipients include, but are not limited to: absorption enhancers, anti-adherents, anti-foaming agents, anti-oxidants, binders, binders, buffering agents, carriers, coating agents, colors, delivery enhancers, dextran, dextrose, diluents, disintegrants, emulsifiers, extenders, fillers, flavors, glidants, humectants, lubricants, oils, polymers, preservatives, saline, salts, solvents, sugars, suspending agents, sustained release matices, sweeteners, thickening agents, tonicity agents, vehicles, water-repelling agents, and wetting agents. A pharmaceutically acceptable excipient may or may not be an inert substance.

The pharmaceutical compositions of the can contain other additional components commonly found in pharmaceutical compositions. The pharmaceutically-active materials may include, but are not limited to: anti-pruritics, astringents, local anesthetics, or anti-inflammatory agents (e.g., antihistamine, diphenhydramine, etc.). It is also envisaged that cells, tissues or isolated organs that express or comprise the herein defined RNAi triggers may be used as "pharmaceutical compositions". As used herein, "pharmacologically effective amount," "therapeutically effective amount," or simply "effective amount" refers to that amount of an RNAi trigger to produce the intended pharmacological, therapeutic or preventive result.

In one embodiment, the AAT RNAi trigger-targeting moiety conjugate is co-administered with an MLP delivery polymer (excipient). By co-administered it is meant that the AAT RNAi trigger and the delivery polymer are administered to the mammal such that both are present in the mammal at the same time. The AAT RNAi trigger-targeting moiety conjugate and the delivery polymer may be administered simultaneously or they may be delivered sequentially. For simultaneous administration, they may be mixed prior to administration. For sequential administration, either the AAT RNAi trigger-targeting moiety conjugate or the delivery polymer may be administered first.

In a preferred embodiment, the invention features a pharmaceutical composition for delivering an AAT RNAi trigger to a liver cell in vivo comprising: a) an AAT RNAi trigger conjugated to a hydrophobic group containing at least 20 carbon atoms (RNA trigger-conjugate), such as a cholesterol and b) an MLP delivery polymer. The MLP delivery polymer and the RNA trigger-conjugate are synthesized separately and may be supplied in separate containers or a single container. In a preferred embodiment, the AAT RNAi trigger is not conjugated to the delivery polymer.

MLP Delivery Polymer

Melittin-like peptide, MLP, as used herein, is a small amphipathic membrane active peptide, comprising about 23 to about 32 amino acids derived from the naturally occurring bee venom peptide, melittin, as described in WO 2012/083185. The naturally occurring melittin contains 26 amino acids and is predominantly hydrophobic on the amino terminal end and predominantly hydrophilic (cationic) on the carboxy terminal end. MLP described herein can be isolated from a biological source or it can be synthetic. A synthetic polymer is formulated or manufactured by a chemical process "by man" and is not created by a naturally occurring biological process. As used herein, MLP encompasses the naturally occurring bee venom peptides of the melittin family that can be found in, for example, venom of the species: *Apis florea, Apis mellifera, Apis cerana, Apis dorsata, Vespula maculifrons, Vespa magnifica, Vespa velutina, Polistes* sp. HQL-2001, and *Polistes hebraeus*. As used herein, MLP also encompasses synthetic peptides having amino acid sequence identical to or similar to naturally occurring melittin peptides. Exemplary MLP amino acid sequences include those shown in FIG. 6. In addition to the amino acids which retain melittin's inherent high membrane activity, 1-8 amino acids can be added to the amino or carboxy terminal ends of the peptide. Specifically, cysteine residues can be added to the amino or carboxy termini. The list in FIG. 1 is not meant to be exhaustive, as other conservative amino acid substitutions are readily envisioned. Synthetic MLPs can contain naturally occurring L form amino acids or the enantiomeric D form amino acids (inverso). However, a MLP should either contain essentially all L form or all D form amino acids but may have amino acids of the opposite stereocenter appended at either the amino or carboxy termini. The MLP amino acid sequence can also be reversed (retro). Retro MLP can have L form amino acids or D form amino acids (retroinverso). MLPs can have modifying groups, other than masking agents, that enhance tissue targeting or facilitate in vivo circulation attached to either the amino terminal or carboxy terminal ends of the peptide.

However, as used herein, MLP does not include chains or polymers containing more than two MLP peptides covalently linked to one another other or to another polymer or scaffold.

In one embodiment, a MLP comprises an *Apis florea* (little or dwarf honey bee) melittin, *Apis mellifera* (western or European or big honey bee), *Apis dorsata* (giant honey bee), *Apis cerana* (oriental honey bee) or derivatives thereof. A preferred MLP comprises the sequence: $Xaa_1$-$Xaa_2$-$Xaa_3$-Ala-$Xaa_5$-Leu-$Xaa_7$-Val-Leu-$Xaa_{10}$-$Xaa_{11}$-$Xaa_{12}$-Leu-Pro-$Xaa_{15}$-Leu-$Xaa_{17}$-$Xaa_{18}$-Trp-$Xaa_{20}$-$Xaa_{21}$-$Xaa_{22}$-$Xaa_{23}$-$Xaa_{24}$-$Xaa_{25}$-$Xaa_{26}$ wherein:

$Xaa_1$ is leucine, D-leucine, isoleucine, norleucine, tyrosine, tryptophan, valine, alanine, dimethylglycine, glycine, histidine, phenylalanine, or cysteine, $Xaa_2$ is isoleucine, leucine, norleucine, or valine, $Xaa_3$ is glycine, leucine, or valine, $Xaa_5$ is isoleucine, leucine, norleucine, or valine, $Xaa_7$ is lysine, serine, asparagine, alanine, arginine, or histidine, $Xaa_{10}$ is alanine, threonine, or leucine, $Xaa_{11}$ is threonine or cysteine, $Xaa_{12}$ is glycine, leucine, or tryptophan, $Xaa_{15}$ is threonine or alanine, $Xaa_{17}$ is isoleucine, leucine, norleucine, or valine, $Xaa_{18}$ is serine or cysteine, $Xaa_{20}$ is isoleucine, leucine, norleucine, or valine, $Xaa_{21}$ is lysine or alanine, $Xaa_{22}$ is asparagine or arginine, $Xaa_{23}$ is lysine or alanine, $Xaa_{24}$ is arginine or lysine, $Xaa_{25}$ is lysine, alanine, or glutamine, $Xaa_{26}$ is optional and if present is glutamine, cysteine, glutamine-$NH_2$, or cysteine-$NH_2$; and, and at least two of $Xaa_{21}$, $Xaa_{23}$, and $Xaa_{25}$ are lysine.

In another embodiment, MLP comprises the sequence: $Xaa_1$-$Xaa_2$-$Xaa_3$-Ala-$Xaa_5$-Leu-$Xaa_7$-Val-Leu-$Xaa_{10}$-$Xaa_{11}$-$Xaa_{12}$-Leu-Pro-$Xaa_{15}$-Leu-$Xaa_{17}$-Ser-Trp-$Xaa_{20}$-Lys-$Xaa_{22}$-Lys-Arg-Lys-$Xaa_{26}$ wherein:

$Xaa_1$ is leucine, D-leucine, norleucine, or tyrosine, $Xaa_2$ is isoleucine, leucine, norleucine, or valine, $Xaa_3$ is glycine, leucine, or valine, $Xaa_5$ is isoleucine, valine, leucine, or norleucine, $Xaa_7$ is lysine, serine, asparagine, alanine, arginine, or histidine, $Xaa_{10}$ is alanine, threonine, or leucine, $Xaa_{11}$ is threonine, or cysteine, $Xaa_{12}$ is glycine, leucine, or tryptophan, $Xaa_{15}$ is threonine, or alanine, $Xaa_{17}$ is isoleucine, leucine, or norleucine, $Xaa_{20}$ is isoleucine, leucine, or norleucine, $Xaa_{22}$ is asparagine or arginine, and $Xaa_{26}$ is glutamine or cysteine.

A another embodiment, MLP comprises the sequence: $Xaa_1$-$Xaa_2$-Gly-Ala-$Xaa_5$-Leu-Lys-Val-Leu-Ala-$Xaa_{11}$-Gly-Leu-Pro-Thr-Leu-$Xaa_{17}$-Ser-Trp-$Xaa_{20}$-Lys-$Xaa_{22}$-Lys-Arg-Lys-$Xaa_{26}$ wherein:

$Xaa_1$, $Xaa_2$, $Xaa_5$, $Xaa_{17}$ and $Xaa_{20}$ are independently isoleucine, leucine, or norleucine, $Xaa_{11}$ is threonine or cysteine, $Xaa_{22}$ is Asparagine or arginine, and $Xaa_{26}$ is glutamine or cysteine.

A another embodiment, MLP comprises: Leu-Ile-Gly-Ala-Ile-Leu-Lys-Val-Leu-Ale-Thr-Gly-Leu-Pro-Thr-Leu-Ile-Ser-Trp-Ile-Lys-Asn-Lys-Arg-Lys-Gln.

MLPs described herein are membrane active and therefore capable of disrupting plasma membranes or lysosomal/endocytic membranes. As used herein, membrane active peptides are surface active, amphipathic peptides that are able to induce one or more of the following effects upon a biological membrane: an alteration or disruption of the membrane that allows non-membrane permeable molecules to enter a cell or cross the membrane, pore formation in the membrane, fission of membranes, or disruption or dissolving of the membrane. As used herein, a membrane, or cell membrane, comprises a lipid bilayer. The alteration or disruption of the membrane can be functionally defined by the peptide's activity in at least one the following assays: red blood cell lysis (hemolysis), liposome leakage, liposome fusion, cell fusion, cell lysis, and endosomal release. Peptides that preferentially cause disruption of endosomes or lysosomes over plasma membranes are considered endosomolytic. The effect of membrane active peptides on a cell membrane may be transient. Membrane active peptides possess affinity for the membrane and cause a denaturation or deformation of bilayer structures. Delivery of a RNAi trigger to a cell is mediated by the MLP disrupting or destabilizing the plasma membrane or an internal vesicle membrane (such as an endosome or lysosome), including forming a pore in the membrane, or disrupting endosomal or lysosomal vesicles thereby permitting release of the contents of the vesicle into the cell cytoplasm.

Membrane activity of the MLPs is reversibly masked to yield MLP delivery polymers. Masking is accomplished through reversible attachment of masking agents to primary amines of the MLP.

It is an essential feature of the masking agents that, in aggregate, they inhibit membrane activity of the MLP and provide in vivo hepatocyte targeting. As used herein, MLP is masked if the modified MLP (MLP delivery polymer) does not exhibit membrane activity and exhibits cell-specific (i.e. hepatocyte) targeting in vivo. MLP is reversibly masked if cleavage of bonds linking the masking agents to the peptide results in restoration of amines on the MLP thereby restoring membrane activity. It is an essential feature that the masking agents are covalently bound to the MLP through physiologically labile reversible bonds. By using physiologically labile reversible linkages or bonds, the masking agents can be cleaved from the MLP in vivo, thereby unmasking the MLP and restoring activity of the unmasked MLP. A sufficient number of masking agents are linked to the MLP to achieve the desired level of inactivation. The desired level of modification of MLP by attachment of masking agent(s) is readily determined using appropriate peptide activity assays. For example, if MLP possesses membrane activity in a given assay, a sufficient level of masking agent is linked to the MLP to achieve the desired level of inhibition of membrane activity in that assay. Modification of >80% or >90% of the primary amine groups on a population of MLP peptides, as determined by the quantity of primary amines on the peptides in the absence of any masking agents, is preferred. It is also a preferred characteristic of masking agents that their attachment to the peptide reduces positive charge of the polymer, thus forming a more neutral delivery polymer. It is desirable that the masked peptide retain aqueous solubility.

An MLP delivery polymer comprises an MLP reversibly modified by reaction of primary amines on the peptide with asialoglycoprotein receptor (ASGPr) ligand-containing masking agents wherein said reversibly modification is physiologically labile, as described in WO 2012/083185.

As used herein, a masking agent comprises a preferably neutral (uncharged) compound having an ASGPr ligand and an amine-reactive group wherein reaction of the amine-reactive group with an amine on a peptide results in linkage of the ASGPr ligand to the peptide via a reversible physiologically labile covalent bond. An amine is reversibly modified if cleavage of the modifying group restores the amine. A preferred ASGPr ligand-containing masking agent has a neutral charge and comprises a ASGPr ligand, such as a galactosamine or galactosamine derivative, having a disubstituted maleic anhydride amine-reactive group. The membrane active polyamine can be conjugated to masking agents in the presence of an excess of masking agents. The excess masking agent may be removed from the conjugated delivery polymer prior to administration of the delivery polymer.

Galactose and galactose derivatives have been used to target molecules to hepatocytes in vivo through their binding to the asialoglycoprotein receptor (ASGPr) expressed on the surface of hepatocytes. As used herein, a ASGPr ligand (or ASGPr ligand) comprises a galactose and galactose derivative having affinity for the ASGPr equal to or greater than that of galactose. Binding of galactose targeting moieties to the ASGPr(s) facilitates cell-specific targeting of the delivery polymer to hepatocytes and endocytosis of the delivery polymer into hepatocytes. ASGPr ligands may be selected from the group comprising: lactose, galactose, N-acetylgalactosamine (GalNAc), galactosamine, N-formylgalactosamine, N-acetyl-galactosamine, N-propionylgalactosamine, N-n-butanoylgalactosamine, and N-iso-butanoylgalactosamine (Iobst, S. T. and Drickamer, K. *J.B.C.* 1996, 271, 6686). ASGPr ligands can be monomeric (e.g., having a single galactosamine) or multimeric (e.g., having multiple galactosamines).

A preferred masking agent comprises a neutral hydrophilic disubstituted alkylmaleic anhydride:

$$\text{structure with } R1 \text{ and alkyl}$$

wherein R1 comprises an uncharged asialoglycoprotein receptor ligand. A preferred alkyl group is a methyl or ethyl group. An example of a substituted alkylmaleic anhydride consists of a 2-propionic-3-alkylmaleic anhydride derivative. A neutral hydrophilic 2-propionic-3-alkylmaleic anhydride derivative is formed by attachment of a neutral hydrophilic group to a 2-propionic-3-alkylmaleic anhydride through the 2-propionic-3-alkylmaleic anhydride γ-carboxyl group:

$$\text{structure with } R1 \text{ and } ()_n$$

wherein R1 comprises a neutral ASGPr ligand and n=0 or 1. In one embodiment, the ASGPr ligand is linked to the anhydride via a short PEG linker.

The ASGPr ligand provides targeting function through affinity for ASGPr. Preferred ASGPr ligands contain saccharides having affinity for the ASGPr, including but not limited to: galactose, N-acetyl-galactosamine and galactose derivatives. Galactose derivatives having affinity for the ASGPr are well known in the art.

The invention includes conjugate delivery systems of the composition:

N-T and MLP-(L-M)$_x$, wherein N is a AAT RNAi trigger, T comprises a hydrophobic group having 20 or more carbon atoms, MLP is a melittin-like peptide as described herein, and M contains an ASGPr ligand as described herein covalently linked to MLP via a physiologically labile reversible maleamate linkage L. Cleavage of L restores an unmodified amine on MLP. x is an integer greater than 1. More specifically, the value of x is greater than 80% and up to 100% of the number of primary amines on a population MLP. As used herein, MLP-(L-M)$_x$ is an MLP delivery polymer.

Sufficient percentage of MLP primary amines are modified to inhibit membrane activity of the peptide and provide for hepatocyte targeting. Preferably x has a value greater than 80%, and more preferably greater than 90%, of the number of primary amines on a population of MLP, as determined by the quantity of amines on the population of MLP in the absence of any masking agents. It is noted that a single MLP typically contains 3-5 primary amines (the amino terminus (if unmodified) and typically 2-4 Lysine residues). In its unmodified state, MLP is membrane active. However, MLP delivery polymer, MLP-(L-M)$_x$, is not membrane active. Reversible modification of MLP primary amines, by attachment of M, reversibly inhibits or inactivates membrane activity of MLP. Upon cleavage of reversible linkages L, unmodified amines are restored thereby reverting the MLP to its unmodified, membrane active state. MLP-(L-M)$_x$, an ASGPr-targeted reversibly masked membrane active polymer, and T-N, an RNAi trigger-conjugate, are synthesized or manufactured separately. Neither T nor N are covalently linked directly or indirectly to MLP, L, or M. Electrostatic or hydrophobic association of the RNAi trigger or the RNAi-trigger-conjugate with the masked or unmasked polymer is not required for in vivo liver delivery of the RNAi-trigger. The masked polymer and the RNAi-trigger conjugate can be supplied in the same container or in separate containers. They may be combined prior to administration, co-administered, or administered sequentially.

In one aspect, we describe a pharmaceutical composition for inhibiting expression of a AAT gene comprising a described herein AAT RNAi trigger described herein.

In one embodiment, the RNAi trigger is administered in an unbuffered solution. In one embodiment, the unbuffered solution is saline or water. In one embodiment, the RNAi trigger is administered with a buffer solution. In one embodiment, the buffer solution comprises acetate, citrate, prolamine, carbonate, or phosphate or any combination thereof. In another embodiment, the buffer solution is phosphate buffered saline (PBS).

Administration of a described AAT RNAi trigger according to the methods and uses described herein may result in a reduction of the severity, signs, symptoms, and/or markers of such diseases or disorders in a subject having a disorder that would benefit from inhibiting or reducing the expression of AAT, such as AATD. Efficacy of treatment or prevention of disease can be assessed, for example by measuring disease progression, disease remission, symptom severity, reduction in pain, quality of life, dose of a medication required to sustain a treatment effect, level of a disease marker or any other measurable parameter appropriate for a given disease being treated or targeted for prevention.

"Therapeutically effective amount," as used herein, is intended to include the amount of an AAT RNAi trigger or co-treatment, that, when administered to a subject having a AATD, is sufficient to effect treatment of the disease (e.g., by diminishing, ameliorating or maintaining the existing disease or one or more symptoms of disease). The "therapeutically effective amount" may vary depending on the AAT RNAi trigger, co-treatment, how the trigger is administered, the disease and its severity and the history, age, weight, family history, genetic makeup, the types of preceding or concomitant treatments, if any, and other individual characteristics of the subject to be treated.

"Prophylactically effective amount," as used herein, is intended to include the amount of a AAT RNAi trigger agent or co-treatments, that, when administered to a subject having a AATD but not yet (or currently) experiencing or displaying symptoms of the disease, and/or a subject at risk of developing a AATD, is sufficient to prevent or ameliorate the disease or one or more symptoms of the disease. Ameliorating the disease includes slowing the course of the disease or reducing the severity of later-developing disease.

In one embodiment, the dose can be: 0.0005, 0.001, 0.005, 0.01, 0.02, 0.03, 0.04, 0.05, 0.06, 0.07, 0.08, 0.09, 0.1, 0.125, 0.15, 0.175, 0.2, 0.225, 0.25, 0.275, 0.3, 0.325, 0.35, 0.375, 0.4, 0.425, 0.45, 0.475, 0.5, 0.525, 0.55, 0.575, 0.6, 0.625, 0.65, 0.675, 0.7, 0.725, 0.75, 0.775, 0.8, 0.825, 0.85, 0.875, 0.9, 0.925, 0.95, 0.975, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 31, 32, 33, 34, 34, 35, 36, 37, 38, 39, 40, 41, 42, 43, 44, 45, 46, 47, 48, 49, or 50 mg/kg. Values intermediate to the recited values are also intended to be part of this invention.

In another embodiment, the dose can be: 0.1 to 50, 0.25 to 50, 0.5 to 50, 0.75 to 50, 1 to 50, 1.5 to 50, 2 to 50, 2.5 to 50, 3 to 50, 3.5 to 50, 4 to 50, 4.5 to 50, 5 to 50, 7.5 to 50, 10 to 50, 15 to 50, 20 to 50, 20 to 50, 25 to 50, 25 to 50, 30 to 50, 35 to 50, 40 to 50, or 45 to 50 mg/kg.

In another embodiment, the dose can be: 0.1 to 45, 0.25 to 45, 0.5 to 45, 0.75 to 45, 1 to 45, 1.5 to 45, 2 to 45, 2.5 to 45, 3 to 45, 3.5 to 45, 4 to 45, 4.5 to 45, 5 to 45, 7.5 to 45, 10 to 45, 15 to 45, 20 to 45, 20 to 45, 25 to 45, 25 to 45, 30 to 45, 35 to 45, or 40 to 45 mg/kg.

In another embodiment, the dose can be: 0.1 to 40, 0.25 to 40, 0.5 to 40, 0.75 to 40, 1 to 40, 1.5 to 40, 2 to 40, 2.5 to 40, 3 to 40, 3.5 to 40, 4 to 40, 4.5 to 40, 5 to 40, 7.5 to 40, 10 to 40, 15 to 40, 20 to 40, 20 to 40, 25 to 40, 25 to 40, 30 to 40, or 35 to 40 mg/kg.

In another embodiment, the dose can be: 0.1 to 30, 0.25 to 30, 0.5 to 30, 0.75 to 30, 1 to 30, 1.5 to 30, 2 to 30, 2.5 to 30, 3 to 30, 3.5 to 30, 4 to 30, 4.5 to 30, 5 to 30, 7.5 to 30, 10 to 30, 15 to 30, 20 to 30, 20 to 30, 25 to 30 mg/kg.

In another embodiment, the dose can be: 0.1 to 20, 0.25 to 20, 0.5 to 20, 0.75 to 20, 1 to 20, 1.5 to 20, 2 to 20, 2.5 to 20, 3 to 20, 3.5 to 20, 4 to 20, 4.5 to 20, 5 to 20, 7.5 to 20, 10 to 20, or 15 to 20 mg/kg.

In another embodiment, the dose can be: 0.01 to 10, 0.05 to 10, 0.1 to 10, 0.2 to 10, 0.3 to 10, 0.4 to 10, 0.5 to 10, 1 to 10, 1.5 to 10, 2 to 10, 2.5 to 10, 3 to 10, 3.5 to 10, 4 to 10, 4.5 to 10, 5 to 10, 5.5 to 10, 6 to 10, 6.5 to 10, 7 to 10, 7.5 to 10, 8 to 10, 8.5 to 10, 9 to 10, or 9.5 to 10 mg/kg.

In another embodiment, the dose can be: 0.01 to 5, 0.05 to 5, 0.1 to 5, 0.2 to 5, 0.3 to 5, 0.4 to 5, 0.5 to 5, 1 to 5, 1.5 to 5, 2 to 5, 2.5 to 5, 3 to 5, 3.5 to 5, 4 to 5, or 4.5 to 5 mg/kg.

In another embodiment, the dose can be: 0.01 to 2.5, 0.05 to 2.5, 0.1 to 2.5, 0.2 to 2.5, 0.3 to 2.5, 0.4 to 2.5, 0.5 to 5, 1 to 2.5, 1.5 to 2.5, or 2 to 2.5 mg/kg.

In one embodiment, the AAT RNAi trigger is administered once. In another embodiment, administration of the AAT RNAi trigger is repeated (i.e., repeat-dose regimen or multi-dose regimen). For repeated administrations, the AAT RNAi trigger may be administered to the subject once per day, every other day, once every three days, once every four days, once every five days, once every six days, twice a week, once a week, once every two weeks, once every three weeks, once every four weeks, once every four (4) to fourteen (14) weeks, twice a month, once a month, once every two months, once every three months less, or once every four months or longer. Values intermediate to the recited values are also intended to be part of this invention. In another embodiment, the AAT trigger can be administered as necessary. In another embodiment, an initial treatment regimen may comprise repeat administration at an initial time interval and subsequent administration on a less frequent basis. For example, after administration weekly or biweekly for one to six months, administration can thereafter be repeated once per month or less. The initial time interval can be a set number of administrations, a set span of time, or until a determined reduction in AAT is measured. For any dosing regimen, whether single or repeat, any of the above amounts may be used. For repeat dosing, the same dose or different doses may be used for each administration.

The invention also provides for cells comprising at least one of the RNAi triggers described herein. The cell is preferably a mammalian cell, such as a human cell. Furthermore, tissues and/or non-human organisms comprising the herein defined RNAi trigger molecules are an embodiment of this invention, whereby said non-human organisms are particularly useful for research purposes or as research tools, for example in drug testing.

The above provided embodiments and items of the present invention are now illustrated with the following, non-limiting examples.

EXAMPLES

Example 1. Identification of RNAi Trigger Sequences

A selection process for identifying lead UNAs to target AAT began with in silico methods to identify conserved sequences across variants of the AAT gene. The AAT cDNA sequence was initially screened for 17-nucleotide sequences having an exact complementary sequence in eleven known variants of human AAT. Sequences known to have manufacturing challenges, such as runs of five (5) or more guanines or cytosines, and those predicted to have poor RNAi activity based on known siRNA parameters were eliminated. Sequences that included a single nucleotide polymorphism (SNP) with a major allele frequency of greater than 0.2 at position 2 to 18 of a 19-mer sequence were also eliminated. Sequences were then subjected to cross-species reactivity analysis to select candidates that would cross-react with cynomolgus monkey AAT. In silico analysis yielded 840 sequences that were 19-mers and 939 sequences that were 17-mers. These sequences were then evaluated for specificity to avoid off-target effects against the human and cynomolgus genomes. Sequences containing a conserved miRNA seed region in positions 2-7 of either siRNA strand with off-target genes were eliminated. 47 candidate sequences were then selected for use in generating RNAi trigger molecules.

Example 2. RNAi Trigger Synthesis

A) Synthesis.

RNAi trigger molecules were synthesized according to phosphoramidite technology on solid phase used in oligonucleotide synthesis. Depending on the scale either a MerMade96E (Bioautomation) or a MerMade12 (Bioautomation) was used. Syntheses were performed on a solid support made of controlled pore glass (CPG, 500 Å for dT and 600 Å for inverse dT, obtained from Prime Synthesis, Aston, Pa., USA). All 2'-modified RNA phosphoramidites as well as ancillary reagents were purchased from Thermo Fisher Scientific (Milwaukee, Wis., USA). Specifically, the following 2'-O-Methyl phosphoramidites were used: (5'-O-dimethoxytrityl-$N^6$-(benzoyl)-2'-O-methyl-adenosine-3'-O-(2-cyanoethyl-N,N-diisopropylamino) phosphoramidite, 5'-O-dimethoxy-trityl-$N^4$-(acetyl)-2'-O-methyl-cytidine-3'-O-(2-cyanoethyl-N,N-diisopropylamino) phosphoramidite, (5'-O-dimethoxytrityl-$N^2$-(isobutyryl)-2'-O-methyl-guanosine-3'-O-(2-cyano-ethyl-N,N-diisopropylamino)phosphoramidite, and 5'-O-dimethoxy-trityl-2'-O-methyl-uridine-3'-O-(2-cyanoethyl-N,N-diisopropylamino)phosphoramidite. The 2'-Deoxy-2'-fluoro-phosphor-amidites carried the same protecting groups as the 2'-O-methyl RNA amidites. 5'-(4,4'-Dimethoxytrityl)-2',3'-seco-uridine, 2'-benzoyl-3'-[(2-cyanoethyl)-(N,N-diisopropyl)]-phosphoramidite was purchased from Link Technologies Ltd, Scotland. All amidites were dissolved in anhydrous acetonitrile (50 mM) and molecular sieves (3 Å) were added. In order to introduce the TEG-Cholesterol at the 5'-end of the oligomers, the 1-Dimethoxytrityloxy-3-O—(N-cholesteryl-3-aminopropyl)-triethyleneglycol-glyceryl-2-O-(2-cyanoethyl)-(N,N,-diisopropyl)-phosphoramidite from Glen Research (Sterling, Va., USA) was employed. The 5'-modifications were introduced without any modification of the synthesis cycle. 5-Benzyl-thio-1H-tetrazole (BTT, 250 mM in acetonitrile) was used as activator solution. Coupling times were 10 min (RNA), 180 sec (Cholesterol), 90 sec (2'OMe and UNA), and 60 sec (2'F and DNA). In order to introduce phosphorothioate linkages, a 100 mM solution of 3-phenyl 1,2,4-dithiazoline-5-one (POS, obtained from PolyOrg, Inc., Leominster, Mass., USA) in anhydrous Acetonitrile was employed. See Tables 1-5 (FIG. 1-5). For

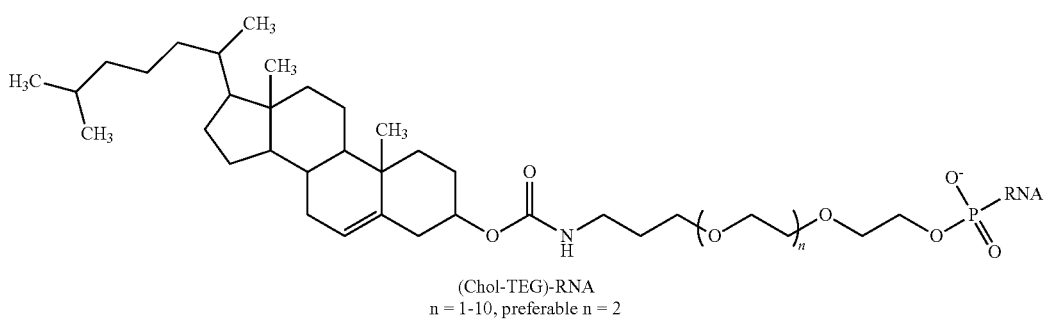

(Chol-TEG)-RNA
n = 1-10, preferable n = 2

B. Cleavage and Deprotection of Support Bound Oligomer.

After finalization of the solid phase synthesis, the dried solid support treated with a 1:1 volume solution of 40 wt. % methylamine in water and 28% ammonium hydroxide solution (Aldrich) for two hours at room temperature. The solution was evaporated and the solid residue was reconstituted in water (see below).

C. Purification.

Crude Cholesterol containing oligomers were purified by reverse phase HPLC using a Waters XBridge BEH300 C4 5 u Prep column and a Shimadzu LC-8 system. Buffer A was 100 mM TEAA, pH 7.5 and contained 5% Acetonitrile and buffer B was 100 mM TEAA and contained 95% Acetonitrile. A gradient of 45% B to 55% B over 25 minutes was employed. UV traces at 260 nm were recorded. Appropriate fractions were then run on size exclusion HPLC using a GE Healthcare XK 16/40 column packed with Sephadex G-25 medium with a running buffer of 100 mM ammonium bicarbonate, pH 6.7 and 20% Acetonitrile. Other crude oligomers were purified by anionic exchange HPLC using a TKSgel SuperQ-5PW 13 u column and Shimadzu LC-8 system. Buffer A was 20 mM Tris, 5 mM EDTA, pH 9.0 and contained 20% Acetonitrile and buffer B was the same as buffer A with the addition of 1.5 M sodium chloride. A gradient of 32.5% B to 42.5% B over 25 minutes was employed. UV traces at 260 nm were recorded. Appropriate fractions were pooled then run on size exclusion HPLC as described for Cholesterol containing oligomers.

D. Annealing.

Complementary strands were mixed by combining equimolar RNA solutions (sense and antisense) in 0.2×PBS (Phosphate-Buffered Saline, 1×, Corning, Cellgro) to form the RNAi triggers. This solution was placed into a thermomixer at 70° C., heated to 95° C., held at 95° C. for 5 min, and cooled to room temperature slowly. Some RNAi triggers were lyophilized and stored at −15 to −25° C. Duplex concentration was determined by measuring the solution absorbance on a UV-Vis spectrometer in 0.2×PBS. The solution absorbance at 260 nm was then multiplied by a conversion factor and the dilution factor to determine the duplex concentration. Unless otherwise stated, all conversion factor was 0.037 mg/(mL·cm). For some experiments, a conversion factor of 0.0502 mg/(mL·cm) was used.

Example 3. Melittin-Like-Peptide (MLP) Delivery Polymer

A) Melittin-Like-Peptide (MLP) Synthesis.

All MLPs were made using peptide synthesis techniques standard in the art. Suitable MLPs can be all L-form amino acids, all D-form amino acids (inverso). Independently of L or D form, the MLP sequence can be reversed (retro).

B) CDM-NAG (N-Acetyl Galactosamine) Synthesis.

To a solution of CDM (300 mg, 0.16 mmol) in 50 mL methylene chloride was added oxalyl chloride (2 g, 10 wt. eq.) and dimethylformamide (5 μl). The reaction was allowed to proceed overnight, after which the excess oxalyl chloride and methylene chloride were removed by rotary evaporation to yield the CDM acid chloride. The acid chloride was dissolved in 1 mL of methylene chloride. To this solution was added 1.1 molar equivalents (aminoethoxy)ethoxy-2-(acetylamino)-2-deoxy-β-D-galactopyranoside (i.e. amino bisethoxyl-ethyl NAG) and pyridine (200 μl, 1.5 eq) in 10 mL of methylene chloride. The solution was then stirred 1.5 h. The solvent was then removed and the resulting solid was dissolved into 5 mL of water and purified using reverse-phase HPLC using a 0.1% TFA water/acetonitrile gradient.

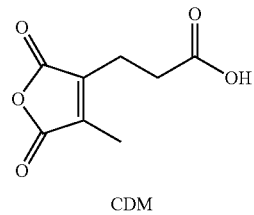

CDM

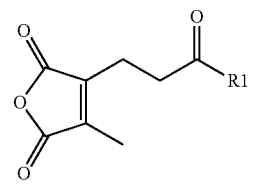

R1 comprises a neutral ASGPr ligand. Preferably the Masking Agent is uncharged.

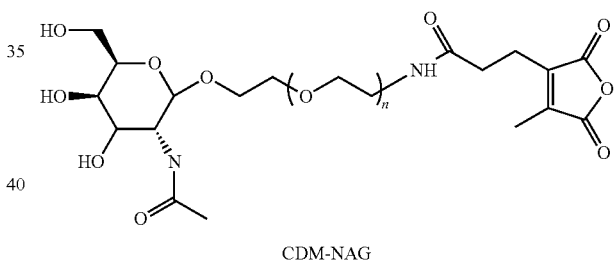

CDM-NAG n is an integer from 1 to 10. As shown above, a PEG spacer may be positioned between the anhydride group and the ASGPr ligand. A preferred PEG spacer contains 1-10 ethylene units. Alternatively an alkyl spacer may be used between the anhydride and the N-Acetylgalactosamine.

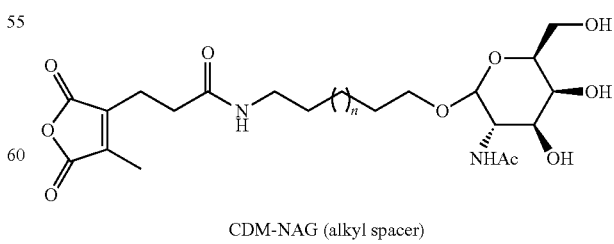

CDM-NAG (alkyl spacer)

n is a integer from 0 to 6.

Other spacers or linkers may be used between the anhydride and the N-Acetyl-galactosamine. However, a hydrophilic, neutral (preferably uncharged) spacer or linker is preferred.

C) Formation of the MLP delivery polymer (i.e. masking).

The MLP was reacted with CDM-NAG masking agent to yield the MLP delivery polymer. The MLP component was first dissolved to a final concentration of 8.5 mg/mL in aqueous HEPES (sodium salt, GMP grade, ~430 mg/mL). The MLP solution was then cooled to 4° C., and checked for appearance (clear to pale yellow solution free of visible particulate) and for concentration by UV spectrophotometry. CDM-NAG was dissolved in water at 4° C. at a final concentration of ~75 mg/mL. The solution was checked for appearance (clear to pale yellow solution free of visible particulate) and for concentration by UV spectrophotometry. MLP in solution was mixed with CDM-NAG in solution at a 5:1 (w/w) ratio of CDM-NAG to MLP. The addition rate of CDM-NAG solution was approximately 0.3 L per minute, while stirring. After all CDM-NAG solution had been added to the MLP solution, the mixture was stirred for 30 minutes. To stabilize the MLP delivery polymer, the pH was increased to 9.0±0.2 by addition of 1 M aqueous sodium hydroxide. Reaction of disubstituted maleic anhydride masking agent with the peptide yielded a compound having the structure represented by:

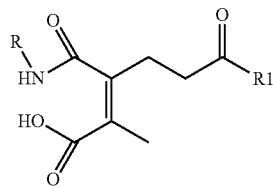

wherein R is MLP and R1 comprises an ASGPr ligand (e.g. NAG).

Colorimetric trinitrobenzene sulfonic acid (TNBS) assay of remaining free amines was used to determine that MLP was sufficiently masked by CDM-NAG, less than 10% of the total number of MLP amines remained unmodified.

MLP delivery polymer was purified by diafiltration against 10 mM, pH 9.2 carbonate buffer to remove excess CDM-NAG. The diafiltration process exchanged ~10 volumes of carbonate buffer per volume of masked MLP reaction solution and held at 2-8° C.

| Component | Quantity (nominal) |
|---|---|
| MLP-EX1 Acetate | 30 g/L |
| CDM-NAG[a] | 25 g/L |
| Sodium carbonate | 0.3 g/L |
| Sodium bicarbonate | 0.6 g/L |
| Water | 1000 g/L |

[a]assumes five (5) CDM-NAG moieties per MLP

The MLP delivery polymer was further formulated with Dextran to 10% w/v and stored at 2 to 8° C. For some experiments, this solution was lyophilized prior to use.

D) Injection Solution.

The injection solution was formed by mixing RNAi trigger with the MLP delivery polymer. The lyophilized MLP delivery polymer was dissolved in water and mixed with the RNAi trigger. That solution was then diluted to the correct injection concentration with normal saline.

Example 4. In Vitro Screening of siRNAs

Candidate sequences identified by in silico analysis (Example 1) were screened as chemically modified canonical siRNAs in vitro. Forty-six of the in silico identified potential AAT RNAi triggers were synthesized as canonical siRNAs and screened for efficacy in vitro. Hep3B cells, a human hepatocellular carcinoma line, were plated at ~10,000 cells per well in 96-well format. Each of the 46 siRNAs was transfected at two concentrations, 1 nM and 10 nM, in triplicate, using Lipofectamine RNAiMax (Life Technologies, 0.34/well). Twenty-four hours post-transfection, cells were lysed and cDNA were generated (TaqMan Cells-to-CT Gene Expression kit, Life Technologies). AAT gene knockdown was assessed by qRT-PCR with TaqMan chemistry-based assays (Life Technologies) for human AAT (Assay ID: Hs01097800_m1), normalized to the endogenous control, human cyclophilin A (PPIA, 4326316E). Of the 46 siRNAs tested in vitro, five exhibited AAT knockdown of at least 80%. These were chosen for further analysis. Ten-point $EC_{50}$ curves were generated using the same cells and transfection conditions, with siRNA concentrations ranging from 0.001-1 nM. Additionally, each of the five most efficacious canonical siRNAs was redesigned and synthesized as a corresponding mero RNAi trigger, UNA RNAi trigger and locked nucleic acid (LNA) RNAi trigger. The resultant RNAi triggers were again examined by in vitro knockdown analysis, by both two-point concentration analysis at 1 nM and 0.1 nM and ten-point $ED_{50}$ determination. The most efficacious of these were chosen for further in vivo studies. The most potent of these, SEQ ID 50/62 targeted position 1142-1160 in the AAT mRNA and had an EC50 of 0.01 nM. Serum Factor VII (F7) Activity Measurements.

Serum samples from animals were prepared by collecting blood into microcentrifuge tubes. F7 activity in plasma was measured with a chromogenic method using a BIOPHEN VII kit (Hyphen BioMed/Aniara, Mason, Ohio) following manufacturer's recommendations. Absorbance of colorimetric development was measured using a Tecan Safire2 microplate reader at 405 nm.

Example 5. In Vivo Analysis of RNAi Trigger Efficacy in Mouse AATD Model

In order to evaluate the efficacy of candidate RNAi triggers in vivo, transgenic PiZ mouse model (PiZ mice) was used. PiZ mice harbor the human PiZ AAT mutant allele and model human AATD (Carlson et al. Journal of Clinical Investigation 1989). As noted above, AAT RNAi triggers where chosen in silico for interaction with human and cynomolgus monkey AAT but not with rat or mouse AAT.

Cholesterol-targeted RNAi triggers were delivered to PiZ mice using MLP delivery polymer. Each mouse received an intravenous (IV) injection into the tail vein of 200-250 μL solution containing a dose of 8 or 2 mg/kg RNAi trigger+8 mg/kg MLP delivery polymer (1:1 or 0.25:1 w/w RNAi trigger:delivery polymer, respectively). Human AAT protein (hAAT) levels in serum were monitored by assaying serum from the mice using an ELISA for hAAT (Abcam) until hAAT expression levels returned to baseline. For normalization, AAT level for each animal at a time point was divided by the pre-treatment level of expression in that animal (in this case at day 1) to determine the ratio of expression "normalized to day 1". Expression at a specific time point was then normalized to the saline control group by dividing the "normalized to day 1" ratio for an individual animal by the mean "normalized to day 1" ratio of all mice in the saline control group. This resulted in expression for each time point normalized to that in the control group. Experimental error is given as standard deviation.

mRNA quantitation. Isolation of RNA from PiZ mouse liver was performed as follows. At the time of euthanization, one to three sections of the liver were snap-frozen in 1.5 mL microcentrifuge tubes using liquid nitrogen. One liver section from each mouse was transferred to 2 mL of TRI Reagent RT (Molecular Research Center, Inc., Cincinnati, Ohio) in a 15 mL conical tube. Total RNA was isolated following the manufacturer's recommended protocol. Briefly, liver sections in TRI Reagent RT were treated with a tissue homogenizer for approximately 30 sec. 1 mL homogenate was added to 50 μL of 4-bromoanisole, mixed, and phases were separated by centrifugation. 0.25-0.5 mL of aqueous phase was removed, precipitated with isopropyl alcohol, and centrifuged. The resultant pellet was washed with 75% ethanol and suspended in 0.3-0.7 mL nuclease-free water.

Total RNA (~500 ng) was reverse transcribed using the High Capacity cDNA Reverse Transcription Kit (Life Technologies, Grand Island, N.Y.). The cDNA was then diluted 1:5 and multiplex RT-qPCR was performed using 5' exonuclease chemistry with the commercially available FAM-labeled assay for human alpha-1-antitrypsin (Assay ID Hs01097800_m1, Life Technologies), the VIC-labeled endogenous control assay for mouse beta-actin (Life Technologies) and VeriQuest Master Mix (Affymetrix, Santa Clara, Calif.). Gene expression data were analyzed using the comparative $C_T$ method of relative quantification (Livak and Schmittgen, 2001).

TABLE 7

PiZ mouse in vivo procedures.

| day | procedure |
|---|---|
| Day −7, −3, −2 or −1 | Bleed and serum isolation for hAAT ELISA |
| Day 1 | a) Bleed and serum isolation for hAAT ELISA<br>b) IV injection of samples |
| Day 3 | Bleed and serum isolation for hAAT ELISA<br>Collect liver tissue (for RNA isolation) |
| Day 8 | Bleed and serum isolation for hAAT ELISA weekly |

TABLE 7-continued

PiZ mouse in vivo procedures.

| day | procedure |
|---|---|
| Day 10 | Bleed and serum isolation for hAAT ELISA;<br>Collect liver tissue (for RNA isolation) |
| Day 15, 22, 29, 36, 43 | Weekly bleed and serum isolation for hAAT ELISA |

Example 6. Screening AAT siRNA RNAi Triggers and Time Course of AAT Knockdown

Cholesterol-conjugated canonical siRNA RNAi triggers were administered to PiZ mice as described above. Each mouse received a single intravenous (IV) dose of 2 mg/kg of RNAi trigger with 8 mg/kg of MLP delivery polymer. Human AAT protein levels in serum were monitored for up to 29 days. Knockdown levels and duration of response are shown in Table 8. A decrease in hAAT serum protein level of greater than 95% was obtained following administration of SEQ ID 50/63 and SEQ ID 56/77.

TABLE 8

Serum hAAT protein levels in PiZ mice following administration of 2 mg/kg siRNA with 8 mg/kg MLP delivery polymer. AAT levels were normalized to day 1 and saline control.

| | Serum hAAT normalized to control group | | | | | | |
|---|---|---|---|---|---|---|---|
| Treatment | day −2 | day 1 | day 3 | day 8 | day 15 | day 22 | day 29 |
| Saline | 1.00 ± 0.49 | 1.00 | 1.00 ± 0.35 | 1.00 ± 0.32 | 1.00 ± 0.17 | 1.00 ± 0.19 | 1.00 ± 0.47 |
| SEQ ID 50/63 | 1.03 ± 0.11 | 1.00 | 0.03 ± 0.01 | 0.02 ± 0.00 | 0.60 ± 0.42 | 1.30 ± 0.80 | 1.39 ± 0.38 |
| SEQ ID 56/77 | 0.86 ± 0.23 | 1.00 | 0.22 ± 0.07 | 0.03 ± 0.01 | 0.08 ± 0.01 | 0.58 ± 0.29 | 1.26 ± 0.37 |

Example 7. Screening AAT Mero RNAi Triggers and Time Course of AAT Knockdown

Cholesterol-conjugated mero RNAi triggers were administered to PiZ mice as described above. Each mouse received a single intravenous (IV) dose of 8 or 2 mg/kg of RNAi trigger with 8 mg/kg of MLP delivery polymer. Human AAT protein levels in serum were monitored for up to 39 days. Knockdown levels and duration of response are shown in Table 10.

TABLE 9

Serum FVII levels in PiZ mice following administration of 8 mg/kg mero RNAi triggers with 8 mg/kg MLP delivery polymer. FVII levels were normalized to day 3 and saline control.

| Treatment | FVII activity |
|---|---|
| Saline | 1.00 ± 0.06 |
| SEQ ID 61/80 (FVII) | 0.15 ± 0.20 |
| SEQ ID 50/64/81 | 1.18 ± 0.17 |
| SEQ ID 50/65/82 | 1.29 ± 0.26 |
| SEQ ID 50/66/83 | 1.12 ± 0.47 |
| SEQ ID 56/76/89 | 1.24 ± 0.20 |
| SEQ ID 55/72/86 | 1.33 ± 0.09 |

TABLE 10

Serum hAAT protein levels in PiZ mice following administration of 8 mg/kg mero RNAi triggers with 8 mg/kg MLP delivery polymer. AAT levels were normalized to day 1 and saline control.

| Treatment | day −3, day −2 or day −1 | day 1 | day 3 | day 8 | day 15 | day 22 | day 29 | day 39 |
|---|---|---|---|---|---|---|---|---|
| Saline | 1.00 ± 0.10 | 1.00 | 1.00 ± 0.30 | 1.00 ± 0.08 | 1.00 | 1.00 | 1.00 | |
| SEQ ID 61/80 (FVII) 8 mg/kg | 1.07 ± 0.08 | 1.00 | 0.74 ± 0.17 | 0.79 ± 0.15 | | | | |
| SEQ ID 50/64/81 8 mg/kg | 1.13 ± 0.03 | 1.00 | 0.11 ± 0.02 | 0.84 ± 0.15 | | | | |
| SEQ ID 50/65/82 8 mg/kg | 0.80 ± 0.14 | 1.00 | 0.07 ± 0.02 | 0.09 ± 0.07 | 1.34 ± 0.38 | 1.30 ± 0.17 | 1.11 ± 0.27 | |
| SEQ ID 50/66/83 8 mg/kg | 1.08 ± 0.16 | 1.00 | 0.10 ± 0.06 | 0.57 ± 0.21 | | | | |
| SEQ ID 56/76/89 8 mg/kg | 1.10 ± 0.26 | 1.00 | 0.12 ± 0.04 | 0.07 ± 0.03 | 0.53 ± 0.01 | 1.15 ± 0.15 | 1.39 ± 0.35 | |
| SEQ ID 55/71/85 8 mg/kg | 0.68 ± 0.16 | 1.00 | 0.22 ± 0.12 | 0.38 ± 0.10 | 0.45 ± 0.08 | 0.68 ± 0.01 | 0.52 ± 0.07 | 0.65 ± 0.18 |
| SEQ ID 55/72/86 8 mg/kg | 1.19 ± 0.02 | 1.00 | 0.37 ± 0.24 | 1.07 ± 0.04 | | | | |
| SEQ ID 55/73/87 8 mg/kg | 0.69 ± 0.15 | 1.00 | 0.33 ± 0.07 | 0.49 ± 0.07 | 0.60 ± 0.12 | 0.81 ± 0.16 | 0.73 ± 0.10 | 0.69 ± 0.12 |
| SEQ ID 53/68/84 2 mg/kg | 1.18 ± 0.23 | 1.00 | 0.36 ± 0.24 | 0.77 ± 0.28 | 1.71 ± 0.20 | 1.65 ± 0.52 | 1.89 ± 0.61 | |
| SEQ ID 55/74/88 2 mg/kg | 0.77 ± 0.16 | 1.00 | 0.13 ± 0.04 | 0.79 ± 0.16 | 1.65 ± 0.14 | 1.39 ± 0.44 | 1.33 ± 0.46 | |

Example 8. In Vivo Screening AAT UNA RNAi Triggers and Time Course of AAT Knockdown Cholesterol-conjugated UNA RNAi triggers were administered to PiZ mice as described above. Each mouse received a single intravenous (IV) dose of 8 or 2 mg/kg of RNAi trigger with 8 mg/kg of MLP delivery polymer. Human AAT protein levels in serum were monitored for 40 days.

TABLE 11

Serum hAAT protein levels in PiZ mice following administration of 8 or 2 mg/kg UNA RNAi triggers with 8 mg/kg MLP delivery polymer. AAT levels were normalized to day 1 and saline control.

| Treatment | day −3 or day −2 | day 1 | day 3 | day 8 | day 15 | day 22 | day 29 | day 39 |
|---|---|---|---|---|---|---|---|---|
| Saline | 1.00 ± 0.09 | 1.00 | 1.00 ± 0.11 | 1.00 ± 0.09 | 1.00 ± 0.22 | 1.00 ± 0.10 | 1.00 ± 0.15 | 1.00 ± 0.16 |
| SEQ ID 50/63 8 mg/kg [a] | 0.52 ± 0.14 | 1.00 | 0.14 ± 0.03 | 0.03 ± 0.01 | 0.46 ± 0.13 | 0.74 ± 0.14 | 0.69 ± 0.16 | 0.77 ± 0.12 |

TABLE 11-continued

Serum hAAT protein levels in PiZ mice following administration of 8 or 2 mg/kg UNA RNAi triggers with 8 mg/kg MLP delivery polymer. AAT levels were normalized to day 1 and saline control.

Serum hAAT normalized to control group

| Treatment | day −3 or day −2 | day 1 | day 3 | day 8 | day 15 | day 22 | day 29 | day 39 |
|---|---|---|---|---|---|---|---|---|
| SEQ ID 50/63 2 mg/kg [a] | 1.03 ± 0.11 | 1.00 | 0.03 ± 0.01 | 0.02 ± 0.00 | 0.60 ± 0.42 | 1.29 ± 0.79 | 1.39 ± 0.38 | |
| SEQ ID 51/63 8 mg/kg | 0.88 ± 0.04 | 1.00 | 0.15 ± 0.00 | 0.06 ± 0.00 | 0.41 ± 0.16 | 0.61 ± 0.08 | 0.65 ± 0.10 | 0.70 ± 0.06 |
| SEQ ID 52/63 8 mg/kg | 0.81 ± 0.24 | 1.00 | 0.17 ± 0.03 | 0.03 ± 0.01 | 0.07 ± 0.04 | 0.18 ± 0.07 | 0.31 ± 0.15 | 0.49 ± 0.19 |
| SEQ ID 57/77 2 mg/kg | 0.80 ± 0.10 | 1.00 | 0.19 ± 0.04 | 0.04 ± 0.02 | 0.47 ± 0.20 | 1.05 ± 0.28 | 1.72 ± 0.04 | |
| SEQ ID 58/77 2 mg/kg | 0.81 ± 0.19 | 1.00 | 0.09 ± 0.03 | 0.05 ± 0.02 | 0.41 ± 0.24 | 0.59 ± 0.18 | 1.33 ± 0.43 | |

[a] canonical siRNA control

A decrease in hAAT serum protein level of greater than 95% was obtained following administration of canonical siRNA SEQ ID 50/63 and UNA SEQ ID 52/63. Maximum knockdown was observed 7 days after injection (day 8). Knockdown of greater than 80% reduction was sustained for more than 21 days (day 22) with UNA SEQ ID 52/63. Knockdown persisted longer for the UNA RNAi triggers than for the canonical chol-siRNA of the same sequence SEQ ID 50/63.

Example 9. Liver mRNA Analysis

AAT RNAi triggers were administered to PiZ mice as described above. Each mouse received a single intravenous (IV) dose of 6 mg/kg of RNAi trigger with 6 mg/kg of MLP delivery polymer. Liver hAAT mRNA production was measured at days 3 and 10. Reduced mRNA levels correlated with decreased serum hAAT protein levels, except that mRNA reduction preceded protein reduction by a few days. The level of liver hAAT mRNA production was measured at day 3 and day 10 following a single dose of SEQ ID 52/63 with MLP delivery polymer in PiZ mice. A sustained decrease in liver hAAT mRNA levels was observed that correlated with the decrease observed in serum hAAT protein levels.

TABLE 12

Serum hAAT protein levels in PiZ mice following administration of 6 mg/kg of SEQ ID 52/63 RNAi trigger or siLuc siRNA control with 6 mg/kg of MLP delivery polymer. Serum hAAT levels were normalized to day 1 and saline control.

Serum hAAT normalized to day 1

| Treatment | day −2 | day 1 | day 3 | day 10 |
|---|---|---|---|---|
| Saline | 0.938 ± 0.168 | 1.00 | 1.077 ± 0.127 | — |
| siLuc | 0.766 ± 0.219 | 1.00 | 1.110 ± 0.147 | — |

TABLE 12-continued

Serum hAAT protein levels in PiZ mice following administration of 6 mg/kg of SEQ ID 52/63 RNAi trigger or siLuc siRNA control with 6 mg/kg of MLP delivery polymer. Serum hAAT levels were normalized to day 1 and saline control.

Serum hAAT normalized to day 1

| Treatment | day −2 | day 1 | day 3 | day 10 |
|---|---|---|---|---|
| SEQ ID 52/63 | 1.111 ± 0.605 | 1.00 | 0.326 ± 0.021 | — |
| SEQ ID 52/63 | 0.483 ± 0.060 | 1.00 | 0.274 ± 0.072 | 0.105 ± 0.033 |

TABLE 13

Liver hAAT mRNA levels in PiZ mice following administration of 6 mg/kg SEQ ID 52/63 RNAi trigger or siLuc siRNA control with 6 mg/kg MLP delivery polymer. AAT mRNA level is expressed relative to mouse β-actin mRNA level.

| | hAAT mRNA level | |
|---|---|---|
| Treatment | day 3 | day 10 |
| Saline | 1.00 ± 0.15 | — |
| siLuc siRNA control | 1.06 ± 0.20 | — |
| SEQ ID 52/63 | 0.025 ± 0.02 | 0.055 ± 0.02 |

Example 10. In Vivo Dose Response for SEQ ID 52/63 RNAi Trigger

Figure 8:
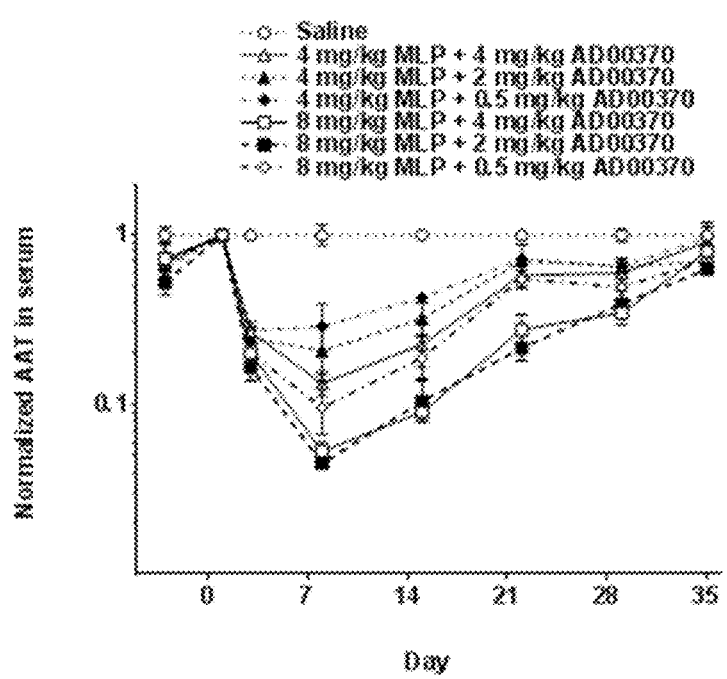
FIG. 8. Graph depicting relative serum AAT levels in PiZ mice treated saline or SEQ ID 52/63 AAT RNAi trigger (AD00370) and MLP delivery polymer (MLP).
Figure 9:
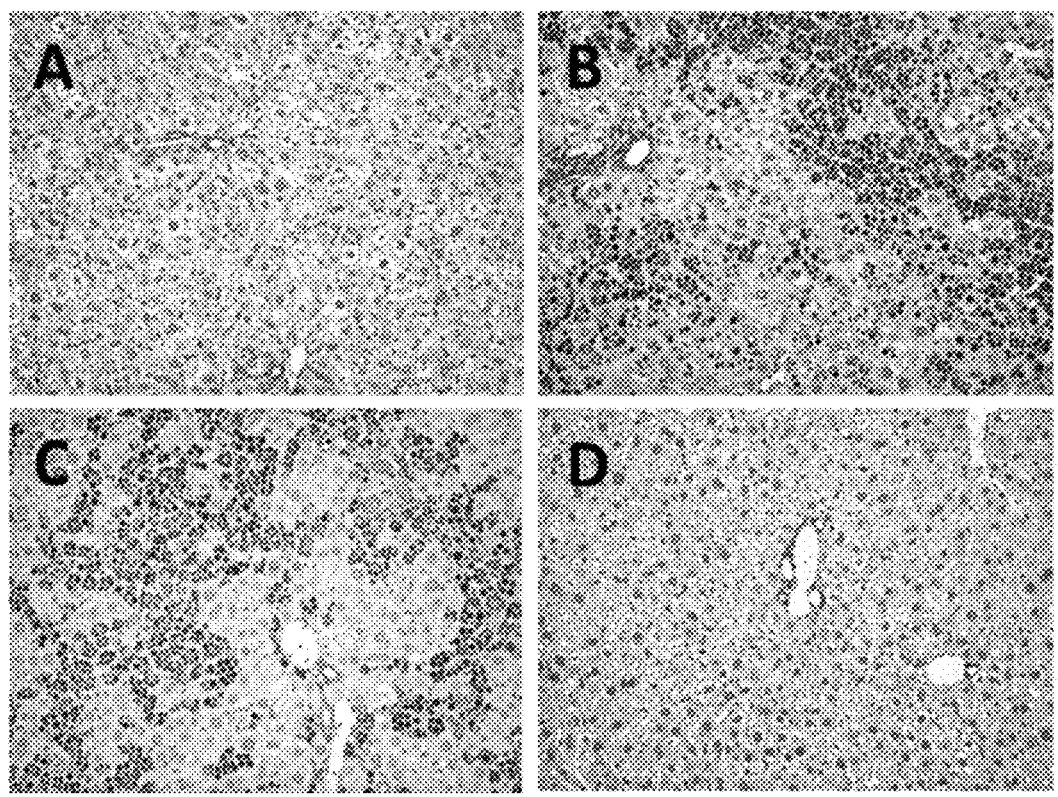
FIG. 9. PAS-D staining to visualize Z-AAT accumulation in liver. Liver sections from (A) PiZ mouse sacrificed at day 1 of study; (B) PiZ mouse receiving four biweekly IV doses of saline vehicle; (C) PiZ mouse receiving four biweekly IV doses of 8 mg/kg Luc-RNAi trigger control+8 mg/kg MLP delivery polymer; (D) PiZ mouse receiving four biweekly intravenous (IV) doses of 8 mg/kg SEQ ID 52/63 with 8 mg/kg of MLP delivery polymer.

Various amounts of UNA SEQ ID 52/63 were administered to PiZ mice as described above. Each mouse received a single intravenous (IV) dose of SEQ ID 52/63 with either 4 or 8 mg/kg of MLP delivery polymer. Human AAT protein levels in serum were monitored for 35 days. The level of hAAT knockdown was largely dose dependent, in relation to both the dose of SEQ ID 52/63 and dose of MLP delivery polymer (FIG. 8).

TABLE 14

Levels of serum hAAT in PiZ mice normalized to Day 1 and saline control group

| mg/kg SEQ ID 52/63 | mg/kg MLP delivery polymer | Serum hAAT normalized to Day 1 and control | | | | | | |
|---|---|---|---|---|---|---|---|---|
| | | Day −3 | Day 1 | Day 3 | Day 8 | Day 15 | Day 22 | Day 29 | Day 35 |
| Saline control | | 1.00 ± 0.08 | 1.00 | 1.00 ± 0.02 | 1.00 ± 0.11 | 1.00 ± 0.04 | 1.00 ± 0.02 | 1.00 ± 0.06 | 1.00 ± 0.09 |
| 4 | 8 | 0.73 ± 0.13 | 1.00 | 0.20 ± 0.04 | 0.05 ± 0.01 | 0.09 ± 0.01 | 0.28 ± 0.05 | 0.35 ± 0.05 | 0.81 ± 0.12 |
| 2 | 8 | 0.53 ± 0.08 | 1.00 | 0.17 ± 0.03 | 0.05 ± 0.00 | 0.10 ± 0.03 | 0.22 ± 0.03 | 0.40 ± 0.06 | 0.63 ± 0.04 |
| 0.5 | 8 | 0.71 ± 0.03 | 1.00 | 0.20 ± 0.02 | 0.10 ± 0.03 | 0.19 ± 0.05 | 0.55 ± 0.05 | 0.49 ± 0.09 | 0.71 ± 0.09 |
| 4 | 4 | 0.70 ± 0.17 | 1.00 | 0.27 ± 0.03 | 0.13 ± 0.02 | 0.23 ± 0.07 | 0.58 ± 0.09 | 0.60 ± 0.08 | 0.92 ± 0.22 |
| 2 | 4 | 0.67 ± 0.02 | 1.00 | 0.25 ± 0.03 | 0.21 ± 0.07 | 0.32 ± 0.06 | 0.71 ± 0.14 | 0.66 ± 0.06 | 0.70 ± 0.09 |
| 0.5 | 4 | 0.64 ± 0.10 | 1.00 | 0.27 ± 0.02 | 0.29 ± 0.09 | 0.43 ± 0.01 | 0.73 ± 0.03 | 0.66 ± 0.05 | 0.97 ± 0.02 |

Example 11. In Vivo Dose Response for SEQ ID 52/63 RNAi Trigger

Various amounts of UNA SEQ ID 52/63 were administered to PiZ mice as described above. Each mouse received a single intravenous (IV) dose of SEQ ID 52/63 with either 2, 4 or 8 mg/kg of MLP delivery polymer. Human AAT protein levels in serum were monitored for 36 days. Increasing dose of UNA generally led to increased level and duration of knockdown for each level of MLP delivery polymer excipient used.

TABLE 15

Serum hAAT protein levels in PiZ mice following administration of varying doses of SEQ ID 52/63 UNA RNAi triggers with varying doses of MLP delivery polymer. AAT levels were normalized to day 1 and saline control.

| mg/kg SEQ ID 52/63 | mg/kg MLP | Normalized serum hAAT levels | | | | | | |
|---|---|---|---|---|---|---|---|---|
| | | day −7 | day 1 | day 8 | day 15 | day 20 | day 29 | day 36 |
| Saline | | 1.00 ± 0.21 | 1.00 | 1.00 ± 0.14 | 1.00 ± 0.16 | 1.00 ± 0.12 | 1.00 ± 0.16 | 1.00 ± 0.13 |
| 2 | 2 | 0.91 ± 0.11 | 1.00 | 0.32 ± 0.24 | 0.88 ± 0.13 | 0.89 ± 0.18 | 1.01 ± 0.23 | 1.02 ± 0.15 |
| 4 | 2 | 1.27 ± 0.07 | 1.00 | 0.08 ± 0.03 | 0.68 ± 0.13 | 0.90 ± 0.15 | 1.07 ± 0.07 | 1.01 ± 0.08 |
| 8 | 2 | 0.70 ± 0.15 | 1.00 | 0.09 ± 0.05 | 0.59 ± 0.16 | 0.74 ± 0.10 | 0.87 ± 0.20 | 0.74 ± 0.08 |
| 2 | 4 | 0.90 ± 0.15 | 1.00 | 0.07 ± 0.04 | 0.50 ± 0.19 | 0.67 ± 0.12 | 0.89 ± 0.06 | 0.94 ± 0.17 |
| 4 | 4 | 0.68 ± 0.07 | 1.00 | 0.03 ± 0.01 | 0.23 ± 0.04 | 0.32 ± 0.05 | 0.66 ± 0.10 | 0.83 ± 0.06 |
| 8 | 4 | 0.70 ± 0.24 | 1.00 | 0.04 ± 0.02 | 0.27 ± 0.05 | 0.35 ± 0.05 | 0.80 ± 0.20 | 1.00 ± 0.20 |
| 8 | 8 | 0.89 ± 0.54 | 1.00 | 0.02 ± 0.00 | 0.13 ± 0.06 | 0.16 ± 0.04 | 0.43 ± 0.08 | 0.78 ± 0.23 |

Figure 10:
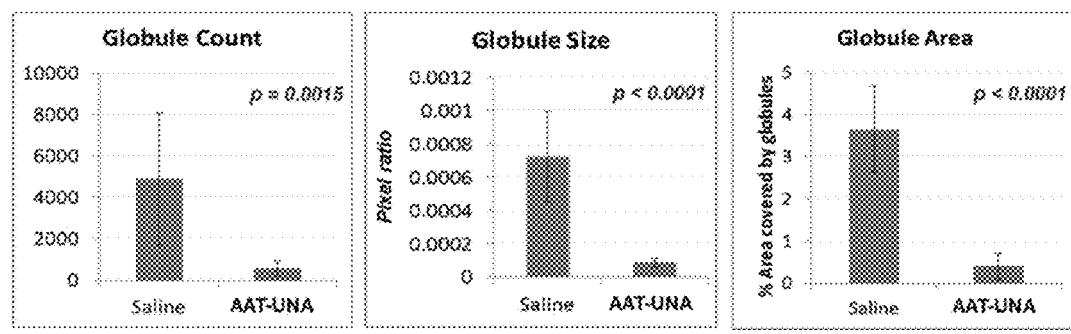
FIG. 10. Western blot analysis of the soluble and insoluble fractions from livers of PiZ mice. Five-week old mice received biweekly IV doses of saline, Luc-UNA (8 mg/kg SEQ ID 59/78 with 8 mg/kg of MLP delivery polymer), or AAT-UNA (8 mg/kg SEQ ID 52/63 with 8 mg/kg of MLP delivery polymer) for 8 weeks.

Example 12. Liver Histology in PiZ-Transgenic Mice Treated with SEQ ID 52/63 RNAi Trigger To further evaluate efficacy of hAAT knockdown in the liver, histological changes were assessed in liver samples from male PiZ mice following administration of SEQ ID 52/63 RNAi trigger with MLP delivery polymer. UNA SEQ ID 52/63 was administered to PiZ mice as described above. Each mouse received a biweekly administration of an intravenous (IV) dose of 8 mg/kg SEQ ID 52/63 with 8 mg/kg of MLP delivery polymer for 8 weeks. Mice were bled weekly to monitor hAAT levels in serum and were sacrificed on day 57 after administration of SEQ ID 52/63 with MLP delivery polymer. Liver samples were harvested and fixed in 10% neutral-buffered formalin and embedded in paraffin. Inflammatory infiltration was assessed by H&E staining. The PiZ mice injected biweekly with 8 mg/kg SEQ ID 52/63 with 8 mg/kg of MLP delivery polymer for 8 weeks had normal morphology, no detectably inflammatory infiltrate and very rare, small Z-hAAT globules. PiZ mice injected biweekly with saline had significant globule accumulation as well as inflammatory infiltration around damaged or dead hepatocytes. Aggregation of Z-hAAT was visualized by performing diastase-resistant periodic acid Schiff (PAS-D) staining on liver sections. Diastase digestion of glycogen prior to performing a PAS stain allows positive staining of Z-AAT protein accumulation, or "globules". PiZ mice that received four biweekly intravenous (IV) doses of 8 mg/kg SEQ ID 52/63 with 8 mg/kg of MLP delivery polymer over the course of 8 weeks showed a decrease in intracellular AAT globules compared to PiZ mice receiving saline or Luc UNA RNAi trigger 59/78 control injections (luciferase RNAi trigger: dTCfgAfaGfUUNAAfcUcAfgCfgUfaAfgdTsdT, SEQ ID 59; (Chol-TEG)uAuCfuUfaCfgCfuGfaGfuAfcU-fuCfgAf(invdT), SEQ ID 78). The number of globules, the size of the globules and the area of the liver covered by globules was digitally quantitated from liver specimens stained with PAS-D. AAT-UNA treated mice had 85% fewer globules, 85% smaller globules, and 96% less area of the liver covered with globules than saline-injected controls (FIG. 10).

Figure 11:
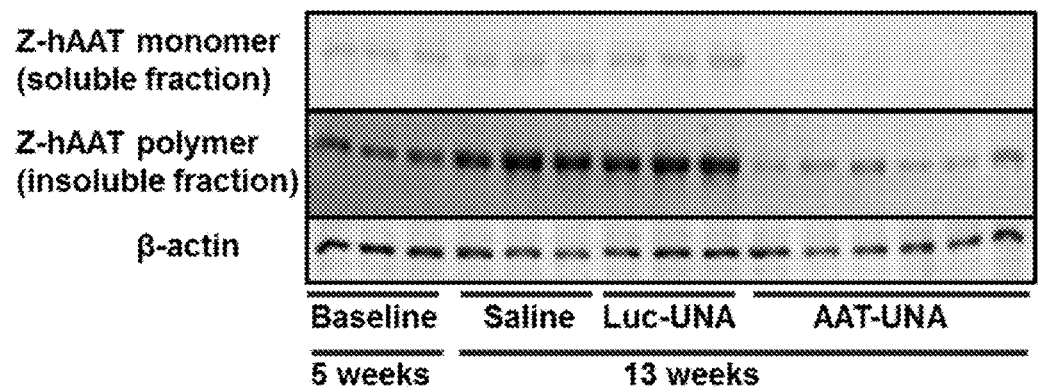
FIG. 11. Western blot analysis of the soluble and insoluble fractions from livers of PiZ mice. Five-week old mice received four biweekly IV doses of saline, Luc-UNA (8 mg/kg SEQ ID 59/78 with 8 mg/kg of MLP delivery polymer), or AAT-UNA (8 mg/kg SEQ ID 52/63 with 8 mg/kg of MLP delivery polymer) for 8 weeks.

Example 13. Analysis of Soluble and Insoluble Z-hAAT Protein in PiZ Mouse Liver Tissue Homogenized liver tissue from PiZ mice treated with SEQ ID 52/63 RNAi effector was further analyzed to determine if both soluble Z-hAAT, expected to be mostly monomeric protein, and insoluble polymers of Z-hAAT were effectively reduced. A modified western blot protocol was used to separate the soluble and insoluble Z-hAAT fractions under non-denaturing conditions as previously described (Mueller et al. Molecular Therapy 2012). PiZ mice given four biweekly intravenous (IV) doses of 8 mg/kg SEQ ID 52/63 with 8 mg/kg of MLP delivery polymer for 8 weeks showed a 99% reduction in soluble and 79% reduction in insoluble Z-hAAT, compared to PiZ mice given four biweekly intravenous (IV) doses of saline (FIG. 11).

TABLE 16

Average levels of soluble and insoluble Z-hAAT protein in liver lysate of PiZ mice normalized to saline-injected mice

| Treatment | Number animals | Soluble (normalized to saline control) | Insoluble polymer (normalized to saline control) |
|---|---|---|---|
| Baseline (5 weeks old) | 3 | 0.866 ± 0.105 | 0.478 ± 0.083 |
| Saline (13 weeks old) | 7 | 0.992 ± 0.138 | 1.010 ± 0.309 |
| Luc-UNA (13 weeks old) | 3 | 1.630 ± 0.162 | 1.192 ± 0.152 |
| SEQ ID 53/63 (13 weeks old) | 10 | 0.004 ± 0.013 | 0.209 ± 0.103 |

Figure 12:
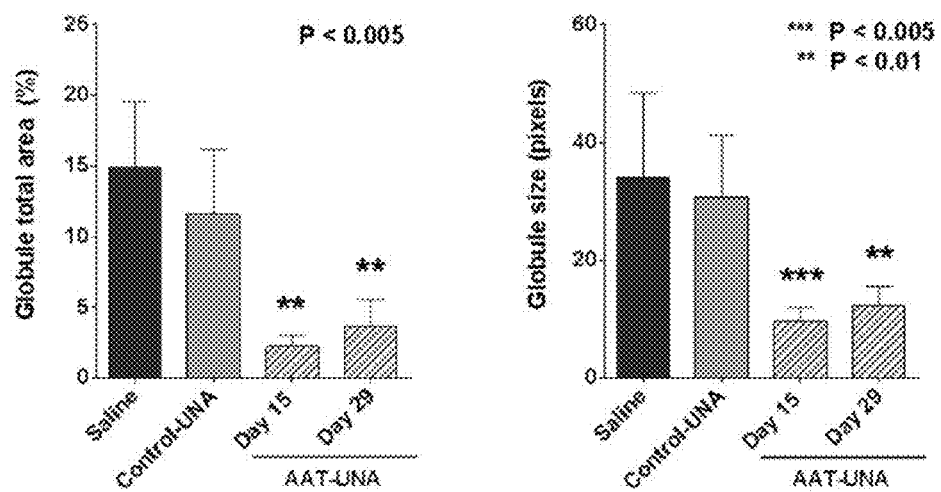
FIG. 12. Bar graph showing globule size in six month old female PiZ mice that received a single IV dose of saline, Luc-UNA RNAi trigger (8 mg/kg SEQ ID 59/78 with 8 mg/kg of MLP delivery polymer) or AAT-UNA RNAi trigger (8 mg/kg SEQ ID 52/63 with 8 mg/kg of MLP delivery polymer). The livers were sectioned, processed in formalin for histological observation, and stained with PAS-D for digital quantitation of the globule size and the area of the liver covered by globules.

Example 14. In Vivo Duration of Response from Single Injection of SEQ ID 52/63 RNAi Trigger in PiZ Mice A single IV dose of saline, 8 mg/kg Luc-UNA+8 mg/kg MLP delivery polymer, or 8 mg/kg AAT RNAi trigger SEQ ID 52/63+8 mg/kg MLP delivery polymer was administered to 6 month old female PiZ mice as described above. Human AAT protein levels in serum were monitored for 29 days. At the indicated times, blood samples were collected and assayed for hAAT by ELISA. Day 1 samples were collected prior to trigger administration. For mRNA analysis, 3-4 mice were euthanized at each of days 3, 8, 15, 22, and 29. For euthanized mice, cardic stick were performed for serum isolation for AAT ELISA (200 µl serum). Half of the left lateral liver lobe was collected and snap-freeze in liquid nitrogen for RNA isolation. The remainder of the left lobes were embedded into paraffin blocks for PAS-D staining with hematoxylin as counter-stain. Serum hAAT levels in mice given AAT RNAi trigger SEQ ID 52/63 were 95% reduced on day 8 and remained reduced to day 29, at which time they were 79% reduced. Mice given AAT RNAi trigger SEQ ID 52/63 were euthanized at either day 3, 8, 15, 22 or 29. Mice given saline or Luc-RNAi trigger (SEQ ID 59/78) were euthanized on day 29. Levels of hAAT mRNA in the livers were measured by RT-qPCR. The hAAT mRNA in mice given UNA SEQ ID 52/63 was reduced by 97% on day 3 and remained reduced on day 29, at which time levels were 56% reduced. The size of the globules and the area of the liver covered by globules was digitally quantitated from liver specimens stained with PAS-D. AAT-UNA treated mice had 70% smaller globules at day 15 and 62% smaller globules at day 29. The area of the liver covered with globules was 83% reduced on day 15 and 72% reduced on day 29 (FIG. 12).

TABLE 17

Serum hAAT levels in PiZ mice following administration of one injection of saline, Luc-RNAi trigger SEQ ID 59/78, or AAT RNAi trigger SEQ ID 52/63.

| Day euthanized | Treatment | Serum hAAT normalized to day 1 and controls | | | | | | |
|---|---|---|---|---|---|---|---|---|
| | | Day −2 | Day 1 | Day 3 | Day 8 | Day 15 | Day 22 | Day 29 |
| Day 29 | Saline | 1.000 ± 0.239 | 1.000 | 1.000 ± 0.368 | 1.000 ± 0.235 | 1.000 ± 0.097 | 1.000 ± 0.177 | 1.000 ± 0.272 |
| Day 29 | 8 mg/kg MLP delivery polymer + 8 mg/kg Luc-UNA | 1.268 ± 0.143 | 1.000 | 0.994 ± 0.153 | 1.090 ± 0.092 | 0.890 ± 0.080 | 1.171 ± 0.095 | 0.797 ± 0.074 |
| Day 3 | 8 mg/kg MLP delivery polymer + 8 mg/kg AAT-UNA | 1.068 ± 0.070 | 1.000 | 0.255 ± 0.040 | — | — | — | — |
| Day 8 | | 0.895 ± 0.129 | 1.000 | 0.184 ± 0.025 | 0.054 ± 0.004 | — | — | — |
| Day 15 | | 0.66 ± 0.121 | 1.000 | 0.243 ± 0.060 | 0.066 ± 0.023 | 0.095 ± 0.063 | — | — |
| Day 22 | | 0.779 ± 0.280 | 1.000 | 0.202 ± 0.054 | 0.044 ± 0.010 | 0.056 ± 0.011 | 0.100 ± 0.039 | — |
| Day 29 | | 0.653 ± 0.102 | 1.000 | 0.238 ± 0.062 | 0.052 ± 0.015 | 0.057 ± 0.016 | 0.103 ± 0.032 | 0.209 ± 0.071 |

TABLE 18

Relative hAAT mRNA levels in PiZ mice following administration of one injection of saline, Luc-RNAi trigger SEQ ID 59/78, or AAT RNAi trigger SEQ ID 52/63.

| Treatment | day | Average relative mRNA level | Low variance | High variance |
|---|---|---|---|---|
| Saline | 29 | 1.000 | 0.072 | 0.078 |
| 8 mg/kg Luc-RNAi trigger + 8 mg/kg MLP delivery polymer | 29 | 1.031 | 0.090 | 0.098 |
| 8 mg/kg mg/kg SEQ ID 52/63 + 8 mg/kg MLP delivery polymer | 3 | 0.030 | 0.007 | 0.009 |
|  | 8 | 0.032 | 0.014 | 0.024 |
|  | 15 | 0.158 | 0.060 | 0.096 |
|  | 22 | 0.221 | 0.033 | 0.038 |
|  | 29 | 0.439 | 0.057 | 0.066 |

Example 15. Alpha-1 Antitrypsin (AAT) Knockdown in Primate Following AAT RNA Trigger Molecule Delivery by MLP Delivery Polymer MLP delivery polymer and RNAi trigger were made and combined in a pharmaceutically acceptable buffer as described above. On day 1, cynomolgus macaque (*Macaca fascicularis*) primates (male and female, 3 to 9 kg) were co-injected with MLP delivery polymer and AAT UNA RNAi trigger SEQ ID 52/63 at different dose combinations. The dose combinations injected were: 2.0 mg/kg MLP delivery polymer+4.0 RNAi trigger (n=3), 3 mg/kg MLP delivery polymer+1.5 mg/kg RNAi trigger (n=2), 3.0 mg/kg MLP delivery polymer+3.0 mg/kg RNAi trigger (n=3), 3.0 mg/kg MLP delivery polymer+6.0 mg/kg RNAi trigger (n=2), 6.0 mg/kg MLP delivery polymer+12 mg/kgRNAi trigger (n=3) (0.050 s conversion factor used to determine RNAi trigger concentration) and 12 mg/kg MLP delivery polymer+6.0 mg/kg RNAi trigger (n=12). For each injection the MLP delivery polymer+RNAi trigger (2 ml/kg) was injected into the saphenous vein using a 22 to 25 gauge intravenous catheter. At the indicated time points, blood samples were drawn and analyzed for AAT and toxicity markers. Blood was collected from the femoral vein and primates were fasted overnight before all blood collections. Blood tests for blood urea nitrogen (BUN), alanine transaminase (ALT), aspartate aminotransferase (AST), and creatinine were performed on an automated chemistry analyzer at Meriter laboratories or BASi. AAT levels were determined on a Cobas Integra 400 (Roche Diagnostics) according to the manufacturer's recommendations. Significant knockdown of AAT was observed at all dose combinations. No toxicity was observed at doses with 2 mg/kg, 3 mg/kg or 6 mg/kg of MLP but at 12 mg/kg MLP there were elevations in liver enzymes (ALT and AST) as well as BUN and creatinine after injection.

TABLE 19

Percent AAT Knockdown in NHPs

| MLP (mg/kg) | SEQ ID 52/63 (mg/kg) | Pretest | Day 2 | 3 | 8 | 11 | 15 | 22 | 26 | 29 | 33 | 36 | 43 | 47 | 50 |
|---|---|---|---|---|---|---|---|---|---|---|---|---|---|---|---|
| 2.0 | 4.0 | 0 | 11 | 27 | 63 | 73 | 81 | 85 | — | 80 | — | | | | |
| 3.0 | 1.5 | 0 | 16 | 30 | 59 | 70 | 74 | 76 | — | 74 | — | 70 | 63 | — | 51 |
| 3.0 | 3.0 | 0 | 15 | 29 | 63 | 74 | 82 | 88 | — | 85 | — | | | | |
| 3.0 | 6.0 | 0 | 10 | 25 | 63 | 74 | 82 | | | | | | | | |
| 6.0 | 12.0 | 0 | 18 | 30 | 61 | | | | | | | | | | |
| 12.0 | 6.0 | 0 | 3 | 19 | 60 | 84 | 88 | — | 91 | — | 86 | — | — | 76 | |

TABLE 20

Urea nitrogen (mg/dL)

| MLP (mg/kg) | SEQ ID 52/63 (mg/kg) | Pretest | Day 2 | Day 3 | Day 8 |
|---|---|---|---|---|---|
| 2.0 | 4.0 | 20 | 21 | 20 | 20 |
| 3.0 | 1.5 | 18 | 21 | 18 | 20 |
| 3.0 | 3.0 | 18 | 18 | 18 | 16 |
| 3.0 | 6.0 | 22 | 22 | 23 | 22 |
| 6.0 | 12.0 | 16 | 18 | 15 | |
| 12.0 | 6.0 | 17 | 39 | 42 | 20 |

TABLE 21

Creatinine (mg/dL)

| MLP (mg/kg) | SEQ ID 52/63 (mg/kg) | Pretest | Day 2 | Day 3 | Day 8 |
|---|---|---|---|---|---|
| 2.0 | 4.0 | 0.88 | 0.9 | 0.94 | 0.89 |
| 3.0 | 1.5 | 0.81 | 0.8 | 0.85 | 0.81 |
| 3.0 | 3.0 | 0.7 | 0.77 | 0.83 | 0.72 |
| 3.0 | 6.0 | 0.82 | 0.92 | 0.99 | 0.84 |
| 6.0 | 12.0 | 0.6 | 0.66 | 0.67 | |
| 12.0 | 6.0 | 0.58 | 1.88 | 1.32 | 0.7 |

TABLE 22

Alanine transaminase (U/L)

| MLP (mg/kg) | SEQ ID 52/63 (mg/kg) | Pretest | Day 2 | Day 3 | Day 8 |
|---|---|---|---|---|---|
| 2.0 | 4.0 | 44 | 52 | 58 | 47 |
| 3.0 | 1.5 | 56 | 62 | 65 | 56 |
| 3.0 | 3.0 | 34 | 54 | 54 | 35 |
| 3.0 | 6.0 | 43 | 54 | 53 | 39 |
| 6.0 | 12.0 | 41 | 52 | 47 | |
| 12.0 | 6.0 | 48 | 81 | 60 | 33 |

TABLE 23

Aspartate aminotransferase (U/L)

| MLP delivery polymer (mg/kg) | SEQ ID 52/63 (mg/kg) | Pretest | Day 2 | Day 3 | Day 8 |
|---|---|---|---|---|---|
| 2.0 | 4.0 | 28 | 48 | 54 | 30 |
| 3.0 | 1.5 | 49 | 58 | 54 | 35 |
| 3.0 | 3.0 | 27 | 67 | 57 | 28 |
| 3.0 | 6.0 | 35 | 58 | 51 | 29 |
| 6.0 | 12.0 | 34 | 46 | 33 | |
| 12.0 | 6.0 | 29 | 249 | 89 | 55 |

Example 16. Repeat Administration

Figure 13:
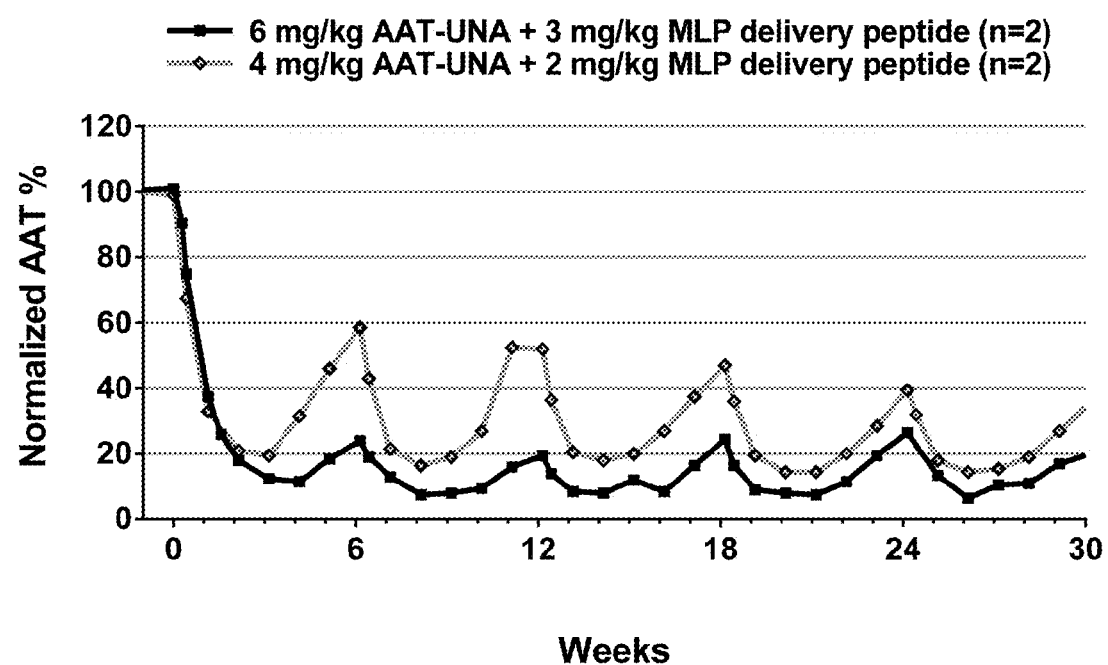
FIG. 13. Graph showing AAT knockdown following repeat administration in primates with AAT-RNAi trigger and MLP delivery polymer. Two monkeys each were given 2.0 mg/kg MLP delivery polymer (MLP delivery peptide)+ 4.0 AAT-RNAi trigger SEQ ID 52/63 (AAT-UNA) or 3 mg/kg MLP delivery polymer (MLP delivery peptide)+6 mg/kg RNAi trigger SEQ ID 52/63 (AAT-UNA). The first dose was at day 1. Doses were all six weeks apart.

Cynomolgus macaque primates were given five doses of RNAi trigger+MLP delivery polymer at six week intervals. Each dose contained MLP delivery polymer and AAT-RNAi trigger SEQ ID 52/63 at a 1:2 weight to weight ratio of the MLP to RNAi trigger. The first injection was on day 1. The dose combinations injected were: 2.0 mg/kg MLP delivery polymer+4.0 RNAi trigger (n=2) and 3 mg/kg MLP delivery polymer+6 mg/kg RNAi trigger (n=2). Blood was collected at intervals throughout the study and AAT levels were measured from the serum as described. Repeat dosing at six week intervals reduced serum AAT levels by approximately 80-90% from two to thirty weeks after the first treatment of 3 mg/kg MLP delivery polymer+6 mg/kg RNAi trigger in the primates. Serum AAT was reduced by 80% following the first treatment of primates with 2.0 mg/kg MLP delivery polymer+4.0 RNAi trigger and by 85% following the fourth treatment. Serum AAT levels measured six weeks after each treatment with 2.0 mg/kg MLP delivery polymer+4.0 RNAi trigger rebounded less with each additional treatment (FIG. 13).

The invention claimed is:

1. An RNA interference (RNAi) trigger molecule for inhibiting the expression of an alpha-1 antitrypsin gene in a cell in vivo, wherein the RNAi trigger molecule comprises a sense strand sequence that is 18-24 nucleotides in length and an antisense strand sequence that is 19-24 nucleotides in length, wherein the antisense strand sequence and the sense strand sequence are fully complementary over a core stretch of at least 18 consecutive nucleotides, wherein the antisense strand sequence comprises in order the nucleobase sequence 5' GGAACUUGGUGAUGAUAU 3' (SEQ ID NO: 1), and wherein said SEQ ID NO: 1 is located at nucleotide positions 2-19 from the 5' terminal end of the antisense strand.

2. The RNAi trigger molecule of claim 1, wherein the sense strand or the antisense strand further comprises a 3' extension of 1-5 nucleotides in length.

3. The RNAi trigger molecule of claim 2, wherein the 3' extension of the antisense strand comprises dTdT or dTsdT, wherein dT is a deoxythymidine nucleotide and s is a phosphorothioate internucleoside linkage.

4. The RNAi trigger molecule of claim 3, wherein the 3' extension of the sense strand comprises Af(invdT), wherein Af is a 2'-deoxy-2'-fluoro adenosine nucleotide, and (invdT) is an inverted deoxythymidine (3'-3'-linked) nucleotide.

5. The RNAi trigger molecule of claim 1, wherein the sense strand further comprises a 5' extension of 1-5 nucleotides in length.

6. The RNAi trigger molecule of claim 5, wherein the 5' extension of the antisense strand comprises deoxythymidine.

7. The RNAi trigger molecule of claim 5, wherein the 5' extension of the sense strand comprises UAU or uAu, wherein U is uracil, A is adenine, and u is 2'-O-methyl modified uracil.

8. The RNAi trigger molecule of claim 1, wherein a targeting moiety is conjugated to the 5' end of the sense strand.

9. The RNAi trigger molecule of claim 8, wherein the targeting moiety comprises N-acetyl-galactosamine.

10. The RNAi trigger molecule of claim 8, wherein the targeting moiety comprises a cholesterol-triethylene glycol group.

11. The RNAi trigger molecule of claim 1, wherein the sense strand sequence and antisense strand sequence form a sequence pair consisting of SEQ ID NOs: 1/8.

12. The RNAi trigger molecule of claim 2, wherein the sense strand sequence and antisense strand sequence form sequence pairs or meroduplexes selected from the group consisting of SEQ ID NOs: 15/23, 15/24, 15/25/41, 15/26/42, and 15/27/43.

13. The RNAi trigger molecule of claim 1, wherein the sense strand or antisense strand contains one or more modified nucleotide or nucleotide mimic.

14. The RNAi trigger molecule of claim 13, wherein the sense strand sequence and antisense strand sequence form sequence pairs selected from the group consisting of SEQ ID NOs: 50/62 and 50/63.

15. The RNAi trigger molecule of claim 13, wherein the sense strand sequence and antisense sequence form sequence meroduplexes selected from the group consisting of SEQ ID NOs: 50/64/81, 50/65/82, and 50/66/83.

16. The RNAi trigger molecule of claim 13, wherein the antisense strand sequence contains at least one 2',3'-seco RNA nucleotide mimic.

17. The RNAi trigger molecule of claim 13, wherein the sense strand sequence and antisense strand sequence form a sequence pair consisting of SEQ ID NOs: 52/63.

18. The RNAi trigger molecule of claim 13, wherein the modified nucleotide is selected from the group consisting of: a 2'-O-methyl modified nucleotide, a nucleotide comprising a 5'-phosphorothioate group, a 2'-deoxy-2'-fluoro modified nucleotide, a 2'-deoxy-modified nucleotide, a locked nucleotide, an abasic nucleotide, a deoxythymidine, an inverted deoxythymidine, a 2'-amino-modified nucleotide, a 2'-alkyl-modified nucleotide, a morpholino nucleotide, a phosphorothioate linked nucleotide, and a non-natural base comprising nucleotide.

19. A composition comprising the RNAi trigger molecule as defined in claim 13.

20. The composition of claim 19, further comprising a pharmaceutically acceptable carrier, stabilizer and/or diluent.

21. A method for inhibiting the expression of an alpha-1 antitrypsin (AAT) gene in a cell, a tissue, or an organism, the method comprising introducing into a cell, tissue, or organism the RNAi trigger molecule as defined in claim 13.

22. The method of claim 21, wherein inhibiting expression of an AAT gene in an organism treats, or manages a pathological condition or disease caused by alpha-1 antitrypsin deficiency.

23. The method claim 22, wherein the pathological condition and disease caused by alpha-1 antitrypsin deficiency is selected from the group consisting of: chronic hepatitis, cirrhosis, hepatocellular carcinoma, and fulminant hepatic failure.

24. The RNAi trigger molecule of claim 16, wherein the sense strand sequence and antisense strand sequence form a sequence pair consisting of SEQ ID NOs: 51/63.

25. The composition of claim 19, further comprising a melittin-like protein (MLP) delivery polymer.

* * * * *

```
                        SEQUENCE LISTING

<160> NUMBER OF SEQ ID NOS: 184

<210> SEQ ID NO 1
<211> LENGTH: 18
<212> TYPE: RNA
<213> ORGANISM: Artificial Sequence
<220> FEATURE:
<223> OTHER INFORMATION: antisense strand of dsRNA

<400> SEQUENCE: 1
ggaacuuggu gaugauau                                                   18

<210> SEQ ID NO 2
<211> LENGTH: 18
<212> TYPE: RNA
<213> ORGANISM: Artificial Sequence
<220> FEATURE:
<223> OTHER INFORMATION: antisense strand of dsRNA

<400> SEQUENCE: 2
gaucauaggu uccaguaa                                                   18

<210> SEQ ID NO 3
<211> LENGTH: 18
<212> TYPE: RNA
<213> ORGANISM: Artificial Sequence
<220> FEATURE:
<223> OTHER INFORMATION: antisense strand of dsRNA

<400> SEQUENCE: 3
acagccuuau gcacggcc                                                   18

<210> SEQ ID NO 4
<211> LENGTH: 18
<212> TYPE: RNA
<213> ORGANISM: Artificial Sequence
<220> FEATURE:
```

```
<223> OTHER INFORMATION: antisense strand of dsRNA

<400> SEQUENCE: 4
ucgaugguca gcacagcc                                                 18

<210> SEQ ID NO 5
<211> LENGTH: 18
<212> TYPE: RNA
<213> ORGANISM: Artificial Sequence
<220> FEATURE:
<223> OTHER INFORMATION: antisense strand of dsRNA

<400> SEQUENCE: 5
caaaggguuu guugaacu                                                 18

<210> SEQ ID NO 6
<211> LENGTH: 18
<212> TYPE: RNA
<213> ORGANISM: Artificial Sequence
<220> FEATURE:
<223> OTHER INFORMATION: antisense strand of dsRNA

<400> SEQUENCE: 6
cgaaguacuc agcguaag                                                 18

<210> SEQ ID NO 7
<211> LENGTH: 18
<212> TYPE: RNA
<213> ORGANISM: Artificial Sequence
<220> FEATURE:
<223> OTHER INFORMATION: antisense strand of dsRNA

<400> SEQUENCE: 7
gaguuggcac gccuuugc                                                 18

<210> SEQ ID NO 8
<211> LENGTH: 18
<212> TYPE: RNA
<213> ORGANISM: Artificial Sequence
<220> FEATURE:
<223> OTHER INFORMATION: sense strand of dsRNA

<400> SEQUENCE: 8
auaucaucac caaguucc                                                 18

<210> SEQ ID NO 9
<211> LENGTH: 18
<212> TYPE: RNA
<213> ORGANISM: Artificial Sequence
<220> FEATURE:
<223> OTHER INFORMATION: sense strand of dsRNA

<400> SEQUENCE: 9
uuacuggaac cuaugauc                                                 18

<210> SEQ ID NO 10
<211> LENGTH: 18
<212> TYPE: RNA
<213> ORGANISM: Artificial Sequence
<220> FEATURE:
<223> OTHER INFORMATION: sense strand of dsRNA

<400> SEQUENCE: 10
ggccgugcau aaggcugu                                                 18
```

```
<210> SEQ ID NO 11
<211> LENGTH: 18
<212> TYPE: RNA
<213> ORGANISM: Artificial Sequence
<220> FEATURE:
<223> OTHER INFORMATION: sense strand of dsRNA

<400> SEQUENCE: 11
ggcugugcug accaucga                                                 18

<210> SEQ ID NO 12
<211> LENGTH: 18
<212> TYPE: RNA
<213> ORGANISM: Artificial Sequence
<220> FEATURE:
<223> OTHER INFORMATION: sense strand of dsRNA

<400> SEQUENCE: 12
aguucaacaa acccuuug                                                 18

<210> SEQ ID NO 13
<211> LENGTH: 19
<212> TYPE: RNA
<213> ORGANISM: Artificial Sequence
<220> FEATURE:
<223> OTHER INFORMATION: sense strand of dsRNA

<400> SEQUENCE: 13
cuuacgcuga guacuucga                                                19

<210> SEQ ID NO 14
<211> LENGTH: 19
<212> TYPE: RNA
<213> ORGANISM: Artificial Sequence
<220> FEATURE:
<223> OTHER INFORMATION: sense strand of dsRNA

<400> SEQUENCE: 14
gcaaaggcgu gccaacuca                                                19

<210> SEQ ID NO 15
<211> LENGTH: 21
<212> TYPE: DNA
<213> ORGANISM: Artificial Sequence
<220> FEATURE:
<223> OTHER INFORMATION: antisense strand of dsRNA
<220> FEATURE:
<221> NAME/KEY: modified_base
<222> LOCATION: (2)..(19)
<223> OTHER INFORMATION: /mod_base = "2'-hydroxy corresponding
      nucleoside"

<400> SEQUENCE: 15
tggaacuugg ugaugauaut t                                             21

<210> SEQ ID NO 16
<211> LENGTH: 21
<212> TYPE: DNA
<213> ORGANISM: Artificial Sequence
<220> FEATURE:
<223> OTHER INFORMATION: antisense strand of dsRNA
<220> FEATURE:
<221> NAME/KEY: modified_base
<222> LOCATION: (2)..(19)
<223> OTHER INFORMATION: /mod_base = "2'-hydroxy corresponding
      nucleoside"

<400> SEQUENCE: 16
```
tgaucauagg uuccaguaat t                            21

<210> SEQ ID NO 17
<211> LENGTH: 21
<212> TYPE: DNA
<213> ORGANISM: Artificial Sequence
<220> FEATURE:
<223> OTHER INFORMATION: antisense strand of dsRNA
<220> FEATURE:
<221> NAME/KEY: modified_base
<222> LOCATION: (2)..(19)
<223> OTHER INFORMATION: /mod_base = "2'-hydroxy corresponding
      nucleoside"

<400> SEQUENCE: 17
tacagccuua ugcacggcct t                            21

<210> SEQ ID NO 18
<211> LENGTH: 21
<212> TYPE: DNA
<213> ORGANISM: Artificial Sequence
<220> FEATURE:
<223> OTHER INFORMATION: antisense strand of dsRNA
<220> FEATURE:
<221> NAME/KEY: modified_base
<222> LOCATION: (2)..(19)
<223> OTHER INFORMATION: /mod_base = "2'-hydroxy corresponding
      nucleoside"

<400> SEQUENCE: 18
tucgaugguc agcacagcct t                            21

<210> SEQ ID NO 19
<211> LENGTH: 21
<212> TYPE: DNA
<213> ORGANISM: Artificial Sequence
<220> FEATURE:
<223> OTHER INFORMATION: antisense strand of dsRNA
<220> FEATURE:
<221> NAME/KEY: modified_base
<222> LOCATION: (2)..(19)
<223> OTHER INFORMATION: /mod_base = "2'-hydroxy corresponding
      nucleoside"

<400> SEQUENCE: 19 tcaaagguu uguugaacut t                             21

<210> SEQ ID NO 20
<211> LENGTH: 21
<212> TYPE: DNA
<213> ORGANISM: Artificial Sequence
<220> FEATURE:
<223> OTHER INFORMATION: antisense strand of dsRNA
<220> FEATURE:
<221> NAME/KEY: modified_base
<222> LOCATION: (2)..(19)
<223> OTHER INFORMATION: /mod_base = "2'-hydroxy corresponding
      nucleoside"

<400> SEQUENCE: 20
tcgaaguacu cagcguaagt t                            21

<210> SEQ ID NO 21
<211> LENGTH: 21
<212> TYPE: DNA
<213> ORGANISM: Artificial Sequence
<220> FEATURE:
<223> OTHER INFORMATION: antisense strand of dsRNA
<220> FEATURE:
<221> NAME/KEY: modified_base

```
<222> LOCATION: (1)..(19)
<223> OTHER INFORMATION: /mod_base = "2'-hydroxy corresponding
      nucleoside"

<400> SEQUENCE: 21
ucgaaguacu cagcguaagt t                                              21

<210> SEQ ID NO 22
<211> LENGTH: 21
<212> TYPE: DNA
<213> ORGANISM: Artificial Sequence
<220> FEATURE:
<223> OTHER INFORMATION: antisense strand of dsRNA
<220> FEATURE:
<221> NAME/KEY: modified_base
<222> LOCATION: (2)..(19)
<223> OTHER INFORMATION: /mod_base = "2'-hydroxy corresponding
      nucleoside"

<400> SEQUENCE: 22
tgaguuggca cgccuuugct t                                              21

<210> SEQ ID NO 23
<211> LENGTH: 20
<212> TYPE: DNA
<213> ORGANISM: Artificial Sequence
<220> FEATURE:
<223> OTHER INFORMATION: sense strand of dsRNA
<220> FEATURE:
<221> NAME/KEY: modified_base
<222> LOCATION: (1)..(19)
<223> OTHER INFORMATION: /mod_base = "2'-hydroxy corresponding
      nucleoside"

<400> SEQUENCE: 23
auaucaucac caaguuccat                                                20

<210> SEQ ID NO 24
<211> LENGTH: 23
<212> TYPE: DNA
<213> ORGANISM: Artificial Sequence
<220> FEATURE:
<223> OTHER INFORMATION: sense strand of dsRNA
<220> FEATURE:
<221> NAME/KEY: modified_base
<222> LOCATION: (1)..(22)
<223> OTHER INFORMATION: /mod_base = "2'-hydroxy corresponding
      nucleoside"

<400> SEQUENCE: 24
uauauaucau caccaaguuc cat                                            23

<210> SEQ ID NO 25
<211> LENGTH: 12
<212> TYPE: RNA
<213> ORGANISM: Artificial Sequence
<220> FEATURE:
<223> OTHER INFORMATION: sense strand of dsRNA

<400> SEQUENCE: 25
uauauaucau ca                                                        12

<210> SEQ ID NO 26
<211> LENGTH: 13
<212> TYPE: RNA
<213> ORGANISM: Artificial Sequence
<220> FEATURE:
<223> OTHER INFORMATION: sense strand of dsRNA
```

```
<400> SEQUENCE: 26
uauauaucau cac                                                         13

<210> SEQ ID NO 27
<211> LENGTH: 14
<212> TYPE: RNA
<213> ORGANISM: Artificial Sequence
<220> FEATURE:
<223> OTHER INFORMATION: sense strand of dsRNA

<400> SEQUENCE: 27
uauauaucau cacc                                                        14

<210> SEQ ID NO 28
<211> LENGTH: 20
<212> TYPE: DNA
<213> ORGANISM: Artificial Sequence
<220> FEATURE:
<223> OTHER INFORMATION: sense strand of dsRNA
<220> FEATURE:
<221> NAME/KEY: modified_base
<222> LOCATION: (1)..(19)
<223> OTHER INFORMATION: /mod_base = "2'-hydroxy corresponding
      nucleoside"

<400> SEQUENCE: 28
uuacuggaac cuaugaucat                                                  20

<210> SEQ ID NO 29
<211> LENGTH: 13
<212> TYPE: RNA
<213> ORGANISM: Artificial Sequence
<220> FEATURE:
<223> OTHER INFORMATION: sense strand of dsRNA

<400> SEQUENCE: 29
uauuuacugg aac                                                         13

<210> SEQ ID NO 30
<211> LENGTH: 20
<212> TYPE: DNA
<213> ORGANISM: Artificial Sequence
<220> FEATURE:
<223> OTHER INFORMATION: sense strand of dsRNA
<220> FEATURE:
<221> NAME/KEY: modified_base
<222> LOCATION: (1)..(19)
<223> OTHER INFORMATION: /mod_base = "2'-hydroxy corresponding
      nucleoside"

<400> SEQUENCE: 30
ggccgugcau aaggcuguat                                                  20

<210> SEQ ID NO 31
<211> LENGTH: 20
<212> TYPE: DNA
<213> ORGANISM: Artificial Sequence
<220> FEATURE:
<223> OTHER INFORMATION: sense strand of dsRNA
<220> FEATURE:
<221> NAME/KEY: modified_base
<222> LOCATION: (1)..(19)
<223> OTHER INFORMATION: /mod_base = "2'-hydroxy corresponding
      nucleoside"

<400> SEQUENCE: 31 ggcugugcuga ccaucgaat                                                  20
```

-continued

```
<210> SEQ ID NO 32
<211> LENGTH: 12
<212> TYPE: RNA
<213> ORGANISM: Artificial Sequence
<220> FEATURE:
<223> OTHER INFORMATION: sense strand of dsRNA

<400> SEQUENCE: 32
uauggcugug cu                                                            12

<210> SEQ ID NO 33
<211> LENGTH: 13
<212> TYPE: RNA
<213> ORGANISM: Artificial Sequence
<220> FEATURE:
<223> OTHER INFORMATION: sense strand of dsRNA

<400> SEQUENCE: 33
uauggcugug cug                                                           13

<210> SEQ ID NO 34
<211> LENGTH: 14
<212> TYPE: RNA
<213> ORGANISM: Artificial Sequence
<220> FEATURE:
<223> OTHER INFORMATION: sense strand of dsRNA

<400> SEQUENCE: 34
uauggcugug cuga                                                          14

<210> SEQ ID NO 35
<211> LENGTH: 11
<212> TYPE: RNA
<213> ORGANISM: Artificial Sequence
<220> FEATURE:
<223> OTHER INFORMATION: sense strand of dsRNA

<400> SEQUENCE: 35
uauggcugug c                                                             11

<210> SEQ ID NO 36
<211> LENGTH: 20
<212> TYPE: DNA
<213> ORGANISM: Artificial Sequence
<220> FEATURE:
<223> OTHER INFORMATION: sense strand of dsRNA
<220> FEATURE:
<221> NAME/KEY: modified_base
<222> LOCATION: (1)..(19)
<223> OTHER INFORMATION: /mod_base = "2'-hydroxy corresponding
      nucleoside"

<400> SEQUENCE: 36
aguucaacaa acccuuugat                                                    20

<210> SEQ ID NO 37
<211> LENGTH: 14
<212> TYPE: RNA
<213> ORGANISM: Artificial Sequence
<220> FEATURE:
<223> OTHER INFORMATION: sense strand of dsRNA

<400> SEQUENCE: 37
uauaguucaa caaa                                                          14

<210> SEQ ID NO 38
```

```
<211> LENGTH: 23
<212> TYPE: DNA
<213> ORGANISM: Artificial Sequence
<220> FEATURE:
<223> OTHER INFORMATION: sense strand of dsRNA
<220> FEATURE:
<221> NAME/KEY: modified_base
<222> LOCATION: (1)..(22)
<223> OTHER INFORMATION: /mod_base = "2'-hydroxy corresponding
      nucleoside"

<400> SEQUENCE: 38
uauaguucaa caaacccuuu gat                                            23

<210> SEQ ID NO 39
<211> LENGTH: 23
<212> TYPE: DNA
<213> ORGANISM: Artificial Sequence
<220> FEATURE:
<223> OTHER INFORMATION: sense strand of dsRNA
<220> FEATURE:
<221> NAME/KEY: modified_base
<222> LOCATION: (1)..(22)
<223> OTHER INFORMATION: /mod_base = "2'-hydroxy corresponding
      nucleoside"

<400> SEQUENCE: 39 uaucuuacgcu gaguacuuc gat                                            23

<210> SEQ ID NO 40
<211> LENGTH: 23
<212> TYPE: DNA
<213> ORGANISM: Artificial Sequence
<220> FEATURE:
<223> OTHER INFORMATION: sense strand of dsRNA
<220> FEATURE:
<221> NAME/KEY: modified_base
<222> LOCATION: (1)..(22)
<223> OTHER INFORMATION: /mod_base = "2'-hydroxy corresponding
      nucleoside"

<400> SEQUENCE: 40
uaugcaaagg cgugccaacu cat                                            23

<210> SEQ ID NO 41
<211> LENGTH: 11
<212> TYPE: DNA
<213> ORGANISM: Artificial Sequence
<220> FEATURE:
<223> OTHER INFORMATION: sense strand of dsRNA
<220> FEATURE:
<221> NAME/KEY: modified_base
<222> LOCATION: (1)..(10)
<223> OTHER INFORMATION: /mod_base = "2'-hydroxy corresponding
      nucleoside"

<400> SEQUENCE: 41
ccaaguucca t                                                         11

<210> SEQ ID NO 42
<211> LENGTH: 10
<212> TYPE: DNA
<213> ORGANISM: Artificial Sequence
<220> FEATURE:
<223> OTHER INFORMATION: sense strand of dsRNA
<220> FEATURE:
<221> NAME/KEY: modified_base
<222> LOCATION: (1)..(9)
<223> OTHER INFORMATION: /mod_base = "2'-hydroxy corresponding
      nucleoside"
```

```
<400> SEQUENCE: 42
caaguuccat                                                              10

<210> SEQ ID NO 43
<211> LENGTH: 9
<212> TYPE: DNA
<213> ORGANISM: Artificial Sequence
<220> FEATURE:
<223> OTHER INFORMATION: sense strand of dsRNA
<220> FEATURE:
<221> NAME/KEY: modified_base
<222> LOCATION: (1)..(8)
<223> OTHER INFORMATION: /mod_base = "2'-hydroxy corresponding
      nucleoside"

<400> SEQUENCE: 43 aaguuccat                                                                9

<210> SEQ ID NO 44
<211> LENGTH: 10
<212> TYPE: DNA
<213> ORGANISM: Artificial Sequence
<220> FEATURE:
<223> OTHER INFORMATION: sense strand of dsRNA
<220> FEATURE:
<221> NAME/KEY: modified_base
<222> LOCATION: (1)..(9)
<223> OTHER INFORMATION: /mod_base = "2'-hydroxy corresponding
      nucleoside"

<400> SEQUENCE: 44
cuaugaucat                                                              10

<210> SEQ ID NO 45
<211> LENGTH: 11
<212> TYPE: DNA
<213> ORGANISM: Artificial Sequence
<220> FEATURE:
<223> OTHER INFORMATION: sense strand of dsRNA
<220> FEATURE:
<221> NAME/KEY: modified_base
<222> LOCATION: (1)..(10)
<223> OTHER INFORMATION: /mod_base = "2'-hydroxy corresponding
      nucleoside"

<400> SEQUENCE: 45
gaccaucgaa t                                                            11

<210> SEQ ID NO 46
<211> LENGTH: 10
<212> TYPE: DNA
<213> ORGANISM: Artificial Sequence
<220> FEATURE:
<223> OTHER INFORMATION: sense strand of dsRNA
<220> FEATURE:
<221> NAME/KEY: modified_base
<222> LOCATION: (1)..(9)
<223> OTHER INFORMATION: /mod_base = "2'-hydroxy corresponding
      nucleoside"

<400> SEQUENCE: 46
accaucgaat                                                              10

<210> SEQ ID NO 47
<211> LENGTH: 9
<212> TYPE: DNA
<213> ORGANISM: Artificial Sequence
<220> FEATURE:
<223> OTHER INFORMATION: sense strand of dsRNA
```

```
<220> FEATURE:
<221> NAME/KEY: modified_base
<222> LOCATION: (1)..(8)
<223> OTHER INFORMATION: /mod_base = "2'-hydroxy corresponding
      nucleoside"

<400> SEQUENCE: 47 ccaucgaat                                                                  9

<210> SEQ ID NO 48
<211> LENGTH: 12
<212> TYPE: DNA
<213> ORGANISM: Artificial Sequence
<220> FEATURE:
<223> OTHER INFORMATION: sense strand of dsRNA
<220> FEATURE:
<221> NAME/KEY: modified_base
<222> LOCATION: (1)..(11)
<223> OTHER INFORMATION: /mod_base = "2'-hydroxy corresponding
      nucleoside"

<400> SEQUENCE: 48
ugaccaucga at                                                             12

<210> SEQ ID NO 49
<211> LENGTH: 9
<212> TYPE: DNA
<213> ORGANISM: Artificial Sequence
<220> FEATURE:
<223> OTHER INFORMATION: sense strand of dsRNA
<220> FEATURE:
<221> NAME/KEY: modified_base
<222> LOCATION: (1)..(8)
<223> OTHER INFORMATION: /mod_base = "2'-hydroxy corresponding
      nucleoside"

<400> SEQUENCE: 49 cccuuugat                                                                  9

<210> SEQ ID NO 50
<211> LENGTH: 21
<212> TYPE: DNA
<213> ORGANISM: Artificial Sequence
<220> FEATURE:
<223> OTHER INFORMATION: antisense strand of dsRNA
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 50
tggaacuugg ugaugauaut t                                                   21

<210> SEQ ID NO 51
<211> LENGTH: 21
<212> TYPE: DNA
<213> ORGANISM: Artificial Sequence
<220> FEATURE:
<223> OTHER INFORMATION: antisense strand of dsRNA
<220> FEATURE:
```

```
<221> NAME/KEY: modified_base
<222> LOCATION: 6
<223> OTHER INFORMATION: /mod_base = "2'-3' seco corresponding
      nucleotide"
<220> FEATURE:
<221> NAME/KEY: modified_base
<222> LOCATION: 2,4,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 51
tggaacuugg ugaugauaut t                                              21

<210> SEQ ID NO 52
<211> LENGTH: 21
<212> TYPE: DNA
<213> ORGANISM: Artificial Sequence
<220> FEATURE:
<223> OTHER INFORMATION: antisense strand of dsRNA
<220> FEATURE:
<221> NAME/KEY: modified_base
<222> LOCATION: 7
<223> OTHER INFORMATION: /mod_base = "2'-3' seco corresponding
      nucleotide"
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 52
tggaacuugg ugaugauaut t                                              21

<210> SEQ ID NO 53
<211> LENGTH: 21
<212> TYPE: DNA
<213> ORGANISM: Artificial Sequence
<220> FEATURE:
<223> OTHER INFORMATION: antisense strand of dsRNA
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"
```

-continued

<400> SEQUENCE: 53
tgaucauagg uuccaguaat t                                              21

<210> SEQ ID NO 54
<211> LENGTH: 21
<212> TYPE: DNA
<213> ORGANISM: Artificial Sequence
<220> FEATURE:
<223> OTHER INFORMATION: antisense strand of dsRNA
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 54
tacagccuua ugcacggcct t                                              21

<210> SEQ ID NO 55
<211> LENGTH: 21
<212> TYPE: DNA
<213> ORGANISM: Artificial Sequence
<220> FEATURE:
<223> OTHER INFORMATION: antisense strand of dsRNA
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 55
tucgaugguc agcacagcct t                                              21

<210> SEQ ID NO 56
<211> LENGTH: 21
<212> TYPE: DNA
<213> ORGANISM: Artificial Sequence
<220> FEATURE:
<223> OTHER INFORMATION: antisense strand of dsRNA
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding nucleotide"

<400> SEQUENCE: 56 tcaaagggtuu uguugaacut t                                           21

<210> SEQ ID NO 57
<211> LENGTH: 21
<212> TYPE: DNA
<213> ORGANISM: Artificial Sequence
<220> FEATURE:
<223> OTHER INFORMATION: antisense strand of dsRNA
<220> FEATURE:
<221> NAME/KEY: modified_base
<222> LOCATION: 6
<223> OTHER INFORMATION: /mod_base = "2'-3' seco corresponding
      nucleotide"
<220> FEATURE:
<221> NAME/KEY: modified_base
<222> LOCATION: 2,4,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 57 tcaaagggtuu uguugaacut t                                           21

<210> SEQ ID NO 58
<211> LENGTH: 21
<212> TYPE: DNA
<213> ORGANISM: Artificial Sequence
<220> FEATURE:
<223> OTHER INFORMATION: antisense strand of dsRNA
<220> FEATURE:
<221> NAME/KEY: modified_base
<222> LOCATION: 7
<223> OTHER INFORMATION: /mod_base = "2'-3' seco corresponding
      nucleotide"
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 58 tcaaagggtuu uguugaacut t                                           21

<210> SEQ ID NO 59
<211> LENGTH: 21
<212> TYPE: DNA
<213> ORGANISM: Artificial Sequence
<220> FEATURE:
<223> OTHER INFORMATION: antisense strand of dsRNA
<220> FEATURE:
<221> NAME/KEY: modified_base

```
<222> LOCATION: 7
<223> OTHER INFORMATION: /mod_base = "2'-3' seco corresponding
      nucleotide"
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate corresponding
      nucleotide"

<400> SEQUENCE: 59
tcgaaguacu cagcguaagt t                                              21

<210> SEQ ID NO 60
<211> LENGTH: 21
<212> TYPE: DNA
<213> ORGANISM: Artificial Sequence
<220> FEATURE:
<223> OTHER INFORMATION: antisense strand of dsRNA
<220> FEATURE:
<221> NAME/KEY: modified_base
<222> LOCATION: 1,2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 2,21
<223> OTHER INFORMATION: /mod_base = "5'-phosphorothioate corresponding
      nucleotide"

<400> SEQUENCE: 60
ucgaaguacu cagcguaagt t                                              21

<210> SEQ ID NO 61
<211> LENGTH: 21
<212> TYPE: DNA
<213> ORGANISM: Artificial Sequence
<220> FEATURE:
<223> OTHER INFORMATION: antisense strand of dsRNA
<220> FEATURE:
<221> NAME/KEY: modified_base
<222> LOCATION: 2,4,6,8,10,12,14,16,18
<223> OTHER INFORMATION: /mod_base = "2'-deoxy-2'-fluoro corresponding
      nucleoside"
<220> FEATURE:
<221> NAME/KEY: modified_base
<222> LOCATION: 3,5,7,9,11,13,15,17,19
<223> OTHER INFORMATION: /mod_base = "2'-O-methyl corresponding
      nucleoside"
<220> FEATURE:
<221> NAME/KEY: modified_base
<222> LOCATION: 2,21
<223> OTHER INFORMATION: /mod_base = "5'-phosphorothioate corresponding
      nucleotide"

<400> SEQUENCE: 61
tgaguuggca cgccuuugct t                                              21

<210> SEQ ID NO 62
```

```
<211> LENGTH: 20
<212> TYPE: DNA
<213> ORGANISM: Artificial Sequence
<220> FEATURE:
<223> OTHER INFORMATION: sense strand of dsRNA
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked deoxythymidine"

<400> SEQUENCE: 62
auaucaucac caaguuccat                                                   20

<210> SEQ ID NO 63
<211> LENGTH: 23
<212> TYPE: DNA
<213> ORGANISM: Artificial Sequence
<220> FEATURE:
<223> OTHER INFORMATION: sense strand of dsRNA
<220> FEATURE:
<221> NAME/KEY: modified_base
<222> LOCATION: 2
<223> OTHER INFORMATION: /mod_base = "2'-hydroxy corresponding
      nucleoside"
<220> FEATURE:
<221> NAME/KEY: modified_base
<222> LOCATION: 4,6,8,10,12,14,16,18,20,22
<223> OTHER INFORMATION: /mod_base = "2'-deoxy-2'-fluoro corresponding
      nucleoside"
<220> FEATURE:
<221> NAME/KEY: modified_base
<222> LOCATION: 1,3,5,7,9,11,13,15,17,19,21
<223> OTHER INFORMATION: /mod_base = "2'-O-methyl corresponding
      nucleoside"
<220> FEATURE:
<221> NAME/KEY: modified_base
<222> LOCATION: 23
<223> OTHER INFORMATION: /mod_base = "3'-3'-linked deoxythymidine"
<220> FEATURE:
<221> NAME/KEY: modified_base
<222> LOCATION: 1
<223> OTHER INFORMATION: /mod_base = "Cholesterol-TEG modified
      corresponding nucleotide"

<400> SEQUENCE: 63
uauauaucau caccaaguuc cat                                               23

<210> SEQ ID NO 64
<211> LENGTH: 12
<212> TYPE: RNA
<213> ORGANISM: Artificial Sequence
<220> FEATURE:
<223> OTHER INFORMATION: sense strand of dsRNA
<220> FEATURE:
<221> NAME/KEY: modified_base
<222> LOCATION: 2
<223> OTHER INFORMATION: /mod_base = "2'-hydroxy corresponding
      nucleoside"
<220> FEATURE:
<221> NAME/KEY: modified_base
<222> LOCATION: 4,6,8,10,12
<223> OTHER INFORMATION: /mod_base = "2'-deoxy-2'-fluoro corresponding
      nucleoside"
<220> FEATURE:
<221> NAME/KEY: modified_base
```

```
<222> LOCATION: 1,3,5,7,9,11
<223> OTHER INFORMATION: /mod_base = "2'-O-methyl corresponding
      nucleoside"
<220> FEATURE:
<221> NAME/KEY: modified_base
<222> LOCATION: 1
<223> OTHER INFORMATION: /mod_base = "Cholesterol-TEG modified
      corresponding nucleotide"

<400> SEQUENCE: 64
uauauaucau ca                                                                12

<210> SEQ ID NO 65
<211> LENGTH: 13
<212> TYPE: RNA
<213> ORGANISM: Artificial Sequence
<220> FEATURE:
<223> OTHER INFORMATION: sense strand of dsRNA
<220> FEATURE:
<221> NAME/KEY: modified_base
<222> LOCATION: 2
<223> OTHER INFORMATION: /mod_base = "2'-hydroxy corresponding
      nucleoside"
<220> FEATURE:
<221> NAME/KEY: modified_base
<222> LOCATION: 4,6,8,10,12
<223> OTHER INFORMATION: /mod_base = "2'-deoxy-2'-fluoro corresponding
      nucleoside"
<220> FEATURE:
<221> NAME/KEY: modified_base
<222> LOCATION: 1,3,5,7,9,11,13
<223> OTHER INFORMATION: /mod_base = "2'-O-methyl corresponding
      nucleoside"
<220> FEATURE:
<221> NAME/KEY: modified_base
<222> LOCATION: 1
<223> OTHER INFORMATION: /mod_base = "Cholesterol-TEG modified
      corresponding nucleotide"

<400> SEQUENCE: 65
uauauaucau cac                                                               13

<210> SEQ ID NO 66
<211> LENGTH: 14
<212> TYPE: RNA
<213> ORGANISM: Artificial Sequence
<220> FEATURE:
<223> OTHER INFORMATION: sense strand of dsRNA
<220> FEATURE:
<221> NAME/KEY: modified_base
<222> LOCATION: 2
<223> OTHER INFORMATION: /mod_base = "2'-hydroxy corresponding
      nucleoside"
<220> FEATURE:
<221> NAME/KEY: modified_base
<222> LOCATION: 4,6,8,10,12,14
<223> OTHER INFORMATION: /mod_base = "2'-deoxy-2'-fluoro corresponding
      nucleoside"
<220> FEATURE:
<221> NAME/KEY: modified_base
<222> LOCATION: 1,3,5,7,9,11,13
<223> OTHER INFORMATION: /mod_base = "2'-O-methyl corresponding
      nucleoside"
<220> FEATURE:
<221> NAME/KEY: modified_base
<222> LOCATION: 1
<223> OTHER INFORMATION: /mod_base = "Cholesterol-TEG modified
      corresponding nucleotide"

<400> SEQUENCE: 66
uauauaucau cacc                                                              14

<210> SEQ ID NO 67
```

-continued

```
<211> LENGTH: 20
<212> TYPE: DNA
<213> ORGANISM: Artificial Sequence
<220> FEATURE:
<223> OTHER INFORMATION: sense strand of dsRNA
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked deoxythymidine"

<400> SEQUENCE: 67
uuacuggaac cuaugaucat                                                   20

<210> SEQ ID NO 68
<211> LENGTH: 13
<212> TYPE: RNA
<213> ORGANISM: Artificial Sequence
<220> FEATURE:
<223> OTHER INFORMATION: sense strand of dsRNA
<220> FEATURE:
<221> NAME/KEY: modified_base
<222> LOCATION: 2
<223> OTHER INFORMATION: /mod_base = "2'-hydroxy corresponding
      nucleoside"
<220> FEATURE:
<221> NAME/KEY: modified_base
<222> LOCATION: 4,6,8,10,12
<223> OTHER INFORMATION: /mod_base = "2'-deoxy-2'-fluoro corresponding
      nucleoside"
<220> FEATURE:
<221> NAME/KEY: modified_base
<222> LOCATION: 1,3,5,7,9,11,13
<223> OTHER INFORMATION: /mod_base = "2'-O-methyl corresponding
      nucleoside"
<220> FEATURE:
<221> NAME/KEY: modified_base
<222> LOCATION: 1
<223> OTHER INFORMATION: /mod_base = "Cholesterol-TEG modified
      corresponding nucleotide"

<400> SEQUENCE: 68
uauuuacugg aac                                                          13

<210> SEQ ID NO 69
<211> LENGTH: 20
<212> TYPE: DNA
<213> ORGANISM: Artificial Sequence
<220> FEATURE:
<223> OTHER INFORMATION: sense strand of dsRNA
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked deoxythymidine"

<400> SEQUENCE: 69
```
ggccgugcau aaggcuguat        20

<210> SEQ ID NO 70
<211> LENGTH: 20
<212> TYPE: DNA
<213> ORGANISM: Artificial Sequence
<220> FEATURE:
<223> OTHER INFORMATION: sense strand of dsRNA
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked deoxythymidine"

<400> SEQUENCE: 70
ggcugugcug accaucgaat        20

<210> SEQ ID NO 71
<211> LENGTH: 12
<212> TYPE: RNA
<213> ORGANISM: Artificial Sequence
<220> FEATURE:
<223> OTHER INFORMATION: sense strand of dsRNA
<220> FEATURE:
<221> NAME/KEY: modified_base
<222> LOCATION: 2
<223> OTHER INFORMATION: /mod_base = "2'-hydroxy corresponding
      nucleoside"
<220> FEATURE:
<221> NAME/KEY: modified_base
<222> LOCATION: 4,6,8,10,12
<223> OTHER INFORMATION: /mod_base = "2'-deoxy-2'-fluoro corresponding
      nucleoside"
<220> FEATURE:
<221> NAME/KEY: modified_base
<222> LOCATION: 1,3,5,7,9,11
<223> OTHER INFORMATION: /mod_base = "2'-O-methyl corresponding
      nucleoside"
<220> FEATURE:
<221> NAME/KEY: modified_base
<222> LOCATION: 1
<223> OTHER INFORMATION: /mod_base = "Cholesterol-TEG modified
      corresponding nucleotide"

<400> SEQUENCE: 71
uauggcugug cu        12

<210> SEQ ID NO 72
<211> LENGTH: 13
<212> TYPE: RNA
<213> ORGANISM: Artificial Sequence
<220> FEATURE:
<223> OTHER INFORMATION: sense strand of dsRNA
<220> FEATURE:
<221> NAME/KEY: modified_base
<222> LOCATION: 2
<223> OTHER INFORMATION: /mod_base = "2'-hydroxy corresponding
      nucleoside"
<220> FEATURE:
<221> NAME/KEY: modified_base
<222> LOCATION: 4,6,8,10,12
<223> OTHER INFORMATION: /mod_base = "2'-deoxy-2'-fluoro corresponding
      nucleoside"
<220> FEATURE:

```
<221> NAME/KEY: modified_base
<222> LOCATION: 1,3,5,7,9,11,13
<223> OTHER INFORMATION: /mod_base = "2'-O-methyl corresponding
      nucleoside"
<220> FEATURE:
<221> NAME/KEY: modified_base
<222> LOCATION: 1
<223> OTHER INFORMATION: /mod_base = "Cholesterol-TEG modified
      corresponding nucleotide"

<400> SEQUENCE: 72
uauggcugug cug                                                      13

<210> SEQ ID NO 73
<211> LENGTH: 14
<212> TYPE: RNA
<213> ORGANISM: Artificial Sequence
<220> FEATURE:
<223> OTHER INFORMATION: sense strand of dsRNA
<220> FEATURE:
<221> NAME/KEY: modified_base
<222> LOCATION: 2
<223> OTHER INFORMATION: /mod_base = "2'-hydroxy corresponding
      nucleoside"
<220> FEATURE:
<221> NAME/KEY: modified_base
<222> LOCATION: 4,6,8,10,12,14
<223> OTHER INFORMATION: /mod_base = "2'-deoxy-2'-fluoro corresponding
      nucleoside"
<220> FEATURE:
<221> NAME/KEY: modified_base
<222> LOCATION: 1,3,5,7,9,11,13
<223> OTHER INFORMATION: /mod_base = "2'-O-methyl corresponding
      nucleoside"
<220> FEATURE:
<221> NAME/KEY: modified_base
<222> LOCATION: 1
<223> OTHER INFORMATION: /mod_base = "Cholesterol-TEG modified
      corresponding nucleotide"

<400> SEQUENCE: 73
uauggcugug cuga                                                     14

<210> SEQ ID NO 74
<211> LENGTH: 11
<212> TYPE: RNA
<213> ORGANISM: Artificial Sequence
<220> FEATURE:
<223> OTHER INFORMATION: sense strand of dsRNA
<220> FEATURE:
<221> NAME/KEY: modified_base
<222> LOCATION: 2
<223> OTHER INFORMATION: /mod_base = "2'-hydroxy corresponding
      nucleoside"
<220> FEATURE:
<221> NAME/KEY: modified_base
<222> LOCATION: 4,6,8,10
<223> OTHER INFORMATION: /mod_base = "2'-deoxy-2'-fluoro corresponding
      nucleoside"
<220> FEATURE:
<221> NAME/KEY: modified_base
<222> LOCATION: 1,3,5,7,9,11
<223> OTHER INFORMATION: /mod_base = "2'-O-methyl corresponding
      nucleoside"
<220> FEATURE:
<221> NAME/KEY: modified_base
<222> LOCATION: 1
<223> OTHER INFORMATION: /mod_base = "Cholesterol-TEG modified
      corresponding nucleotide"

<400> SEQUENCE: 74
uauggcugug c                                                        11
```

-continued

```
<210> SEQ ID NO 75
<211> LENGTH: 20
<212> TYPE: DNA
<213> ORGANISM: Artificial Sequence
<220> FEATURE:
<223> OTHER INFORMATION: sense strand of dsRNA
<220> FEATURE:
<221> NAME/KEY: modified_base
<222> LOCATION: 1,3,5,7,9,11,13,15,17,19
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8,10,12,14,16,18
<223> OTHER INFORMATION: /mod_base = "2'-O-methyl corresponding
      nucleoside"
<220> FEATURE:
<221> NAME/KEY: modified_base
<222> LOCATION: 20
<223> OTHER INFORMATION: /mod_base = "3'-3'-linked deoxythymidine"

<400> SEQUENCE: 75
aguucaacaa acccuuugat                                                   20

<210> SEQ ID NO 76
<211> LENGTH: 14
<212> TYPE: RNA
<213> ORGANISM: Artificial Sequence
<220> FEATURE:
<223> OTHER INFORMATION: sense strand of dsRNA
<220> FEATURE:
<221> NAME/KEY: modified_base
<222> LOCATION: 2
<223> OTHER INFORMATION: /mod_base = "2'-hydroxy corresponding
      nucleoside"
<220> FEATURE:
<221> NAME/KEY: modified_base
<222> LOCATION: 4,6,8,10,12,14
<223> OTHER INFORMATION: /mod_base = "2'-deoxy-2'-fluoro corresponding
      nucleoside"
<220> FEATURE:
<221> NAME/KEY: modified_base
<222> LOCATION: 1,3,5,7,9,11,13
<223> OTHER INFORMATION: /mod_base = "2'-O-methyl corresponding
      nucleoside"
<220> FEATURE:
<221> NAME/KEY: modified_base
<222> LOCATION: 1
<223> OTHER INFORMATION: /mod_base = "Cholesterol-TEG modified
      corresponding nucleotide"

<400> SEQUENCE: 76
uauaguucaa caaa                                                         14

<210> SEQ ID NO 77
<211> LENGTH: 23
<212> TYPE: DNA
<213> ORGANISM: Artificial Sequence
<220> FEATURE:
<223> OTHER INFORMATION: sense strand of dsRNA
<220> FEATURE:
<221> NAME/KEY: modified_base
<222> LOCATION: 2
<223> OTHER INFORMATION: /mod_base = "2'-hydroxy corresponding
      nucleoside"
<220> FEATURE:
<221> NAME/KEY: modified_base
<222> LOCATION: 4,6,8,10,12,14,16,18,20,22
<223> OTHER INFORMATION: /mod_base = "2'-deoxy-2'-fluoro corresponding
      nucleoside"
<220> FEATURE:
<221> NAME/KEY: modified_base
<222> LOCATION: 1,3,5,7,9,11,13,15,17,19,21
<223> OTHER INFORMATION: /mod_base = "2'-O-methyl corresponding
      nucleoside"
```

```
<220> FEATURE:
<221> NAME/KEY: modified_base
<222> LOCATION: 23
<223> OTHER INFORMATION: /mod_base = "3'-3'-linked deoxythymidine"
<220> FEATURE:
<221> NAME/KEY: modified_base
<222> LOCATION: 1
<223> OTHER INFORMATION: /mod_base = "Cholesterol-TEG modified
      corresponding nucleotide"

<400> SEQUENCE: 77
uauaguucaa caaacccuuu gat                                            23

<210> SEQ ID NO 78
<211> LENGTH: 23
<212> TYPE: DNA
<213> ORGANISM: Artificial Sequence
<220> FEATURE:
<223> OTHER INFORMATION: sense strand of dsRNA
<220> FEATURE:
<221> NAME/KEY: modified_base
<222> LOCATION: 2
<223> OTHER INFORMATION: /mod_base = "2'-hydroxy corresponding
      nucleoside"
<220> FEATURE:
<221> NAME/KEY: modified_base
<222> LOCATION: 4,6,8,10,12,14,16,18,20,22
<223> OTHER INFORMATION: /mod_base = "2'-deoxy-2'-fluoro corresponding
      nucleoside"
<220> FEATURE:
<221> NAME/KEY: modified_base
<222> LOCATION: 1,3,5,7,9,11,13,15,17,19,21
<223> OTHER INFORMATION: /mod_base = "2'-O-methyl corresponding
      nucleoside"
<220> FEATURE:
<221> NAME/KEY: modified_base
<222> LOCATION: 23
<223> OTHER INFORMATION: /mod_base = "3'-3'-linked deoxythymidine"
<220> FEATURE:
<221> NAME/KEY: modified_base
<222> LOCATION: 1
<223> OTHER INFORMATION: /mod_base = "Cholesterol-TEG modified
      corresponding nucleotide"

<400> SEQUENCE: 78
uaucuuacgc ugaguacuuc gat                                            23

<210> SEQ ID NO 79
<211> LENGTH: 23
<212> TYPE: DNA
<213> ORGANISM: Artificial Sequence
<220> FEATURE:
<223> OTHER INFORMATION: sense strand of dsRNA
<220> FEATURE:
<221> NAME/KEY: modified_base
<222> LOCATION: 2
<223> OTHER INFORMATION: /mod_base = "2'-hydroxy corresponding
      nucleoside"
<220> FEATURE:
<221> NAME/KEY: modified_base
<222> LOCATION: 4,6,8,10,12,14,16,18,20,22
<223> OTHER INFORMATION: /mod_base = "2'-deoxy-2'-fluoro corresponding
      nucleoside"
<220> FEATURE:
<221> NAME/KEY: modified_base
<222> LOCATION: 1,3,5,7,9,11,13,15,17,19,21
<223> OTHER INFORMATION: /mod_base = "2'-O-methyl corresponding
      nucleoside"
<220> FEATURE:
<221> NAME/KEY: modified_base
<222> LOCATION: 23
<223> OTHER INFORMATION: /mod_base = "3'-3'-linked deoxythymidine"
<220> FEATURE:
<221> NAME/KEY: modified_base
<222> LOCATION: 1
```

<223> OTHER INFORMATION: /mod_base = "Cholesterol modified
      corresponding nucleotide"

<400> SEQUENCE: 79
uaucuuacgc ugaguacuuc gat                                           23

<210> SEQ ID NO 80
<211> LENGTH: 23
<212> TYPE: DNA
<213> ORGANISM: Artificial Sequence
<220> FEATURE:
<223> OTHER INFORMATION: sense strand of dsRNA
<220> FEATURE:
<221> NAME/KEY: modified_base
<222> LOCATION: 2
<223> OTHER INFORMATION: /mod_base = "2'-hydroxy corresponding
      nucleoside"
<220> FEATURE:
<221> NAME/KEY: modified_base
<222> LOCATION: 4,6,8,10,12,14,16,18,20,22
<223> OTHER INFORMATION: /mod_base = "2'-deoxy-2'-fluoro corresponding
      nucleoside"
<220> FEATURE:
<221> NAME/KEY: modified_base
<222> LOCATION: 1,3,5,7,9,11,13,15,17,19,21
<223> OTHER INFORMATION: /mod_base = "2'-O-methyl corresponding
      nucleoside"
<220> FEATURE:
<221> NAME/KEY: modified_base
<222> LOCATION: 23
<223> OTHER INFORMATION: /mod_base = "3'-3'-linked deoxythymidine"
<220> FEATURE:
<221> NAME/KEY: modified_base
<222> LOCATION: 1
<223> OTHER INFORMATION: /mod_base = "Cholesterol-C6 modified
      corresponding nucleotide"

<400> SEQUENCE: 80
uaugcaaagg cgugccaacu cat                                           23

<210> SEQ ID NO 81
<211> LENGTH: 11
<212> TYPE: DNA
<213> ORGANISM: Artificial Sequence
<220> FEATURE:
<223> OTHER INFORMATION: sense strand of dsRNA
<220> FEATURE:
<221> NAME/KEY: modified_base
<222> LOCATION: 2,4,6,8,10
<223> OTHER INFORMATION: /mod_base = "2'-deoxy-2'-fluoro corresponding
      nucleoside"
<220> FEATURE:
<221> NAME/KEY: modified_base
<222> LOCATION: 1,3,5,7,9
<223> OTHER INFORMATION: /mod_base = "2'-O-methyl corresponding
      nucleoside"
<220> FEATURE:
<221> NAME/KEY: modified_base
<222> LOCATION: 11
<223> OTHER INFORMATION: /mod_base = "3'-3'-linked deoxythymidine"

<400> SEQUENCE: 81
ccaaguucca t                                                        11

<210> SEQ ID NO 82
<211> LENGTH: 10
<212> TYPE: DNA
<213> ORGANISM: Artificial Sequence
<220> FEATURE:
<223> OTHER INFORMATION: sense strand of dsRNA
<220> FEATURE:
<221> NAME/KEY: modified_base
<222> LOCATION: 1,3,5,7,9

```
            <223> OTHER INFORMATION: /mod_base = "2'-deoxy-2'-fluoro corresponding
                  nucleoside"
            <220> FEATURE:
            <221> NAME/KEY: modified_base
            <222> LOCATION: 2,4,6,8
            <223> OTHER INFORMATION: /mod_base = "2'-O-methyl corresponding
                  nucleoside"
            <220> FEATURE:
            <221> NAME/KEY: modified_base
            <222> LOCATION: 10
            <223> OTHER INFORMATION: /mod_base = "3'-3'-linked deoxythymidine"

<400> SEQUENCE: 82
caaguuccat                                                                 10

<210> SEQ ID NO 83
            <211> LENGTH: 9
            <212> TYPE: DNA
            <213> ORGANISM: Artificial Sequence
            <220> FEATURE:
            <223> OTHER INFORMATION: sense strand of dsRNA
            <220> FEATURE:
            <221> NAME/KEY: modified_base
            <222> LOCATION: 2,4,6,8
            <223> OTHER INFORMATION: /mod_base = "2'-deoxy-2'-fluoro corresponding
                  nucleoside"
            <220> FEATURE:
            <221> NAME/KEY: modified_base
            <222> LOCATION: 1,3,5,7
            <223> OTHER INFORMATION: /mod_base = "2'-O-methyl corresponding
                  nucleoside"
            <220> FEATURE:
            <221> NAME/KEY: modified_base
            <222> LOCATION: 9
            <223> OTHER INFORMATION: /mod_base = "3'-3'-linked deoxythymidine"

<400> SEQUENCE: 83 aaguuccat                                                                   9

<210> SEQ ID NO 84
            <211> LENGTH: 10
            <212> TYPE: DNA
            <213> ORGANISM: Artificial Sequence
            <220> FEATURE:
            <223> OTHER INFORMATION: sense strand of dsRNA
            <220> FEATURE:
            <221> NAME/KEY: modified_base
            <222> LOCATION: 1,3,5,7,9
            <223> OTHER INFORMATION: /mod_base = "2'-deoxy-2'-fluoro corresponding
                  nucleoside"
            <220> FEATURE:
            <221> NAME/KEY: modified_base
            <222> LOCATION: 2,4,6,8
            <223> OTHER INFORMATION: /mod_base = "2'-O-methyl corresponding
                  nucleoside"
            <220> FEATURE:
            <221> NAME/KEY: modified_base
            <222> LOCATION: 10
            <223> OTHER INFORMATION: /mod_base = "3'-3'-linked deoxythymidine"

<400> SEQUENCE: 84
cuaugaucat                                                                 10

<210> SEQ ID NO 85
            <211> LENGTH: 11
            <212> TYPE: DNA
            <213> ORGANISM: Artificial Sequence
            <220> FEATURE:
            <223> OTHER INFORMATION: sense strand of dsRNA
            <220> FEATURE:
            <221> NAME/KEY: modified_base
            <222> LOCATION: 2,4,6,8,10
            <223> OTHER INFORMATION: /mod_base = "2'-deoxy-2'-fluoro corresponding
```

-continued

```
      nucleoside"
<220> FEATURE:
<221> NAME/KEY: modified_base
<222> LOCATION: 1,3,5,7,9
<223> OTHER INFORMATION: /mod_base = "2'-O-methyl corresponding
      nucleoside"
<220> FEATURE:
<221> NAME/KEY: modified_base
<222> LOCATION: 11
<223> OTHER INFORMATION: /mod_base = "3'-3'-linked deoxythymidine"

<400> SEQUENCE: 85
gaccaucgaa t                                                               11

<210> SEQ ID NO 86
<211> LENGTH: 10
<212> TYPE: DNA
<213> ORGANISM: Artificial Sequence
<220> FEATURE:
<223> OTHER INFORMATION: sense strand of dsRNA
<220> FEATURE:
<221> NAME/KEY: modified_base
<222> LOCATION: 1,3,5,7,9
<223> OTHER INFORMATION: /mod_base = "2'-deoxy-2'-fluoro corresponding
      nucleoside"
<220> FEATURE:
<221> NAME/KEY: modified_base
<222> LOCATION: 2,4,6,8
<223> OTHER INFORMATION: /mod_base = "2'-O-methyl corresponding
      nucleoside"
<220> FEATURE:
<221> NAME/KEY: modified_base
<222> LOCATION: 10
<223> OTHER INFORMATION: /mod_base = "3'-3'-linked deoxythymidine"

<400> SEQUENCE: 86
accaucgaat                                                                 10

<210> SEQ ID NO 87
<211> LENGTH: 9
<212> TYPE: DNA
<213> ORGANISM: Artificial Sequence
<220> FEATURE:
<223> OTHER INFORMATION: sense strand of dsRNA
<220> FEATURE:
<221> NAME/KEY: modified_base
<222> LOCATION: 2,4,6,8
<223> OTHER INFORMATION: /mod_base = "2'-deoxy-2'-fluoro corresponding
      nucleoside"
<220> FEATURE:
<221> NAME/KEY: modified_base
<222> LOCATION: 1,3,5,7
<223> OTHER INFORMATION: /mod_base = "2'-O-methyl corresponding
      nucleoside"
<220> FEATURE:
<221> NAME/KEY: modified_base
<222> LOCATION: 9
<223> OTHER INFORMATION: /mod_base = "3'-3'-linked deoxythymidine"

<400> SEQUENCE: 87 ccaucgaat                                                                  9

<210> SEQ ID NO 88
<211> LENGTH: 12
<212> TYPE: DNA
<213> ORGANISM: Artificial Sequence
<220> FEATURE:
<223> OTHER INFORMATION: sense strand of dsRNA
<220> FEATURE:
<221> NAME/KEY: modified_base
<222> LOCATION: 1,3,5,7,9,11
<223> OTHER INFORMATION: /mod_base = "2'-deoxy-2'-fluoro corresponding
      nucleoside"
```

<220> FEATURE:
<221> NAME/KEY: modified_base
<222> LOCATION: 2,4,6,8,10
<223> OTHER INFORMATION: /mod_base = "2'-O-methyl corresponding nucleoside"
<220> FEATURE:
<221> NAME/KEY: modified_base
<222> LOCATION: 12
<223> OTHER INFORMATION: /mod_base = "3'-3'-linked deoxythymidine"

<400> SEQUENCE: 88
ugaccaucga at                                                           12

<210> SEQ ID NO 89
<211> LENGTH: 9
<212> TYPE: DNA
<213> ORGANISM: Artificial Sequence
<220> FEATURE:
<223> OTHER INFORMATION: sense strand of dsRNA
<220> FEATURE:
<221> NAME/KEY: modified_base
<222> LOCATION: 2,4,6,8
<223> OTHER INFORMATION: /mod_base = "2'-deoxy-2'-fluoro corresponding nucleoside"
<220> FEATURE:
<221> NAME/KEY: modified_base
<222> LOCATION: 1,3,5,7
<223> OTHER INFORMATION: /mod_base = "2'-O-methyl corresponding nucleoside"
<220> FEATURE:
<221> NAME/KEY: modified_base
<222> LOCATION: 9
<223> OTHER INFORMATION: /mod_base = "3'-3'-linked deoxythymidine"

<400> SEQUENCE: 89 cccuuugat                                                                9

<210> SEQ ID NO 90
<211> LENGTH: 26
<212> TYPE: PRT
<213> ORGANISM: Apis florea

<400> SEQUENCE: 90

Gly Ile Gly Ala Ile Leu Lys Val Leu Ala Thr Gly Leu Pro Thr Leu
1               5                   10                  15

Ile Ser Trp Ile Lys Asn Lys Arg Lys Gln
            20                  25

<210> SEQ ID NO 91
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 91

Ala Ile Gly Ala Ile Leu Lys Val Leu Ala Thr Gly Leu Pro Thr Leu
1               5                   10                  15

Ile Ser Trp Ile Lys Asn Lys Arg Lys Gln
            20                  25

<210> SEQ ID NO 92
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 92

Cys Ile Gly Ala Ile Leu Lys Val Leu Ala Thr Gly Leu Pro Thr Leu
1               5                   10                  15

Ile Ser Trp Ile Lys Asn Lys Arg Lys Gln
            20                  25

<210> SEQ ID NO 93
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 93

Phe Ile Gly Ala Ile Leu Lys Val Leu Ala Thr Gly Leu Pro Thr Leu
1               5                   10                  15

Ile Ser Trp Ile Lys Asn Lys Arg Lys Gln
            20                  25

<210> SEQ ID NO 94
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 94

His Ile Gly Ala Ile Leu Lys Val Leu Ala Thr Gly Leu Pro Thr Leu
1               5                   10                  15

Ile Ser Trp Ile Lys Asn Lys Arg Lys Gln
            20                  25

<210> SEQ ID NO 95
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 95

Ile Ile Gly Ala Ile Leu Lys Val Leu Ala Thr Gly Leu Pro Thr Leu
1               5                   10                  15

Ile Ser Trp Ile Lys Asn Lys Arg Lys Gln
            20                  25

<210> SEQ ID NO 96
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 96

Leu Ile Gly Ala Ile Leu Lys Val Leu Ala Thr Gly Leu Pro Thr Leu
1               5                   10                  15

Ile Ser Trp Ile Lys Asn Lys Arg Lys Gln
            20                  25

<210> SEQ ID NO 97
<211> LENGTH: 26
<212> TYPE: PRT
<213> ORGANISM: Artificial Sequence
<220> FEATURE:
<223> OTHER INFORMATION: Melittin-like peptide
<220> FEATURE:

```
<221> NAME/KEY: misc_feature
<222> LOCATION: (1)..(1)
<223> OTHER INFORMATION: Xaa is Nle

<400> SEQUENCE: 97

Xaa Ile Gly Ala Ile Leu Lys Val Leu Ala Thr Gly Leu Pro Thr Leu
 1               5                  10                  15

Ile Ser Trp Ile Lys Asn Lys Arg Lys Gln
            20                  25

<210> SEQ ID NO 98
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 98

Val Ile Gly Ala Ile Leu Lys Val Leu Ala Thr Gly Leu Pro Thr Leu
 1               5                  10                  15

Ile Ser Trp Ile Lys Asn Lys Arg Lys Gln
            20                  25

<210> SEQ ID NO 99
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 99

Trp Ile Gly Ala Ile Leu Lys Val Leu Ala Thr Gly Leu Pro Thr Leu
 1               5                  10                  15

Ile Ser Trp Ile Lys Asn Lys Arg Lys Gln
            20                  25

<210> SEQ ID NO 100
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 100

Tyr Ile Gly Ala Ile Leu Lys Val Leu Ala Thr Gly Leu Pro Thr Leu
 1               5                  10                  15

Ile Ser Trp Ile Lys Asn Lys Arg Lys Gln
            20                  25

<210> SEQ ID NO 101
<211> LENGTH: 26
<212> TYPE: PRT
<213> ORGANISM: Artificial Sequence
<220> FEATURE:
<223> OTHER INFORMATION: D-form Apis florea melittin sequence

<400> SEQUENCE: 101

Gly Ile Gly Ala Ile Leu Lys Val Leu Ala Cys Gly Leu Pro Thr Leu
 1               5                  10                  15

Ile Ser Trp Ile Lys Asn Lys Arg Lys Gln
            20                  25

<210> SEQ ID NO 102
<211> LENGTH: 26
```

```
<212> TYPE: PRT
<213> ORGANISM: Artificial Sequence
<220> FEATURE:
<223> OTHER INFORMATION: Melittin-like peptide

<400> SEQUENCE: 102

Gly Ile Gly Ala Ile Leu Lys Val Leu Ala Thr Leu Leu Pro Thr Leu
1               5                   10                  15

Ile Ser Trp Ile Lys Asn Lys Arg Lys Gln
            20                  25

<210> SEQ ID NO 103
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 103

Gly Ile Gly Ala Ile Leu Lys Val Leu Ala Thr Trp Leu Pro Thr Leu
1               5                   10                  15

Ile Ser Trp Ile Lys Asn Lys Arg Lys Gln
            20                  25

<210> SEQ ID NO 104
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 104

Gly Ile Gly Ala Ile Leu Lys Val Leu Ala Thr Gly Leu Pro Thr Leu
1               5                   10                  15

Ile Ser Trp Ile Lys Thr Lys Arg Lys Gln
            20                  25

<210> SEQ ID NO 105
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 105

Tyr Ile Gly Ala Ile Leu Asn Val Leu Ala Thr Gly Leu Pro Thr Leu
1               5                   10                  15

Ile Ser Trp Ile Lys Asn Lys Arg Lys Gln
            20                  25

<210> SEQ ID NO 106
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 106

Tyr Ile Gly Ala Ile Leu Ala Val Leu Ala Thr Gly Leu Pro Thr Leu
1               5                   10                  15

Ile Ser Trp Ile Lys Asn Lys Arg Lys Gln
            20                  25

<210> SEQ ID NO 107
```

-continued

```
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 107

Leu Ile Gly Ala Ile Leu Ser Val Leu Ala Thr Gly Leu Pro Thr Leu
1               5                   10                  15

Ile Ser Trp Ile Lys Asn Lys Arg Lys Gln
            20                  25

<210> SEQ ID NO 108
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 108

Leu Ile Gly Ala Ile Leu Arg Val Leu Ala Thr Gly Leu Pro Thr Leu
1               5                   10                  15

Ile Ser Trp Ile Lys Asn Lys Arg Lys Gln
            20                  25

<210> SEQ ID NO 109
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 109

Leu Ile Gly Ala Ile Leu His Val Leu Ala Thr Gly Leu Pro Thr Leu
1               5                   10                  15

Ile Ser Trp Ile Lys Asn Lys Arg Lys Gln
            20                  25

<210> SEQ ID NO 110
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 110

Leu Ile Gly Ala Ile Leu Lys Val Leu Ala Cys Gly Leu Pro Thr Leu
1               5                   10                  15

Ile Ser Trp Ile Lys Asn Lys Arg Lys Gln
            20                  25

<210> SEQ ID NO 111
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 111

Leu Ile Gly Ala Ile Leu Lys Val Leu Ala Thr Leu Leu Pro Thr Leu
1               5                   10                  15

Ile Ser Trp Ile Lys Asn Lys Arg Lys Gln
            20                  25
```

```
<210> SEQ ID NO 112
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 112

Tyr Ile Gly Ala Ile Leu Lys Val Leu Ala Thr Gly Leu Leu Thr Leu
1               5                   10                  15

Ile Ser Trp Ile Lys Asn Lys Arg Lys Gln
            20                  25

<210> SEQ ID NO 113
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 113

Leu Ile Gly Ala Ile Leu Lys Val Leu Ala Thr Gly Leu Pro Cys Leu
1               5                   10                  15

Ile Ser Trp Ile Lys Asn Lys Arg Lys Gln
            20                  25

<210> SEQ ID NO 114
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 114

Leu Ile Gly Ala Ile Leu Lys Val Leu Ala Thr Gly Leu Pro Thr Leu
1               5                   10                  15

Ile Cys Trp Ile Lys Asn Lys Arg Lys Gln
            20                  25

<210> SEQ ID NO 115
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 115

Tyr Ile Gly Ala Ile Leu Lys Val Leu Ala Thr Gly Leu Pro Thr Leu
1               5                   10                  15

Ile Ser Ala Ile Lys Asn Lys Arg Lys Gln
            20                  25

<210> SEQ ID NO 116
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 116

Gly Ile Gly Ala Ile Leu Lys Val Leu Ala Cys Gly Leu Pro Thr Leu
1               5                   10                  15

Ile Ser Trp Leu Lys Asn Lys Arg Lys Gln
            20                  25
```

<210> SEQ ID NO 117
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 117

Tyr Ile Gly Ala Ile Leu Lys Val Leu Ala Thr Gly Leu Pro Thr Leu
1               5                   10                  15
Ile Ser Trp Ile Ala Asn Lys Arg Lys Gln
            20                  25

<210> SEQ ID NO 118
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 118

Tyr Ile Gly Ala Ile Leu Lys Val Leu Ala Thr Gly Leu Pro Thr Leu
1               5                   10                  15
Ile Ser Trp Ile Lys Asn Ala Arg Lys Gln
            20                  25

<210> SEQ ID NO 119
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 119

Leu Ile Gly Ala Ile Leu Lys Val Leu Ala Thr Gly Leu Pro Thr Leu
1               5                   10                  15
Ile Ser Trp Ile Lys Asn Lys Ala Lys Gln
            20                  25

<210> SEQ ID NO 120
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 120

Tyr Ile Gly Ala Ile Leu Lys Val Leu Ala Thr Gly Leu Pro Thr Leu
1               5                   10                  15
Ile Ser Trp Ile Lys Asn Lys Arg Ala Gln
            20                  25

<210> SEQ ID NO 121
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 121

Tyr Ile Gly Ala Ile Leu Lys Val Leu Ala Thr Gly Leu Pro Thr Leu
1               5                   10                  15
Ile Ser Trp Ile Lys Asn Lys Arg Lys Cys
            20                  25

<210> SEQ ID NO 122
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 122

Leu Leu Gly Ala Ile Leu Lys Val Leu Ala Cys Gly Leu Pro Thr Leu
1               5                   10                  15

Ile Ser Trp Ile Lys Asn Lys Arg Lys Gln
            20                  25

<210> SEQ ID NO 123
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 123

Leu Ile Gly Ala Leu Leu Lys Val Leu Ala Cys Gly Leu Pro Thr Leu
1               5                   10                  15

Ile Ser Trp Ile Lys Asn Lys Arg Lys Gln
            20                  25

<210> SEQ ID NO 124
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 124

Tyr Ile Gly Ala Ile Leu Ala Val Leu Ala Thr Gly Leu Pro Thr Leu
1               5                   10                  15

Ile Ser Trp Ile Ala Asn Lys Arg Lys Gln
            20                  25

<210> SEQ ID NO 125
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 125

Tyr Ile Gly Ala Ile Leu Ala Val Leu Ala Thr Gly Leu Pro Thr Leu
1               5                   10                  15

Ile Ser Trp Ile Lys Asn Ala Arg Lys Gln
            20                  25

<210> SEQ ID NO 126
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 126

Leu Ile Gly Ala Ile Leu Lys Val Leu Ala Cys Gly Leu Pro Thr Leu
1               5                   10                  15

Leu Ser Trp Ile Lys Asn Lys Arg Lys Gln

```
                        20                  25

<210> SEQ ID NO 127
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 127

Leu Ile Gly Ala Ile Leu Lys Val Leu Ala Cys Gly Leu Pro Thr Leu
1               5                   10                  15

Ile Cys Trp Ile Lys Asn Lys Arg Lys Gln
            20                  25

<210> SEQ ID NO 128
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 128

Gly Ile Gly Ala Ile Leu Lys Val Leu Ala Cys Gly Leu Pro Gly Leu
1               5                   10                  15

Ile Gly Trp Ile Lys Asn Lys Arg Lys Gln
            20                  25

<210> SEQ ID NO 129
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 129

Gly Ile Gly Ala Ile Leu Lys Val Leu Ala Cys Gly Leu Pro Ala Leu
1               5                   10                  15

Ile Ala Trp Ile Lys Asn Lys Arg Lys Gln
            20                  25

<210> SEQ ID NO 130
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 130

Tyr Ile Gly Ala Ile Leu Ala Val Leu Ala Thr Gly Leu Pro Thr Leu
1               5                   10                  15

Ile Ser Trp Ile Ala Asn Ala Arg Lys Gln
            20                  25

<210> SEQ ID NO 131
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 131

Tyr Ile Ala Ala Ile Leu Lys Val Leu Ala Ala Ala Leu Ala Thr Leu
1               5                   10                  15
```

Ile Ser Trp Ile Lys Asn Lys Arg Lys Gln
            20                  25

<210> SEQ ID NO 132
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 132

Leu Leu Gly Ala Leu Leu Lys Val Leu Ala Thr Gly Leu Pro Thr Leu
1               5                   10                  15

Leu Ser Trp Leu Lys Asn Lys Arg Lys Gln
            20                  25

<210> SEQ ID NO 133
<211> LENGTH: 26
<212> TYPE: PRT
<213> ORGANISM: Artificial Sequence
<220> FEATURE:
<223> OTHER INFORMATION: Melittin-like peptide
<220> FEATURE:
<221> NAME/KEY: misc_feature
<222> LOCATION: 2, 5, 17, 20
<223> OTHER INFORMATION: Xaa is Nle

<400> SEQUENCE: 133

Leu Xaa Gly Ala Xaa Leu Lys Val Leu Ala Thr Gly Leu Pro Thr Leu
1               5                   10                  15

Xaa Ser Trp Xaa Lys Asn Lys Arg Lys Gln
            20                  25

<210> SEQ ID NO 134
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 134

Leu Val Gly Ala Val Leu Lys Val Leu Ala Thr Gly Leu Pro Thr Leu
1               5                   10                  15

Val Ser Trp Val Lys Asn Lys Arg Lys Gln
            20                  25

<210> SEQ ID NO 135
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 135

Gly Leu Gly Ala Leu Leu Lys Val Leu Ala Cys Gly Leu Pro Thr Leu
1               5                   10                  15

Leu Ser Trp Leu Lys Asn Lys Arg Lys Gln
            20                  25

<210> SEQ ID NO 136
<211> LENGTH: 26
<212> TYPE: PRT
<213> ORGANISM: Artificial Sequence
<220> FEATURE:
<223> OTHER INFORMATION: Melittin-like peptide
<220> FEATURE:

<221> NAME/KEY: misc_feature
<222> LOCATION: 2, 5, 17, 20
<223> OTHER INFORMATION: Xaa is Nle

<400> SEQUENCE: 136

Gly Xaa Gly Ala Xaa Leu Lys Val Leu Ala Cys Gly Leu Pro Thr Leu
1               5                   10                  15

Xaa Ser Trp Xaa Lys Asn Lys Arg Lys Gln
            20                  25

<210> SEQ ID NO 137
<211> LENGTH: 31
<212> TYPE: PRT
<213> ORGANISM: Artificial Sequence
<220> FEATURE:
<223> OTHER INFORMATION: Melittin-like peptide

<400> SEQUENCE: 137

Cys Glu Asp Asp Leu Leu Leu Gly Ala Ile Leu Lys Val Leu Ala Thr
1               5                   10                  15

Gly Leu Pro Thr Leu Ile Ser Trp Ile Lys Asn Lys Arg Lys Gln
            20                  25                  30

<210> SEQ ID NO 138
<211> LENGTH: 31
<212> TYPE: PRT
<213> ORGANISM: Artificial Sequence
<220> FEATURE:
<223> OTHER INFORMATION: Melittin-like peptide

<400> SEQUENCE: 138

Cys Leu Val Val Leu Ile Val Val Ala Ile Leu Lys Val Leu Ala Thr
1               5                   10                  15

Gly Leu Pro Thr Leu Ile Ser Trp Ile Lys Asn Lys Arg Lys Gln
            20                  25                  30

<210> SEQ ID NO 139
<211> LENGTH: 26
<212> TYPE: PRT
<213> ORGANISM: Apis mellifera

<400> SEQUENCE: 139

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 140
<211> LENGTH: 27
<212> TYPE: PRT
<213> ORGANISM: Artificial Sequence
<220> FEATURE:
<223> OTHER INFORMATION: Melittin-like peptide

<400> SEQUENCE: 140

Cys Leu Ile Gly Ala Ile Leu Lys Val Leu Ala Thr Gly Leu Pro Thr
1               5                   10                  15

Leu Ile Ser Trp Ile Lys Asn Lys Arg Lys Gln
            20                  25

<210> SEQ ID NO 141
<211> LENGTH: 27
<212> TYPE: PRT
<213> ORGANISM: Artificial Sequence

```
<220> FEATURE:
<223> OTHER INFORMATION: Melittin-like peptide
<220> FEATURE:
<221> NAME/KEY: misc_feature
<222> LOCATION: (2)..(2)
<223> OTHER INFORMATION: Xaa is Nle

<400> SEQUENCE: 141

Cys Xaa Ile Gly Ala Ile Leu Lys Val Leu Ala Thr Gly Leu Pro Thr
1               5                   10                  15

Leu Ile Ser Trp Ile Lys Asn Lys Arg Lys Gln
            20                  25

<210> SEQ ID NO 142
<211> LENGTH: 27
<212> TYPE: PRT
<213> ORGANISM: Artificial Sequence
<220> FEATURE:
<223> OTHER INFORMATION: Melittin-like peptide

<400> SEQUENCE: 142

Gly Leu Ile Gly Ala Ile Leu Lys Val Leu Ala Thr Gly Leu Pro Thr
1               5                   10                  15

Leu Ile Ser Trp Ile Lys Asn Lys Arg Lys Gln
            20                  25

<210> SEQ ID NO 143
<211> LENGTH: 27
<212> TYPE: PRT
<213> ORGANISM: Artificial Sequence
<220> FEATURE:
<223> OTHER INFORMATION: Melittin-like peptide

<400> SEQUENCE: 143

Leu Leu Ile Gly Ala Ile Leu Lys Val Leu Ala Thr Gly Leu Pro Thr
1               5                   10                  15

Leu Ile Ser Trp Ile Lys Asn Lys Arg Lys Gln
            20                  25

<210> SEQ ID NO 144
<211> LENGTH: 29
<212> TYPE: PRT
<213> ORGANISM: Artificial Sequence
<220> FEATURE:
<223> OTHER INFORMATION: Melittin-like peptide

<400> SEQUENCE: 144

Lys Leu Lys Leu Ile Gly Ala Ile Leu Lys Val Leu Ala Thr Gly Leu
1               5                   10                  15

Pro Thr Leu Ile Ser Trp Ile Lys Asn Lys Arg Lys Gln
            20                  25

<210> SEQ ID NO 145
<211> LENGTH: 29
<212> TYPE: PRT
<213> ORGANISM: Artificial Sequence
<220> FEATURE:
<223> OTHER INFORMATION: Melittin-like peptide

<400> SEQUENCE: 145

Lys Leu Lys Tyr Ile Gly Ala Ile Leu Lys Val Leu Ala Thr Gly Leu
1               5                   10                  15

Pro Thr Leu Ile Ser Trp Ile Lys Asn Lys Arg Lys Gln
            20                  25
```

<210> SEQ ID NO 146
<211> LENGTH: 30
<212> TYPE: PRT
<213> ORGANISM: Artificial Sequence
<220> FEATURE:
<223> OTHER INFORMATION: Melittin-like peptide

<400> SEQUENCE: 146

Cys Lys Leu Lys Leu Ile Gly Ala Ile Leu Lys Val Leu Ala Thr Gly
1               5                   10                  15

Leu Pro Thr Leu Ile Ser Trp Ile Lys Asn Lys Arg Lys Gln
            20                  25                  30

<210> SEQ ID NO 147
<211> LENGTH: 30
<212> TYPE: PRT
<213> ORGANISM: Artificial Sequence
<220> FEATURE:
<223> OTHER INFORMATION: Melittin-like peptide
<220> FEATURE:
<221> NAME/KEY: misc_feature
<222> LOCATION: (5)..(5)
<223> OTHER INFORMATION: Xaa is Nle

<400> SEQUENCE: 147

Cys Lys Leu Lys Xaa Ile Gly Ala Ile Leu Lys Val Leu Ala Thr Gly
1               5                   10                  15

Leu Pro Thr Leu Ile Ser Trp Ile Lys Asn Lys Arg Lys Gln
            20                  25                  30

<210> SEQ ID NO 148
<211> LENGTH: 30
<212> TYPE: PRT
<213> ORGANISM: Artificial Sequence
<220> FEATURE:
<223> OTHER INFORMATION: Melittin-like peptide

<400> SEQUENCE: 148

Gly Lys Leu Lys Leu Ile Gly Ala Ile Leu Lys Val Leu Ala Thr Gly
1               5                   10                  15

Leu Pro Thr Leu Ile Ser Trp Ile Lys Asn Lys Arg Lys Gln
            20                  25                  30

<210> SEQ ID NO 149
<211> LENGTH: 30
<212> TYPE: PRT
<213> ORGANISM: Artificial Sequence
<220> FEATURE:
<223> OTHER INFORMATION: D-form Melittin-like peptide

<400> SEQUENCE: 149

Cys Pro Ala Asn Leu Ile Gly Ala Ile Leu Lys Val Leu Ala Thr Gly
1               5                   10                  15

Leu Pro Thr Leu Ile Ser Trp Ile Lys Asn Lys Arg Lys Gln
            20                  25                  30

<210> SEQ ID NO 150
<211> LENGTH: 31
<212> TYPE: PRT
<213> ORGANISM: Artificial Sequence
<220> FEATURE:
<223> OTHER INFORMATION: Melittin-like peptide

<400> SEQUENCE: 150

Asp Glu Pro Leu Arg Ala Ile Gly Ala Ile Leu Lys Val Leu Ala Thr

```
                1               5                  10                  15
Gly Leu Pro Thr Leu Ile Ser Trp Ile Lys Asn Lys Arg Lys Gln
                20                  25                  30

<210> SEQ ID NO 151
<211> LENGTH: 27
<212> TYPE: PRT
<213> ORGANISM: Artificial Sequence
<220> FEATURE:
<223> OTHER INFORMATION: Melittin-like peptide

<400> SEQUENCE: 151

Gly Ile Gly Ala Ile Leu Lys Val Leu Ala Thr Gly Leu Pro Thr Leu
1               5                   10                  15

Ile Ser Trp Ile Lys Asn Lys Arg Lys Gln Cys
                20                  25

<210> SEQ ID NO 152
<211> LENGTH: 27
<212> TYPE: PRT
<213> ORGANISM: Artificial Sequence
<220> FEATURE:
<223> OTHER INFORMATION: Melittin-like peptide

<400> SEQUENCE: 152

Leu Ile Gly Ala Ile Leu Lys Val Leu Ala Thr Gly Leu Pro Thr Leu
1               5                   10                  15

Ile Ser Trp Ile Lys Asn Lys Arg Lys Gln Cys
                20                  25

<210> SEQ ID NO 153
<211> LENGTH: 27
<212> TYPE: PRT
<213> ORGANISM: Artificial Sequence
<220> FEATURE:
<223> OTHER INFORMATION: Melittin-like peptide
<220> FEATURE:
<221> NAME/KEY: misc_feature
<222> LOCATION: (1)..(1)
<223> OTHER INFORMATION: Xaa is Nle

<400> SEQUENCE: 153

Xaa Ile Gly Ala Ile Leu Lys Val Leu Ala Thr Gly Leu Pro Thr Leu
1               5                   10                  15

Ile Ser Trp Ile Lys Asn Lys Arg Lys Gln Cys
                20                  25

<210> SEQ ID NO 154
<211> LENGTH: 30
<212> TYPE: PRT
<213> ORGANISM: Artificial Sequence
<220> FEATURE:
<223> OTHER INFORMATION: Melittin-like peptide

<400> SEQUENCE: 154

Leu Ile Gly Ala Ile Leu Lys Val Leu Ala Thr Gly Leu Pro Thr Leu
1               5                   10                  15

Ile Ser Trp Ile Lys Asn Lys Arg Lys Gln Lys Leu Lys Cys
                20                  25                  30

<210> SEQ ID NO 155
<211> LENGTH: 34
<212> TYPE: PRT
<213> ORGANISM: Artificial Sequence
<220> FEATURE:
```

<223> OTHER INFORMATION: Melittin-like peptide

<400> SEQUENCE: 155

Tyr Ile Gly Ala Ile Leu Lys Val Leu Ala Thr Gly Leu Pro Thr Leu
1               5                   10                  15

Ile Ser Trp Ile Lys Asn Lys Arg Lys Gln Pro Leu Gly Ile Ala Gly
            20                  25                  30

Gln Cys

<210> SEQ ID NO 156
<211> LENGTH: 31
<212> TYPE: PRT
<213> ORGANISM: Artificial Sequence
<220> FEATURE:
<223> OTHER INFORMATION: Melittin-like peptide

<400> SEQUENCE: 156

Leu Ile Gly Ala Ile Leu Lys Val Leu Ala Thr Gly Leu Pro Thr Leu
1               5                   10                  15

Ile Ser Trp Ile Lys Asn Lys Arg Lys Gln Lys Lys Lys Lys
            20                  25                  30

<210> SEQ ID NO 157
<211> LENGTH: 31
<212> TYPE: PRT
<213> ORGANISM: Artificial Sequence
<220> FEATURE:
<223> OTHER INFORMATION: Melittin-like peptide

<400> SEQUENCE: 157

Tyr Ile Gly Ala Ile Leu Lys Val Leu Ala Thr Gly Leu Pro Thr Leu
1               5                   10                  15

Ile Ser Trp Ile Lys Asn Lys Arg Lys Gln Gly Phe Lys Gly Cys
            20                  25                  30

<210> SEQ ID NO 158
<211> LENGTH: 30
<212> TYPE: PRT
<213> ORGANISM: Artificial Sequence
<220> FEATURE:
<223> OTHER INFORMATION: Melittin-like peptide

<400> SEQUENCE: 158

Cys Phe Lys Leu Ile Gly Ala Ile Leu Lys Val Leu Ala Thr Gly Leu
1               5                   10                  15

Pro Thr Leu Ile Ser Trp Ile Lys Asn Lys Arg Lys Gln Cys
            20                  25                  30

<210> SEQ ID NO 159
<211> LENGTH: 25
<212> TYPE: PRT
<213> ORGANISM: Artificial Sequence
<220> FEATURE:
<223> OTHER INFORMATION: Melittin-like peptide

<400> SEQUENCE: 159

Phe Gly Ala Ile Leu Lys Val Leu Ala Thr Gly Leu Pro Thr Leu Ile
1               5                   10                  15

Ser Trp Ile Lys Asn Lys Arg Lys Gln
            20                  25

<210> SEQ ID NO 160
<211> LENGTH: 23

```
<212> TYPE: PRT
<213> ORGANISM: Artificial Sequence
<220> FEATURE:
<223> OTHER INFORMATION: Melittin-like peptide

<400> SEQUENCE: 160

Leu Ile Gly Ala Ile Leu Lys Val Leu Ala Thr Gly Leu Pro Thr Leu
1               5                   10                  15

Ile Ser Trp Ile Lys Asn Lys
            20

<210> SEQ ID NO 161
<211> LENGTH: 21
<212> TYPE: PRT
<213> ORGANISM: Artificial Sequence
<220> FEATURE:
<223> OTHER INFORMATION: Melittin-like peptide

<400> SEQUENCE: 161

Leu Ile Gly Ala Val Leu Lys Val Leu Thr Thr Gly Leu Pro Ala Leu
1               5                   10                  15

Ile Ser Trp Ile Lys
            20

<210> SEQ ID NO 162
<211> LENGTH: 23
<212> TYPE: PRT
<213> ORGANISM: Artificial Sequence
<220> FEATURE:
<223> OTHER INFORMATION: Melittin-like peptide

<400> SEQUENCE: 162

Leu Ile Gly Ala Val Leu Lys Val Leu Thr Thr Gly Leu Pro Ala Leu
1               5                   10                  15

Ile Ser Trp Ile Lys Gly Glu
            20

<210> SEQ ID NO 163
<211> LENGTH: 26
<212> TYPE: PRT
<213> ORGANISM: Artificial Sequence
<220> FEATURE:
<223> OTHER INFORMATION: Reversed and melittin-like sequence

<400> SEQUENCE: 163

Gln Lys Arg Lys Asn Lys Ile Trp Ser Ile Leu Thr Pro Leu Gly Thr
1               5                   10                  15

Ala Leu Val Lys Leu Ile Ala Gly Ile Leu
            20                  25

<210> SEQ ID NO 164
<211> LENGTH: 29
<212> TYPE: PRT
<213> ORGANISM: Artificial Sequence
<220> FEATURE:
<223> OTHER INFORMATION: Reversed and melittin-like sequence

<400> SEQUENCE: 164

Lys Leu Lys Gln Lys Arg Lys Asn Lys Ile Trp Ser Ile Leu Thr Pro
1               5                   10                  15

Leu Gly Thr Ala Leu Val Lys Leu Ile Ala Gly Ile Leu
            20                  25

<210> SEQ ID NO 165
```

```
<211> LENGTH: 27
<212> TYPE: PRT
<213> ORGANISM: Artificial Sequence
<220> FEATURE:
<223> OTHER INFORMATION: Melittin-like peptide

<400> SEQUENCE: 165

Gly Ile Gly Ala Val Leu Lys Val Leu Thr Thr Gly Leu Pro Ala Leu
1               5                   10                  15

Ile Ser Trp Ile Ser Arg Lys Lys Arg Gln Gln
            20                  25

<210> SEQ ID NO 166
<211> LENGTH: 25
<212> TYPE: PRT
<213> ORGANISM: Artificial Sequence
<220> FEATURE:
<223> OTHER INFORMATION: Melittin-like peptide

<400> SEQUENCE: 166

Gly Ile Gly Ala Arg Leu Lys Val Leu Thr Thr Gly Leu Pro Arg Ile
1               5                   10                  15

Ser Trp Ile Lys Arg Lys Arg Gln Gln
            20                  25

<210> SEQ ID NO 167
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 167

Gly Ile Gly Ala Ile Leu Lys Val Leu Ser Thr Gly Leu Pro Ala Leu
1               5                   10                  15

Ile Ser Trp Ile Lys Arg Lys Arg Gln Glu
            20                  25

<210> SEQ ID NO 168
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 168

Gly Ile Gly Ala Val Leu Lys Val Leu Thr Thr Gly Leu Pro Ala Leu
1               5                   10                  15

Ile Gly Trp Ile Lys Arg Lys Arg Gln Gln
            20                  25

<210> SEQ ID NO 169
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 169

Gly Ile Gly Ala Val Leu Lys Val Leu Ala Thr Gly Leu Pro Ala Leu
1               5                   10                  15

Ile Ser Trp Ile Lys Arg Lys Arg Gln Gln
            20                  25
```

<210> SEQ ID NO 170
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 170

Gly Ile Gly Ala Val Leu Lys Val Leu Ser Thr Gly Leu Pro Ala Leu
1               5                   10                  15

Ile Ser Trp Ile Lys Arg Lys Arg Gln Gln
            20                  25

<210> SEQ ID NO 171
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 171

Gly Ile Gly Ala Ile Leu Arg Val Leu Ala Thr Gly Leu Pro Thr Leu
1               5                   10                  15

Ile Ser Trp Ile Lys Asn Lys Arg Lys Gln
            20                  25

<210> SEQ ID NO 172
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 172

Gly Ile Gly Ala Ile Leu Lys Val Leu Ala Thr Gly Leu Pro Thr Leu
1               5                   10                  15

Ile Ser Trp Ile Lys Arg Lys Arg Lys Gln
            20                  25

<210> SEQ ID NO 173
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 173

Gly Ile Gly Ala Ile Leu Lys Val Leu Ala Thr Gly Leu Pro Thr Leu
1               5                   10                  15

Ile Ser Trp Ile Lys Lys Lys Lys Gln Gln
            20                  25

<210> SEQ ID NO 174
<211> LENGTH: 32
<212> TYPE: PRT
<213> ORGANISM: Artificial Sequence
<220> FEATURE:
<223> OTHER INFORMATION: Melittin-like peptide

<400> SEQUENCE: 174

Gly Ile Gly Ala Ile Leu Lys Val Leu Ala Thr Gly Leu Pro Thr Leu
1               5                   10                  15

Ile Ser Trp Ile Lys Asn Lys Arg Lys Gln Gly Ser Lys Lys Lys Lys
            20                  25                  30

<210> SEQ ID NO 175
<211> LENGTH: 28
<212> TYPE: PRT
<213> ORGANISM: Artificial Sequence
<220> FEATURE:
<223> OTHER INFORMATION: Melittin-like peptide

<400> SEQUENCE: 175

Lys Lys Gly Ile Gly Ala Ile Leu Lys Val Leu Ala Thr Gly Leu Pro
1               5                   10                  15

Thr Leu Ile Ser Trp Ile Lys Asn Lys Arg Lys Gln
            20                  25

<210> SEQ ID NO 176
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 176

Gly Ile Gly Ala Ile Leu Glu Val Leu Ala Thr Gly Leu Pro Thr Leu
1               5                   10                  15

Ile Ser Trp Ile Lys Asn Lys Arg Lys Gln
            20                  25

<210> SEQ ID NO 177
<211> LENGTH: 24
<212> TYPE: PRT
<213> ORGANISM: Artificial Sequence
<220> FEATURE:
<223> OTHER INFORMATION: Melittin-like peptide

<400> SEQUENCE: 177

Gly Ile Gly Ala Val Leu Lys Val Leu Thr Thr Gly Leu Pro Ala Leu
1               5                   10                  15

Ile Ser Trp Ile Lys Arg Lys Arg
            20

<210> SEQ ID NO 178
<211> LENGTH: 22
<212> TYPE: PRT
<213> ORGANISM: Artificial Sequence
<220> FEATURE:
<223> OTHER INFORMATION: Melittin-like peptide

<400> SEQUENCE: 178

Gly Ile Gly Ala Val Leu Lys Val Leu Thr Thr Gly Leu Pro Ala Leu
1               5                   10                  15

Ile Ser Trp Ile Lys Arg
            20

<210> SEQ ID NO 179
<211> LENGTH: 26
<212> TYPE: PRT
<213> ORGANISM: Artificial Sequence
<220> FEATURE:
<223> OTHER INFORMATION: Melittin-like peptide

```
<400> SEQUENCE: 179

Cys Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 180
<211> LENGTH: 26
<212> TYPE: PRT
<213> ORGANISM: Artificial Sequence
<220> FEATURE:
<223> OTHER INFORMATION: Reversed and melittin-like sequence

<400> SEQUENCE: 180

Gln Gln Arg Lys Arg Lys Ile Trp Ser Ile Leu Ala Pro Leu Gly Thr
1               5                   10                  15

Thr Leu Val Lys Leu Val Ala Gly Ile Gly
            20                  25

<210> SEQ ID NO 181
<211> LENGTH: 26
<212> TYPE: PRT
<213> ORGANISM: Artificial Sequence
<220> FEATURE:
<223> OTHER INFORMATION: Reversed and melittin-like sequence

<400> SEQUENCE: 181

Gln Gln Arg Lys Arg Lys Ile Trp Ser Ile Leu Ala Pro Leu Gly Thr
1               5                   10                  15

Thr Leu Val Lys Leu Val Ala Gly Ile Cys
            20                  25

<210> SEQ ID NO 182
<211> LENGTH: 26
<212> TYPE: PRT
<213> ORGANISM: Artificial Sequence
<220> FEATURE:
<223> OTHER INFORMATION: Reversed and melittin-like sequence

<400> SEQUENCE: 182

Gln Gln Lys Lys Lys Lys Ile Trp Ser Ile Leu Ala Pro Leu Gly Thr
1               5                   10                  15

Thr Leu Val Lys Leu Val Ala Gly Ile Cys
            20                  25

<210> SEQ ID NO 183
<211> LENGTH: 26
<212> TYPE: PRT
<213> ORGANISM: Artificial Sequence
<220> FEATURE:
<223> OTHER INFORMATION: Reversed and melittin-like sequence

<400> SEQUENCE: 183

Gln Lys Arg Lys Asn Lys Ile Trp Ser Ile Leu Thr Pro Leu Gly Thr
1               5                   10                  15

Ala Leu Val Lys Leu Ile Ala Gly Ile Gly
            20                  25

<210> SEQ ID NO 184
<211> LENGTH: 26
<212> TYPE: PRT
<213> ORGANISM: Artificial Sequence
<220> FEATURE:
```

-continued

```
<223> OTHER INFORMATION: Reversed and melittin-like sequence

<400> SEQUENCE: 184

Gln Gln Arg Lys Arg Lys Ile Trp Ser Ile Leu Ala Ala Leu Gly Thr
1               5                   10                  15

Thr Leu Val Lys Leu Val Ala Gly Ile Cys
            20                  25
```

UNITED STATES PATENT AND TRADEMARK OFFICE
CERTIFICATE OF CORRECTION

PATENT NO. : 10,006,025 B2
APPLICATION NO. : 14/740307
DATED : June 26, 2018
INVENTOR(S) : Christine I Wooddell et al.

It is certified that error appears in the above-identified patent and that said Letters Patent is hereby corrected as shown below:

In the Claims

In Column 127, Line 23, in Claim 1, delete "5' GGAACUUGGUGAUGAUAU 3'" and insert -- 5'-GGAACUUGGUGAUGAUAU-3' --.

In Column 128, Line 51, in Claim 23, after "method" insert -- of --.

Signed and Sealed this
Twentieth Day of October, 2020

Andrei Iancu
*Director of the United States Patent and Trademark Office*